(12) United States Patent
Pitcovski et al.

(10) Patent No.: US 6,663,872 B1
(45) Date of Patent: Dec. 16, 2003

(54) HEMORRHAGIC ENTERITIS VIRUS DNA SEQUENCES, PROTEINS ENCODED THEREBY AND VARIOUS USES THEREOF

(75) Inventors: Jacob Pitcovski, Korazim (IL); Margalit Mualem, Kiryat Shemona (IL); Ziv Rei Koren, Kibbutz Lotem (IL); Simcha Krispel, Korazim (IL); Esther Shmueli, Tirat HaCarmel (IL); Yifat Peretz, Kiryat Shmona (IL); Bezalel Gutter, Jerusalem (IL); Gilad Gallili, Jerusalem (IL); Amnon Michael, Hoffit (IL); Doron Goldberg, Metula (IL)

(73) Assignee: ABIC Ltd., Jerusalem (IL)

( * ) Notice: Subject to any disclaimer, the term of this patent is extended or adjusted under 35 U.S.C. 154(b) by 0 days.

(21) Appl. No.: 09/717,364

(22) Filed: Nov. 20, 2000

Related U.S. Application Data

(63) Continuation of application No. PCT/IL99/00268, filed on May 19, 1999.

(30) Foreign Application Priority Data

May 20, 1998 (IL) .................................................. 124567

(51) Int. Cl.[7] .......................... A61K 39/23; A61K 39/12
(52) U.S. Cl. .............................. 424/233.1; 424/204.1; 424/199.1; 435/91.1; 435/69.1; 435/235.1; 435/325; 536/23.72
(58) Field of Search ........................ 424/233.1, 204.1, 424/199.1; 435/41.1, 69.1, 41.33, 235.1, 325, 6; 536/23.72

(56) References Cited

U.S. PATENT DOCUMENTS 4,388,298 A  *  6/1983  Nazerian et al. ............... 424/89

FOREIGN PATENT DOCUMENTS

WO      WO 96/03508    *  2/1996

OTHER PUBLICATIONS

Hess et al , Virology, 1997, vol. 238, pp. 145–156.*
Jucker et al , Journal of General Virology, 1997, vol. 77, pp. 469–479.*
Suresh et al , Virus Research, 1995, vol. 39, pp. 289–297.*
Nazerian et al , Avian Diseases, 1982, vol. 26 (4) 816–827.*
Boursnell M.E.G. et al., "A Recombinant Fowlpox Virus Expressing the Hemagglutinin–Neuraminidase Gene of Newcastel Disease Virus (NDV) Protects Chickens Against Challenge by NDV", *Virology*, 1990, 178(1) : 297–300.
Yamanouchi et al., "Immunisation of Cattle with a Recombinant Vaccinia Vector Expressing the Haemagglutinin Gene of Rinderpest Virus", *The Veterinary Record*, 1993, 132: 152–156.

* cited by examiner

*Primary Examiner*—Ali R. Salimi
(74) *Attorney, Agent, or Firm*—John P. White; Cooper & Dunham LLP

(57) ABSTRACT

The present invention relates to a DNA sequence comprising a nucleotide sequence encoding Hemorrhagic Enteritis virus. It is well known to the man of the art that determining the complete sequence of a virus enables the isolation and identification of the different genes contained therein, and their utilisation for different purposes such as for vaccination purposes, as potential vectors for gene delivery to be used in recombinant vaccination or for gene therapy. In addition, the sequence may be employed for diagnostic purposes wherein the disclosed sequence of any part thereof be used for the development of specific primers for Polymerase Chain Reaction processes (PCR) or as probes. The invention thus also concerns with HEV proteins encoded by the sequence of the invention or functional fragments thereof and to some of the uses of said sequences and proteins.

9 Claims, 8 Drawing Sheets

FIGURE 2

Figure 1:
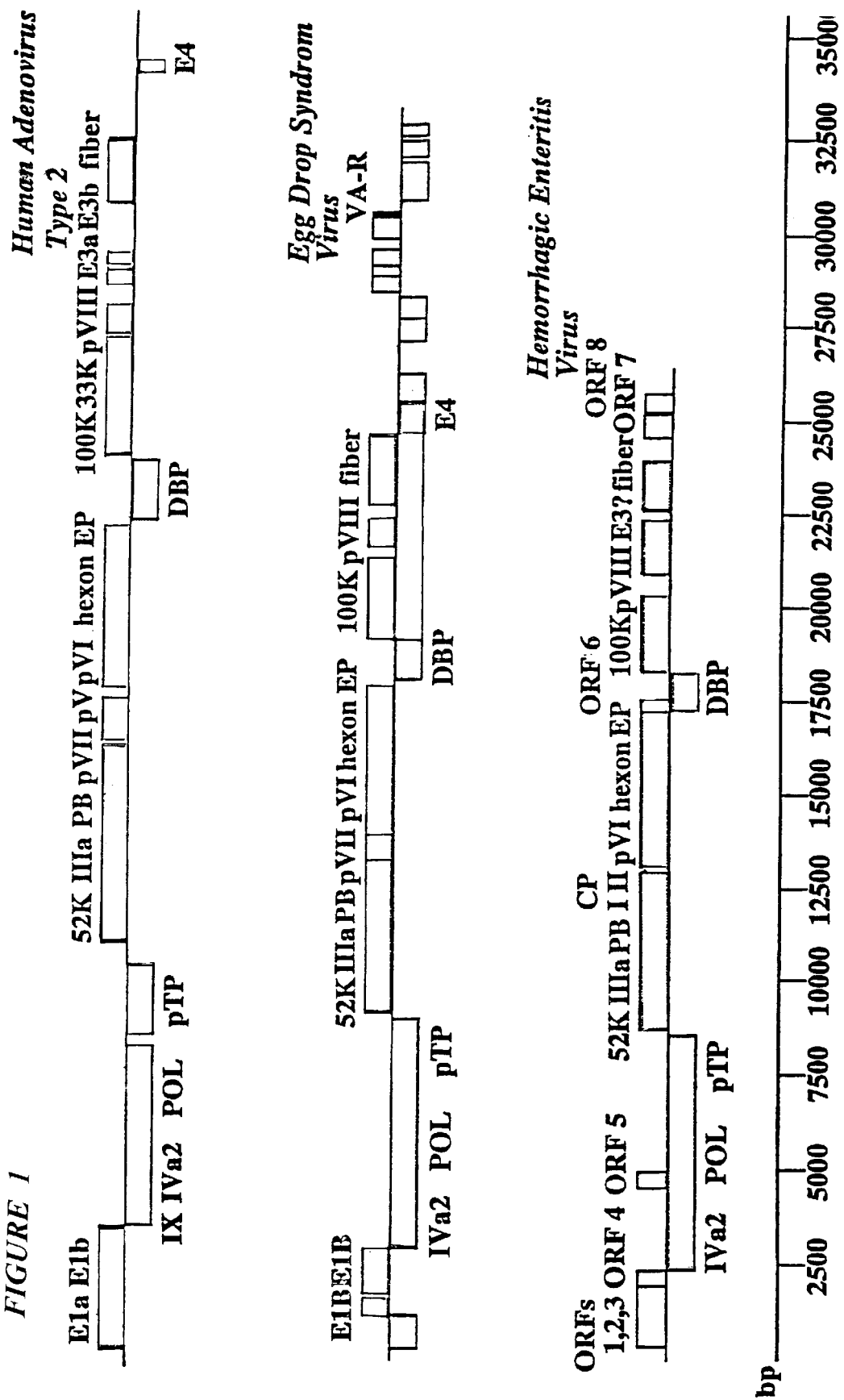

| | | | | | | | |
|---|---|---|---|---|---|---|---|
| EDS | 220 | G V R Y G S Q R Y C Y |
| OVINE | 211 | G V R N F T R R Y C Y |
| HEV | 221 | G V R F T S T N Q C Y |
| CELO | 213 | G V R A T A T R M C Y |
| Ad2 | 240 | G V R Q S L K R R R C F |

FIGURE 3

```
CELO   -MSGTTETQLRDLLSSMHLRHRFLGVFDKSFPGFLDPHVPASAIVN--TGSRASGGMHWI
HEV    -MAGTSSSELITLVRSLGLGSYFLGVYDKHFPGFLNDRRLAYAIVN--TGDYMSGGLHWI
EDS    -MSGTSESELKALMKSLGIAGNFLGTFDCTFPGFINKHKRQTAIINFTTGSRASGGLIWL
AD12   -M-GSSEQELTAIVRDLGCGPYFLGTFDKRFPGFVSRDRLSCAIVN---TAGRETGGVIWL
AD2    -M-GSSEQELKAIVKDLGCGPYFLGTYDKRFPGFVSPHKLACAIVN---TAGRETGGVIHM
         *  :: .:  *     .   **   *    *   *****: : :    ** . ** ::

CELO   GFAFDPAAGRCYMFDPFGWSDQKLWELYRVKYNAFMRRTGLRQP-DRCFT--LVRSTEAV
HEV    AFAYDPNGRKFYIFDPFGWSKKELWKFEYKFQYDRIVRRTALQN--GRCIK--LVRSVDTV
EDS    AFAWDPLRYTIYMFDPLGWKEKDLFKLYGFSYKTMIKRSALQSD-NRCFTVKLVKNTEAV
AD12   AFGWNPKSHTCYLFDPFGFSDQRLKQIYQFEYESLLRRSALAATKDRCVT--LEKSTQTV
AD2    AFAWNPRSKTCYLFDPFGFSDQRLKQVYQFEYESLLRRSAIASSPDRCIT--LEKSTQSV
        *    *   ****.* :*.. :*  : :      :.**: :.    ::    *::*: *

CELO   QCPCSAACHLFSALFIVSFDRYRSKPMDGNPVIDTVVGVKHENMNSPPYRDILHRNQERT
HEV    QCPCSAACHLYCVLFLASFYYFRNSPMYNNPIIDVVTGVPHSKMKSSYGIAILHCNQERL
EDS    QCTCAGSCHLFCVFFLYCFNLCHINPFEAS--IFQAMHGTSPALYPSKPHLFTLHANQQML
AD12   QGPFSAACHLFCCMFLHAFTHWPDHPMDKNPTMDLLTGVPNCMLQSPQVVGTLQRNQNEL
AD2    QGPNSAACHLFCCMFLHAFANWPQTPMDHNPTMNLITGVPNSMLNSPQVQPTLRRNQEQL
        *  * .:*  :  :           .      .     : *              **  :

CELO   YYWWTKNSAYFRAHQEELRRETALNALPENHV----------
HEV    YNWLYYNSVYFRDNELEIKRNTRINSILVHYLFIVLFLFEAR-
EDS    YDFLRSHSSYFVNNERILVCNTKLNLININHQ-----------
AD12   YKFLNNLSPYFRHNRERIEKATSFTKMQNGLK-----------
AD2    YSFLERHSPYFRSHSAQIRSATSFCHLKN-M------------
        *  :    **  :    :   :  ::
```

*FIGURE 4A*

```
                .         .         .         .
HEV     1 CAATCAATATATATACCG.......CATGCTTGG.GAGGGGATTTCG 39
          | ||  ||||||||| ||        | ||  || | | ||  |||
OVa     1 CTATTCATATATATATAACGTTGCACAGAGGCGGGCGTGTGGGTTTT. 46
```

*FIGURE 4B*

```
               .         .         .         .         .
HEV     1 ..CA.ATCAATATATATACC..GC.....ATGCTTGGGAGGGGA..TTTCG.. 39
            ||  ||| ||   | |||  ||     ||||    |||| ||  |  ||
EDS     1 CTCATGTCATTAATAAGACCATGCAGAAAATGCAAATGAGGCGAAGTGACGTA 53
```

*FIGURE 5A-1*

1. 52K

9461 GTC TTC <u>TAA</u> GGA TGT GGC AGA GAT CTT ATC TGG AAA  9497

2. 100K

20217 CCC AGG <u>TAG</u> TTA TTC <u>TAA</u> ATG GAA GCA ATA CTG CAC  20252

3. PENTON BASE

12336 TTG CAA <u>TAA</u> TGC ATT CTG TTG TTT ATT CTC CCA GGG  12360

4. CPI

12699 GTA GGT <u>TAG</u> AAA TGT <u>TTG</u> <u>AAA</u> ATT <u>TAG</u> CAC CCA GAA  12734

5. CPII

12878 TCT AAG <u>TAG</u> <u>TAG</u> TGT TTT TTC TTA CAG ATA TGT TTT CAA  12913

6. HEXON

16323 GTA <u>TAA</u> AAT GGC TGG AAC TTC AAG TTC AGA ATT <u>GAT</u>  16358

*FIGURE 5A-2*

7. PVI

13591 TGT TAT TAA TTT TTT AGA TGG ACA TAT CAA ATG CTA 13636

8. ENDOPROTEASE

16966 GCG CGT TAA CAA AAA GCG TCA TCA TCA CTT TCC ACC 17001

9. PVIII

21361 AAA GCA TAA ACA TGA GTG TCA ATC TAT TAA TTG TAT 21396

10. PTP

6770 CCA AGA TGA GCA AAT ACA TTT ATA CCA CTC AAA ACG 6734

11. FIBER

23873 ATA GGC TGA TGA AAA TAA ACT AGT GAT GCA ACT TTC 23907

12. IIIa

10968 CCA TAC TGA CCA ATT CCT GGT TCA TTT AGA TGG AAT 11004

*FIGURE 5A-3*

13. Iva2

2339 GAA ATT TAA TAA AAT TTT TAT TCA AAC TTT TCA CAT   2303

14. E2A DBP

16979 TTT TGT TAA CGC GCA AAT AAA AAC AAT ACA ATA AAG   16943

15. E3

22106 TCT TAT TGA TAG ATT GTT TAC GAA GCA GAA GCA GAG   22141

16. POL

3435 GAT GAA TAA TGA AGT TGA AGA ATT CTA CGA TGT AGT   3399

FIGURE 6

| | |
|---|---|
| MATPGKRSAE EPDQQTLKKS<br>KQSDQSQGLN LAYPFDKITE<br>FEATPPFIHV GQGLDISD | *Amino terminal acid* |

| | |
|---|---|
| LSL  NMRIG KGL KFENGNLVVS<br>DOO  YNVTP PLI ADQST<br>LGL   KYNP DVL SLTH<br>SGA   LTLP TIQ HPLQASAGK<br>FEL  ALSSG LKS DDQG<br>LTL   DLDP VFS TESSK<br>FLL  NCSLP LDK NSDK<br>LTL  KFGNG LGL NNDQLE<br>NTM  TYNLP LKR DG<br>TNV  SLSFG TNF KILNEM<br>LTL  NLVAP MSN SAGG<br>LAL  QFKSP LSA DDGI<br>LSI KTPTSL ITG NKLG<br>        G<br>IRL  APNSG LQI TPNGLAVSVN<br>AVQ  ILSSP LIT AASI<br>GPP  TTNVTG TVS | *Shaft* |

| | |
|---|---|
| PGRATNGQFV TKTAKVLRYK<br>FVRWDALLII QFIDNIGVIE<br>NPTFYRNKSI ELRSADFLSP<br>TLNNTYIVPL NGGVRVESPT<br>IPVQLEVILE NNSSFIQVGF<br>VRLTVKNGNP HMIIQCNPVP<br>GNIKMIKIKS VMLFTCLIG | *Knob* |

HEMORRHAGIC ENTERITIS VIRUS DNA SEQUENCES, PROTEINS ENCODED THEREBY AND VARIOUS USES THEREOF

This application is a continuation of PCT International Application No. PCT/IL99/00268, filed May 19, 1999, claiming priority of Israeli Patent Application No. 124567, filed May 20, 1998, the contents of which are hereby incorporated in their entireties into the present application.

FIELD OF THE INVENTION

The present invention relates to a DNA sequence which comprises a nucleotide sequence encoding the *Hemorrhagic Enteritis* Virus, to proteins encoded thereby, to vectors and DNA constructs comprising the said DNA sequence or essential fragments thereof, and to various uses of the DNA sequence and the proteins encoded thereby.

BACKGROUND OF THE INVENTION

One of the principal diseases which suppress the immune system in turkeys is caused by infection with *Hemorrhagic Enteritis* Virus (HEV). HEV belongs to the Adenoviridae family. This family consists of serotypes that infect mammals (Mastadenoviridae) and avian (Aviadenoviridae) [Shenk T. Virology, pp. 2111–2148 (1996), B. N. Fields, D. M. Knipe and P. M. Howley (Eds) Lippincott-Raven New York]. HEV, together with marble spleen disease of pheasant and splenomegaly virus of chickens, are classified as type II avian adenovirus (Ad) [Domermuth C. H. and Gross W. B., Diseases of Poultry 8th ed. Pp.511–516, H. J. Barnes, B. W. Calnck, W. B. Reid and Yoder H. W. (Eds) Iowa State University Press (1984)] which is serologically distinct from type I and type III isolated from chickens infected by fowl Ad (FAV) 1–12 and egg drop syndrome (EDS) virus, respectively.

The HEV, as other type II Ad's, is a non-enveloped DNA virus, with a diameter of about 70–90 nm and an icosahedral symmetry. The genome is linear, double-stranded DNA and with a size estimated to be approximately 25.5 kb [Jucker et al J. Gen. Virol. 77:469–479 (1996)]. Partial sequence (about 4 kb) of the HEV genome has been recently published [Jucker et al. (1996) ibid.], while full sequences of several human Ad's (types 2, 5, 12 and 40), avian Ad's (CELO and egg drop syndrome (EDS)) and ovine Ad were published and may be found in EMBL and GenBank data bases. The e organization of all human Ad's is very similar [Shenk T. (1996) ibid.]. However, in some non-human Adenovirus (Ad) sequences (CELO, Ova and EDS) no similarity was found for various regions of human Ad [Chiocca, S., et. al. J. Virol. 70:2939–3949 (1996); Vrati, S., et. al Virology 220:186–199 (1996); Hess, M. et. al., Virology 238:145–156 (1997), respectively].

HEV replicates in the host cell nucleus and consists of 11 proteins, encoded by its DNA segment. The molecular weights of the HEV proteins range from 14 kD to 97 kD [Nazerian K. L., et al. Avian Dis. 35:572–578 (1991)]. The 97 kD polypeptide is the structural hexon protein, a monomer of the major outer capsid. Other structural proteins are the penton base protein, having a predicted size of about 50 kD and the fiber protein which anchors the penton base protein. This fiber protein consists of a tail and a globular head, which plays an important role in the first attachment of the virus to the cell receptor.

The virus infects turkeys and causes a disease which is characterized by depression, splenomegaly, intestinal hemorrhages and immuno-suppression [Domermuth C. H., & Gross W. B. (1991) Diseases of Poultry, 9th Edition, M. S. Hofstad et al. Eds. Iowa State University Press, Ames, Iowa]. The virus replicates in B cells and macrophages [Suresh M. & Sharma J. M. J. Virol. 70:30–36 (1996)] and is concentrated in large amounts in the spleen. Since B cells play an important role in the primary immune response, afflicted birds suffer mostly from weight loss.

Infection of birds by the HEV is especially prevalent during the ages of 7 to 9 weeks [Domermuth C. H. & Gross W. B., Diseases of Poultry, Iowa State University Press, 8th Edition pp. 511–516 (1984)]. Younger birds are protected by maternal antibodies [Van den Hurk, J. V. Avian Dis. 30:662–671 (1986); Harris J. R. & Domermuth C. H., Avian Dis. 21:120–122 (1977); Fadly, A. M. & Nazerian K. Avian Dis. 33:778–786 (1989)]. The rate of mortality of infected birds is high and, since the immune response is damaged, the surviving birds exhibit high vulnerability to other diseases. Moreover, infection with HEV reduces the effectiveness of response to various vaccines. As a result of lowered resistance, an outbreak of a HEV infection may further lead to outbreaks of other diseases. Naturally, such events result in heavy financial loss to the breeders.

Infectious diseases in animals, and in particular in farm animals, are one of the most important economic factors in agriculture, for example, in the poultry industry. The minimalization of losses from diseases, by means of effective vaccines, plays a major part in achieving profit in today's intensive agricultural industry. The health of domesticated animals depends on management, on a proper vaccination system and on the availability of effective vaccines.

Since the price of a single farm animal is relatively low, the cost of production and delivery of the vaccine becomes critical. Naturally, if cost of the production of the vaccine is too high, its use will not be economically worthwhile.

In the last decade recombinant adenoviral vectors have become a subject for research as vectors in gene therapy [Kozarsky K. F. & Wilson J. M., Current Options in Genetics and Development 3:499–503 (1993)]. The complete sequence of the viral DNA is essential for enabling successful manipulation of the virus, for use in gene delivery. To date, recombinant Ad's have been employed in a variety of gene therapy applications as carriers of foreign genes, as obtained with vaccinia and fowlpox [Yamanouchi K. K., et al. The Veterinary Record 13:152–156 (1993); Boursnell M. E. G. et al Virology 265:18634–18642 (1990), respectively] and in sub-unit vaccination [Israel Patent Application No.122626].

One aim of the present invention is to construct a recombinant HEV. There are a number of advantages in utilizing an adenoviridae type transfection and expression system such as the HEV derived vector of the present invention. These viruses are easy to grow giving high titers, and both the virions and the viral genome are very stable. Very high levels of expression are possible since most of the macromolecular biosynthesis in adenovirus-infected cells is virus directed at late time points post infection. Proteins made in Ad-derived expression systems would be expected to have all the post-translational modifications that might be important in determining their functional and antigenic properties, and may thus be useful for therapeutic, diagnostic or vaccination purposes.

In addition, the Ad genome is relatively easy to manipulate by recombinant DNA techniques, allowing incorporation of foreign genes as large a 7.5 kb. The ability or recombinant Ad's to terminally transduce differentiated cells in vivo has made these vectors important candidates for many gene therapy applications [S. I., Michael et al. Gene Therapy 2:660–668 (1995)]. Evidently, knowledge of the complete sequence of the viral DNA is needed in order to perform the required manipulations in the sequence.

Although permissive infections are ultimately lytic, infected cells remain intact until relatively late in infection, making the collection of concentrated virus and virus specified intracellular proteins fairly visible.

SUMMARY OF THE INVENTION

The present invention relates to a DNA sequence which comprises (a) a nucleotide sequence substantially as shown in SEQ ID NO:1; or (b) a nucleotide sequence which corresponds to the sequence substantially as shown in SEQ ID NO:1 within the scope of the degeneracy of the genetic code; or (c) a nucleotide sequence which hybridizes, under conditions that allow such hybridization to occur, with the sequences according to (a) or (b) or with a fragment thereof.

The DNA sequence of the invention encodes a *Hemorrhagic Enteritis* Virus (HEV) and biologically functional homologues and fragments thereof, or a non-virulent HEV which is capable of infecting a host cell upon exposure thereto.

The invention also concerns with a DNA sequence comprising (a) at least one nucleotide sequence selected from the nucleotide sequences substantially as shown in SEQ ID NO:2, SEQ ID NO:4, SEQ ID NO:8, SEQ ID NO:10, SEQ ID NO:12, SEQ ID NO:16, SEQ ID NO:18, SEQ ID NO:20, SEQ ID NO:22, SEQ ID NO:24, SEQ ID NO:26, SEQ ID NO:28 and SEQ ID NO:30 and functional fragments thereof, said fragment being other than the nucleotide sequences substantially as shown in SEQ ID NO's:6 and 14 and other than the nucleotide sequence comprising nucleotide bases 187 to 1358 of the nucleotide sequence substantially as shown in SEQ ID NO:22;or (b) at least one nucleotide sequence selected from the nucleotide sequence which corresponds to the above sequences, within the scope of the degeneracy of the genetic code; or (c) a nucleotide sequence which hybridizes, under conditions that allow such hybridization to occur, with the sequence according to (a) or (b) or with a fragment thereof.

In a second aspect, the invention relates to a vector comprising the DNA sequence of the invention or deletions, insertions, mutations, replacements or modifications thereof.

In addition, the invention relates to a DNA construct comprising the DNA sequence of the invention or deletions, insertions, mutations, replacements or modifications thereof and at least one therapeutic exogenous nucleotide sequence operably linked thereto, the DNA construct being capable of transfecting a host cell, upon exposure thereto, with the exogenous nucleotide sequence, the exogenous nucleotide sequence being a sequence which is not made or contained in the cell or is made or contained in the cell in defective form.

In yet a further aspect, the invention relates to a DNA construct for the expression of a therapeutic protein or peptide product in a host cell, comprising a vector of the invention and at least one exogenous nucleotide sequence operably linked thereto which encodes the protein or peptide product.

In another aspect, the invention concerns host cells transformed with a nucleotide sequence of the invention and with host cells transfected with the DNA constructs of the invention.

In yet an additional aspect, the invention relates to a protein or peptide expressed by the host cells of the invention, wherein the protein or peptide product is a therapeutic protein or peptide product which is not made or contained in the cell, or is a therapeutic protein or peptide product which is made or contained in the cell in abnormally low amount, or is a therapeutic protein or peptide product which is made or contained in the cell in defective form or is a therapeutic protein or peptide product which is made or contained in the cell in physiologically abnormal amounts.

Alternatively, the invention relates to a protein or peptide product comprising a sequence substantially as shown in SEQ ID NO:3, SEQ ID NO:5, SEQ ID NO:9, SEQ ID NO:11, SEQ ID NO:13, SEQ ID NO:17, SEQ ID NO:19, SEQ ID NO:21, SEQ ID NO:23, SEQ ID NO:25, SEQ ID NO:27, SEQ ID NO:29, SEQ ID NO:31 or functional equivalents and fragments thereof, said fragment being other than the amino acid sequences substantially as shown in SEQ ID NO's 6 and 14 and other than the amino acid sequence comprising amino acids 63 to amino acid 454 of the amino acid sequence substantially as shown in SEQ ID NO 23.

The invention also relates to a vaccine for immunizing a domesticated animal against at least one specific antigen comprising the DNA construct of the invention or the protein of the invention, optionally further comprising pharmaceutically acceptable carriers, diluents and additives.

Pharmaceutical compositions comprising as active ingredient a therapeutically effective amount of the DNA construct of the or of the cells of the invention or of the therapeutic protein or peptide product of the invention are also within the scope of the invention.

Finally, the different uses of the nucleotide sequence of the invention or the DNA constructs of the invention or the proteins of the invention in the preparation of a vaccine or a pharmaceutical composition also constitute part of the invention.

DESCRIPTION OF THE FIGURES

FIG. 1 A schematic representation of the genome organization of HEV and a comparison to EDS and Ad2 genomes Genes of the HEV are referred to by the nomenclature of the corresponding sites in other Ad's. Locations of predicted sequences are indicated by full boxes. ORF's starting with the codon for methionine (Met) and which encode an amino acid sequence having more than 100 residues, and with no homology to any known Ad ORF, are designated 'ORF1' to 'ORF8' and indicated by empty boxes. EDS and Ad2 sequences were pooled from GenBank (Accession Nos. Y09598 and J01917, respectively). The upper boxes designate genes found on the upper strand. Abbreviations: POL: DNA polymerase; pTP: precursor terminal protein; CBP: DNA binding protein; EP: endoproteinase.

FIG. 2 Alignment of the last 11 amino acid at the C-terminal of pVI of HEV with other Ad's The alignment was obtained by the Pileup program which is part of the GCG software package (see Example 4). Amino acids identical in all five viruses are boxed in black. Amino acids which are identical or similar among some of the viruses are indicated by gray boxes.

FIG. 3 Amino acid sequence alignment of endoproteinase of five Ad's

The alignment was obtained by the ClustalX software (see Example 4). The pairwise and multiple alignment parameters were 6 for gap opening penalty and 0.1 for gap extension penalty. The sequences are ordered according to their similarity. The conserved residues of the active site are shaded gray. Asterisks designate identical residues in all sequences and a colon designates conserved substitutions. A dot indicates a position in which more than 50% of the residues are identical.

FIG. 4 Invert terminal repeats (ITR) of HEV

The ITR of HEV was compared with the ITR's of Ova (FIG. 4a) and EDS (FIG. 4b). The alignment was obtained by Bestfit program which is part of the GCG software package (see Example 4). The gap opening parameter of the program was set to 15 and the gap extenuation parameter to 1.

FIGS. 5A-1, 5A-2 and 5A-3 HEV fiber amino acid organization

FIG. 6 HEV genes.

The 3' end of HEV genes with the following 20 nucleotides wherein the stop codons are underlined.

DETAILED DESCRIPTION OF THE INVENTION

The present invention relates to a DNA sequence which comprises (a) a nucleotide sequence substantially as shown in SEQ ID NO:1; or (b) a nucleotide sequence which corresponds to the sequence substantially as shown in SEQ ID NO:1 within the scope of the degeneracy of the genetic code; or (c) a nucleotide sequence which hybridizes, under conditions that allow for such hybridization to occur, with the sequences according to (a) or (b) or with a fragment thereof The DNA sequence of the invention encodes for *Hemorrhagic Enteritis* Virus (EV). The genome of HEV, which consists of this sequence is a linear, double-stranded DNA in the size of approximately 25.5 kb (SEQ ID NO:1). Evidently, the complete sequence of the virus enables the isolation and identification of the different genes contained therein, and their utilization for different purposes such as for vaccination purposes, as potential vectors for gene delivery to be used in recombinant vaccination or for gene therapy. In addition, the sequence may be employed for diagnostic purposes wherein the disclosed sequence of any part thereof be used for the development of specific primers for Polymerase Chain Reaction processes (PCR) or as probes.

Any sequence which, at the nucleotide level, has a homology of about 95% or at least 95% to the sequence of the invention or any biologically functional homologues and fragments of the sequence may also constitute part of the invention. Such sequences preferably encode a non-virulent HEV which is capable of infecting a host cell upon exposure thereto. Thus, the invention also concerned with a non-virulent HEV encoded by the DNA sequence of the invention.

In the same aspect the invention relates to a DNA sequence comprising (a) at least one nucleotide sequence selected from the nucleotide sequences substantially as shown in SEQ ID NO:2, SEQ ID NO:4, SEQ ID NO:8, SEQ ID NO:10, SEQ ID NO:12, SEQ ID NO:16, SEQ ID NO:18, SEQ ID NO:20, SEQ ID NO:22, SEQ ID NO:24, SEQ ID NO:26, SEQ ID NO:28 and SEQ ID NO:30; or (b) at least one nucleotide sequence selected from the nucleotide sequence which corresponds to the sequences substantially as shown in SEQ ID NO:2, SEQ ID NO:4, SEQ ID NO:8, SEQ ID NO:10, SEQ ID NO:12, SEQ ID NO:16, SEQ ID NO:18, SEQ ID NO:20, SEQ ID NO:22, SEQ ID NO:24, SEQ ID NO:26, SEQ ID NO:28 and SEQ ID NO:30, within the scope of the degeneracy of the genetic code; or (c) a nucleotide sequence which hybridizes, under conditions that allow such hybridization to occur, with the sequence according to (a) or (b) or with a fragment thereof. further, the invention relates to functional fragments of the above sequences, being other than the sequences shown in SEQ ID NO:6 and 14 or other than the nucleic acid sequence comprising nucleotides 187 to 1358 of the nucleic acid sequence substantially as shown in SEQ ID NO:22, corresponding to SEQ ID NO:3 described in PCT/IL98/00609, incorporated herein by reference, or to derivatives thereof. The said sequence described in PCT/IL98/00609 corresponds to the sequence form nucleic acid 187 to nucleic acid 1358 within SEQ ID NO:22 of the present invention.

All of the said sequences are derived from the DNA sequence substantially as shown in SEQ ID NO:1 and encode, respectively, the proteins designated hereinafter as 52K, IIIa, core protein I (CPI), core protein II (CPII), pVI, endoproteinase (EP), 100K, pVIII, the complete fiber, IVa2, DNA polymerase (POL), pTP and the DNA binding protein (DBP). The therapeutic merits of these proteins and of the nucleotide sequences encoding them are well recognized by the man of the art. For example, identification of nucleotide and amino acid sequences of the HEV structural proteins (hexon (SEQ ID NO:14), penton base (SEQ ID NO:6) and fiber proteins) may be utilized in the preparation of a sub-unit vaccine against the virus. In addition, since the fiber protein (FIGS. 5A-1, 5A-2 and 5A-3) is responsible for the first attachment of the virus to the cell receptor, modifications thereof may be utilized in altering its specificity to different host cells.

Fusion proteins encoded by recombinant vectors comprising the nucleotide sequences of the invention or other sequences, preferably, other therapeutic sequences, are also within the scope on the invention. Thus, a DNA sequence comprising at least one first nucleotide sequence selected from the nucleotide sequences substantially as shown in SEQ ID NO:6, SEQ ID NO:14, SEQ ID NO:22 (corresponding, receptively, to the structural proteins PB, hexon and fiber proteins) and at least one second nucleotide sequence operably linked thereto and selected from the nucleotide sequences shown in SEQ ID NO:4, SEQ ID NO:8, SEQ ID NO:10, SEQ ID NO:12 and SEQ ID NO:20 which function as structural stabilizers, may be constructed.

In any case, the DNA sequences of the invention are genomic DNA or cDNA.

In a second aspect, the invention relates to vectors capable of delivering into a host cell an exogenous nucleotide sequence of interest which is operably linked to the vector. The vector comprises the nucleotide sequence of the invention or deletions, insertions, mutations, replacements or modifications thereof or functional fragments thereof. Such delivery means any infection or transfection of the exogenous nucleotide sequence into a specific host cell, preferably resulting in recombinant integration of the foreign DNA into the DNA genome of the host cell.

In addition, the invention relates to DNA constructs comprising a vector of the invention, which, as defined, contains the DNA sequence of the invention or deletions, insertions, mutations, replacements or modifications thereof, and further comprising at least one therapeutic exogenous nucleotide sequence operably linked thereto. The exogenous nucleotide sequence preferably is inserted into the vector in a reading frame, to enable the expression thereof, in a host. The exogenous sequence may be present in only one copy. However, several copies of the exogenous sequence, or its combination with other therapeutic foreign sequences may be inserted. Such sequences may be separated by initiation and termination sequences or they may form a single reading frame, thus producing a single "fusion protein".

The DNA construct of the invention is a viral construct capable of infecting a host cell, upon exposure thereto, with the therapeutic exogenous nucleotide sequence which, under normal conditions, is not made or contained in the host cell or is made or contained in said cell in a defective form. Delivery into cells of linear DNA, by infecting the cells with constructs of the invention comprising such linear DNA, may be advantageous for recombination, i.e. integration into the cellular genome for stable expression.

The viral constructs of the invention which are in fact recombinant viruses, will comprise the essential features for infecting the desired host cell, and nevertheless be non-virulent.

Obviously, the viral constructs can also be modified with specific receptors or ligands to alter target specificity through receptor mediated events. Alternatively, a modified, selective targeting of the constructs is possible by producing a DNA construct according to the invention containing a modified fiber protein. It is known that alterations at the nucleotide level, i.e. mutations, insertions, or deletions or modifications at the protein level, may alter the specificity of the protein. For example, it has been shown [Stevenson S. C. et al. Virology 71(6):4782–4790 (1997)] that exchanging the head domain for other serotypes which recognize a different receptor, changes the specificity of the expressed Ad fiber protein. Furthermore, Michael S. I. [Michael S. I. et al. Gene Therapy 2:660–668 (1995)] described a new cell specificity in the Ad's binding obtained by genetic fusion of a peptide ligand to the carboxyl terminal of the Ad fiber protein. At the 3' end of the coding region of the Ad5 fiber gene, a coding region of a physiological ligand, the terminal decapeptide of the gastrin releasing peptide (GRP), was introduced, resulting in the expression of a fusion fiber-GRP protein product with a different specificity.

Other additional features which can be added to the vectors may ensure its safety and/or enhance its therapeutic efficacy. Such features include, for example, markers that can be used for selection, features that limit expression to particular cell types, such as promoters and regulatory elements that are specific for the desired cell type.

According to one embodiment of the invention, the therapeutic exogenous nucleotide sequence within the DNA construct of the invention is a sequence which either encodes a therapeutic exogenous protein or peptide product or is itself a therapeutic product or encodes a therapeutic RNA, or comprises a vector comprising exogenous DNA encoding a therapeutic exogenous protein or peptide product or a therapeutic RNA.

More specifically, the exogenous nucleotide sequence within the DNA construct of the invention is a sequence which encodes a therapeutic protein or peptide product which is not made or contained in said cell, or is a nucleotide sequence which encodes a therapeutic protein or peptide product which is made or contained in said cell in abnormally low amount, or is a nucleotide sequence which encodes a therapeutic protein or peptide product which is made or contained in said cell in defective form or is a nucleotide sequence which encodes a therapeutic protein or peptide product which is made or contained in said cell in physiologically abnormal or normal amount, or encodes a therapeutic RNA.

Preferably, the therapeutic protein or peptide product encoded by the exogenous nucleotide sequence is an enzyme, a receptor, a structural protein, a regulatory protein or a hormone which may be a naturally occurring or recombinant protein or peptide product or a modified protein or peptide.

Alternatively, the DNA constructs may comprise exogenous nucleotide sequences which are themselves therapeutic sequences. Such sequences do net necessarily encode a protein or peptide product, but act, for example, as regulatory elements which are not contained in the cell, are contained in the cell in defective form.

It is understood, that the constructs of the invention may be utilized in gene therapy in a manner known to those skilled in the art.

The host cell transfected with the DNA construct of the invention may be a mammalian cell.

In a second embodiment of the invention, the peptide or protein product encoded by the exogenous nucleotide sequence is a protein or peptide product capable of eliciting in an animal protective immunity against a specific antigen. The animal may be a human or a domesticated animal, preferably a bird.

When the domesticated animal is a bird, the antigen will preferably be a pathogen selected from Infectious Bursal Disease virus (IBDV), Newcastle Disease virus (NDV), Egg Drop Syndrome adenovirus (EDS), Infectious Bronchitis (IB), Marek Disease virus (MDV), Avian Influenza virus, fowl pox virus, chicken anemia virus (CAV), laryngo tracheitis virus, salmonella, coccidia or bacteria causing fowl cholera such as pasteurella or any other pathogen.

In a third aspect, the invention relates to a DNA construct for the expression of a protein or peptide product in a host cell, comprising an expression vector and at least one nucleotide sequence of the invention or functional equivalents and fragments thereof operably linked to the expression vector, the protein or peptide product being capable of eliciting in an animal protective immunity against HEV.

While with the DNA constructs described hereinbefore the transfection and/or expression vectors are comprised of the nucleotide sequence of the invention and the nucleotide sequence to be transferred into the host cell's genome is foreign, in the present DNA construct the vector, being an expression vector, is comprised of a foreign DNA sequence and the nucleotide sequence to be transfected is of HEV origin. Thus, the DNA construct disclosed in the third aspect of the invention is employed to transfect or infect a host cell with sequences encoded for antigens against HEV.

Within the same aspect, the preferred animal is a domesticated bird and the expression system is selected from the group consisting of fowlpox virus, vaccinia virus, Marek disease virus, baculovirus, bacteria, yeast and plant cells.

In a fourth aspect, the invention relates to a host cell transformed with a nucleotide sequence of the invention or transfected with any one of the DNA constructs of the invention. In one embodiment, the host cell is capable of expressing the therapeutic protein or peptide product encoded by the exogenous nucleotide sequence within the DNA construct, the protein or peptide product being capable of eliciting protective immunity against a specific antigen.

In a second embodiment, the host cell, transfected with the DNA construct of the invention, is capable of expressing a protein or peptide encoded by the exogenous nucleotide sequence within the DNA construct, which protein or peptide is capable of eliciting protective immunity against HEV.

The host cell may be a eukaryotic host cell, wherein said eukaryotic host cell is an insect cell, a plant cell, a mammalian cell, a bird cell, or a yeast cell, or a prokaryotic host cell such as a bacterial cell.

In yet a fifth aspect, the invention relates to a protein or peptide product expressed by the host cell of the invention, or by any other host cell transformed with the DNA sequence of the invention or transfected with the DNA construct of the invention.

The protein or peptide product may be a therapeutic protein or peptide product which is not made or contained in said cell, or is a therapeutic protein or peptide product which is made or contained in said cell in abnormally low amount, or is a therapeutic protein or peptide product which is made or contained in said cell in defective form or is a therapeutic protein or peptide product which is made or contained in said cell in physiologically abnormal amounts. Preferably, the protein or peptide product being an enzyme, a receptor, a structural protein, a regulatory protein or a hormone and may be a naturally occurring or recombinant protein or peptide product or a modified protein or peptide.

Alternatively, the protein or peptide product expressed by the host cell of the invention, or any other host cell as detailed above, may be such that is capable of eliciting in an animal protective immunity against a specific antigen, the animal being a human or a domesticated animal. Such peptides may also be employed as antigens in specific immunoassay tests (e.g. ELISA) or may be injected to produce antibodies for diagnostic purposes.

Further, the protein or peptide product may be a product encoded by the DNA sequence of the invention. In particular, the protein or peptide product may comprise a sequence substantially as shown in SEQ ID NO:3, SEQ ID NO:5, SEQ ID NO:9, SEQ ID NO:11, SEQ ID NO:13, SEQ ID NO:17, SEQ ID NO:19, SEQ ID NO:21, SEQ ID NO:23, SEQ ID NO:25, SEQ ID NO:27, SEQ ID NO:29, SEQ ID NO:31 or functional equivalents and fragments thereof provided that when said fragment is comprised within said SEQ ID NO:23, it does not correspond to the segment corresponding to SEQ ID NO:6 described in PCT/IL98/00609, incorporated herein by reference, or to derivatives thereof This sequence corresponds to the segment within SEQ ID NO:22, starting from amino acid 63 to amino acid 454.

The above sequences encode the following HEV proteins: 52K, IIIa, CPI, CPII, pVI, EP, 100K, pVIII, the complete fiber, Iva2, POL, pTP and DBP, respectively. In this case, the protein or peptide will be capable of eliciting in an animal protective immunity against HEV and the animal is a domesticated bird. Such peptides may be employed as antigens in specific immunoassay tests (e.g. ELISA) or may be injected to produce antibodies for diagnostic purposes (e.g. for the specific identification of HEV or anti-HEV antibodies).

Yet, in another aspect of the invention, a process for the production of transformed or transfected host cells of the invention is disclosed. The process comprising the steps of (a) transforming a host cell with the DNA sequence of the invention or transfecting a host cell with a DNA construct of the invention; (b) isolating the transformed or transfected cells obtained by step (a); and (c) culturing the host cell isolated in step (b) under conditions in which propagation of said cells takes place. Such steps may be conducted by any suitable method known to the man of the art The process itself may be used for ex vivo transfection in gene therapy.

A process for the production of a protein or peptide, is also within the scope of the invention. The process comprises the steps of (a) transforming a host cell with the nucleotide sequence of the invention or transfecting a host cell with a DNA construct of the invention; (b) culturing the cells obtained in (a) under conditions in which an expression of the protein takes place; and (b) isolating the expressed protein or peptide from the cell culture or/and the culture supernatant. Evidently, the suitable means to performs such steps are well know to the man of ordinary skill in the art [ThioFusion Expression Systems Version 1.1 Invitrogen Corporation San Diego, Calif. (1995); Pichia Expression Kit, Version 1.8, Invitrogen Corporation San Diego, Calif. (1995); and Pitcovski J. et. al. Avian Disease 40:75–761 (1996)].

The invention further relates to a vaccine for immunizing a domesticated animal against at least one specific antigen (hereinafter referred to as the first vaccine) which vaccine comprises an effective amount of the DNA construct of the invention or the protein or peptide of the invention, optionally further comprising pharmaceutically acceptable carriers, diluents and additives.

The term 'effective amount' for purposes herein is that determined by such considerations as are known in the art. The amount must be sufficient to alter the transformed cell's function or sufficient to stimulate the immune system and confer immunity against the specific antigen and preferably to confer immunity to progeny of the treated animal, via maternal antibodies.

By the terms carriers, diluents, adjuvants and vehicles it is meant any inert, non-toxic solid or liquid filler, diluent, or encapsulating material, not reacting with the active ingredient of the invention.

Up to date, different vaccines employing Ad origin vectors have been described [Karen F., et al., Current Opinion in Genetics and Development 3:499–503 (1993); Mason B. B. et al. Virol. 177:462–461 (1990); Fields Virology Vol 2. Fileds B. N. et al Eds. Lippincott-Raven publication; Prevec L. et al. The J. of Infectious Diseases 161:27–30 (1990); Xiang Z. Q. Virol. 219:220–227 (1996); Callebaut P. et al. J. of General Virol. 77:309–313 (1996)].

In yet another embodiment, the invention relates to a vaccine for immunizing an animal against HEV (hereinafter referred to as the second vaccine) comprising an immunologically effective amount of any one of the nucleotide sequences of the invention or any of the DNA constructs of the invention or any protein of the invention encoded by the DNA sequences of the invention, and optionally further comprising pharmaceutically acceptable carriers, diluents and other suitable additives. The DNA constructs according to this embodiment are (as elaborated hereinbefore) those constructed from a HEV nucleotide sequence to be expressed, operably linked to a foreign expression vector being capable of expressing the HEV sequence. The encoded protein or peptide product will then act as HEV antigen against which an immune system may be elicited.

Both types of vaccines according to the invention may be provided in various forms such as lysates of the cells of the invention, as partially or completely purified proteins of the invention, as the DNA constructs of the invention and is preferably a sub-unit type vaccine, nevertheless, not limited thereto.

The present invention also concerns with pharmaceutical compositions comprising as active ingredient a therapeutically effective amount of a DNA construct according to the invention, or of a cell according to the invention, or of a therapeutic protein or peptide product according to the invention. The pharmaceutical composition of the invention may also further comprise any suitable additive such as pharmaceutically acceptable carriers, diluents, adjuvants and vehicles.

The vaccines or compositions of the invention are administered and dosed in accordance with good veterinary practice, taking into account the clinical condition of the individual animal, the site and method of administration, scheduling of administration, the animal's age, body weight, diet and other factors, well know to the veterinary practitioner. The doses may be single doses or multiple doses and the treatment may be effected at any age from day one.

In addition, the invention relates to a method of providing a therapeutic exogenous nucleotide sequence to an animal in need of such sequence by administering to the animal a therapeutically effective amount of the DNA construct of the invention.

Furthermore, the invention relates to a method of providing a therapeutic protein or peptide product, to a patient in need of such product, by administering to the patient therapeutically effective amount of the DNA construct of the invention or a therapeutically effective amount of the transfected cells of the invention [for example, as described in a Clinical Protocol in Human Gene Therapy 5:501–519 (1994)].

Any conventional method for as administering the products of the invention (e.g. the DNA sequences, the DNA constructs, or the protein or peptide product of the invention), such as tablets, suspensions, solutions, emulsions, capsules, powders, syrups, and the like may be used, as long as the biological activity of the therapeutic ingredient thereof is retained.

Administration may be oral, subcutaneous or parenteral, including intravenous, intramuscular, intraperitoneal and intranassal administration as well as intrathecal and infusion techniques. Nevertheless, most preferred methods are oral administration and injection. Following injection the DNA construct of the invention will circulate until it recognizes the host cell with the appropriate target specificity for infection.

In addition, the invention relates to a method of immunizing an animal against a specific antigen by administering to said animal an effective immunizing amount of the first vaccine according to the invention, wherein the animal is preferably a human or a domesticated animal.

Alternatively, the invention relates to a method of immunizing a domesticated animal against HEV by administering to the animal an effective immunizing amount of the second vaccine according to the invention, which case, the animal is preferably a bird.

The invention also relates to the use of the nucleotide sequences of the invention, or the DNA constructs of the invention or the protein and peptide products of the invention in the preparation of a vaccine or of a pharmaceutical composition.

Finally, the invention relates to an antibody, either monoclonal, polyclonal or recombinant antibodies, directed against any one of the DNA sequences or the protein or peptide products of the invention. The antibodies may be produced by standard antibody production technology well known to those skilled in the are, as described generally [Harlow and Lane, Antibodies: A Laboratory Manual, Cold Spring Harbor Laboratory, Cold Spring Harbor N.Y. (1988); Borrebaeck et al. Antibody Engineering-A Practical Guide, W.H Freeman and Co. (1992)]. In addition, antibody fragments may be prepared from the antibodies by methods known in the art and will include the Fab, F(ab')$_2$ and Fv fragments. Evidently, such antibodies may be used in detecting the presence, in a biological sample, of the specific antigen against which they have been produced. Such methods are known to those skilled in the art and may include the ImmunoComb technology (to Orgenics).

The invention will now be described in an illustrative manner and it is to be understood that the terminology which will be used is intended to be in the nature of is the words of description rather than of limitation.

Obviously, many modifications and variations of the present invention are possible in light of the above teaching, it is therefore, to be understood that within the scope of the appended claims, the invention may be practiced otherwise than as specifically described.

EXAMPLES

Example 1 Isolation of HEV

Turkeys were exposed to the virulent field strain of HEV. Five days later, birds were sacrificed, and the spleens were removed. A TCN solution (10 mM Tris-HCl pH 7.2, 10 mM $CaCl_2$, 100 mM NaCl) twice the volume of the tissue was added to the spleens which were then ground and homogenized for 5 minutes (min.). The tissue homogenate was frozen and then thawed at −70° C. and at 37° C., respectively, for three times, followed by centrifugation at 8,000×g at 4° C., for 20 min. The supernatant was mixed with trichlorotrifluoroethane (1:3) and further centrifuged at 5,000×g at 4° C., for 30 min. The resulting supernatant was then collected and added on top of the following gradient: 12 ml of 46.2% (w/v) cesium chloride (CsCl) (density of 1.35 g/ml); 12 ml of 35% (w/v) CsCl (density of 1.24 g/ml); 6 ml of 1M sucrose. The gradient was centrifuged for 24 hours (hrs) at 85,000×g at 4° C., with SW28 rotor.

The virus was isolated from a white ring, formed between the two CsCl layers obtained after centrifugation. The virus band was collected, diluted in Tris EDTA (TE), and repelleted by centrifiugation at 96,000×g for 2 hrs. The pellet was collected, resuspended in distilled water and dialyzed against TE. The virus obtained was stored at −20° C.

Example 2

Isolation and Purification of HEV DNA

The virus obtained as described in Example 1, was incubated for 3 hrs in a solution containing 0.01M Tris, 0.01M NaCl, 0.01M EDTA, 0.5% SDS, and 50 mg/ml proteinase K. Following incubation, the DNA of HEV was electrophoresed on 0.8% agarose gel and was visualized by Ethidium Bromide, at the size of 26 kb.

The plasmids obtained were transformed into E. coli XL1-blue cells, and white colonies, that grew on Luria Bertani medium (LB) plates containing ampicillin (100 g/ml) and X-Gal (200 g/ml), were isolated.

Example 3

DNA Sequencing

HEV DNA was digested either by EcoRI or PstI restriction enzymes and the resulting restriction fragments were separated on agarose gel, purified and cloned into plasmid pBS SK(+) (Stratagene). Cloned DNA fragments which were longer than 3 kb, were digested by exonuclease III (Promega) to create a series of nested deletions. The initial sequence information was obtained by sequencing the cloned fragments, using two commercially available primers, corresponding to the 5' and 3' ends of the pBS multiple cloning site (universal primers, New England Biolabs). The sequencing was carried out using the Taq Dyeseoxy Terminator system and an ABI 373 automatic sequencing apparatus. Sequences of 350–500 bp were resolved in a typical sequencing run. Once the initial sequence information was obtained, the primer walking methodology was employed to complete the sequencing of each cloned fragment. Gaps between the separate contiges were bridged by PCR amplification of the viral DNA and a subsequent sequencing of the PCR products. When needed, as in the case of the genome terminus, the HEV genome was sequenced directly (i.e. without the need to clone the same into plasmids).

Sequence Assembly

The processing of the raw sequence data, in the form of ABI trace filed, and the assembly of the separated readings, first into contiges and then into complete genome, were done employing a sequence assembly program and other programs as detailed by Bonfield et al. [Bonfield J. K. et al. Nucleic Acid Res. 24:4992–4999 (1995)].

Both strands of the entire viral genome (referred to hereinafter as the rightward and leftward strands) were sequenced and each nucleotide was determined at least three times.

Example 4

Sequence Analysis

Sequence analysis was performed by means of Wisconsin Package Version 9.1 [The Univrsity of Wisconsin Genetics Computer Group software package (GCG), Madison, Wis.].

At first stage, a search for homology with sequences of other members of the Ad family was first conducted using the BLAST program, followed by a search, to obtain a higher degree of accuracy, conducted by means of the FASTA or TFASTA programs. Multiple sequence alignments were performed either by Pileup program [GCG package] or by ClustalX [Higgins D. G. & Sharp P. M. Gene 73:237–244 (1988)].

The coding regions in the HEV genome were identified by comparison of the sequence obtained with sequences, pooled from the GenBank, of human Ad 2 (Accession No. J01917), human Ad 12 (Accession No. U40839), human Ad's 40 (Accession No. L19443), egg drop syndrome (EDS, Accession No. Y09598), CELO (Accession No. (U46933), ovine Ad (Accession Nos U18755, U40837, U31557, U40839) and canine Ad (Accession No. U55001).

Identification of the ORF of the HEV DNA Sequence

The complete sequence and genome organization of HEV was established. The genome map is presented in SEQ ID NO. 1 and in FIG. 1 in which identified regions are indicated.

The Genome length of HEV consists of 26269 bp, thus being the smallest genome isolated and characterized among the Ad family members [Jucker M. T. et al. (1996) ibid]. The overall G+C content in the genome is 34.93%. The inverted terminal repeats (ITR) are 39 bp long. As regards to these parameters, (size of the genome, G+C content, ITR) HEV resembles ovine Ad, consisting of 29544 bp long genome, 33.6% G+C content and 46 bp in the inverted terminal repeats.

The location of HEV genes as found by the inventors is summarized in Table 1.

TABLE 1

Summary of ORF locations and features in the HEV genome (as compared to ovine Ad)

| Protein | SEQ ID NO (na and aa)* | ATG | Stop | No. of residues | Mol. wt |
|---------|------------------------|-----|------|-----------------|---------|
| L1      |                        |     |      |                 |         |
| 52K     | NO:2; NO:3             | 8569 | 9468 | 300 | 33800 |
| IIIa    | NO:4; NO:5             | 9461 | 10975 | 505 | 50293 |
| L2      |                        |     |      |     |       |
| PB      | NO:6; NO:7             | 11000 | 12343 | 448 | 50903 |
| CP I    | NO:8; NO:9             | 12346 | 12705 | 120 | 11134 |
| CP II   | NO:10; NO:11           | 12711 | 12884 | 58  | 6111  |
| L3      |                        |     |      |     |       |
| pVI     | NO:12; NO:13           | 12905 | 13597 | 231 | 24947 |
| Hexon   | NO:14; NO:15           | 13609 | 16326 | 906 | 101089 |
| EP      | NO:16; NO:17           | 16331 | 16972 | 214 | 25008 |
| L4      |                        |     |      |     |       |
| 100K    | NO:18; NO:19           | 18184 | 20223 | 680 | 78283 |
| pVIII   | NO:20; NO:21           | 20768 | 21367 | 200 | 21769 |
| E3      |                        | 21213 | 22115 | 300 |       |
| L5      |                        |     |      |     |       |
| Fiber   | NO:22; NO:23           | 22518 | 23879 | 454 | 48770 |
| IVa2    | NO:24; NO:25           | 3436 | 2336 | 367 | 41802 |
| E2B     |                        |     |      |     |       |
| POL     | NO:26; NO:27           | 6767 | 3432 | 1112 | 129160 |
| pTP     | NO:28; NO:29           | 8557 | 6767 | 597 | 70582 |
| E2A     |                        |     |      |     |       |
| DBP     | NO:30; NO:31           | 18012 | 16975 | 346 | 38910 |

*SEQ ID NO for the nucleotide sequence (na) and the amino acid sequence (aa)

Comparison of these sequences with known and new members of the Ad family (Table 2) enables to determine the degree of homology between such members. The comparison shown in Table 2 was obtained using the Gap program for global comparison which is part of the GCG version 9 software package. The gap opening penalty parameter of Gap was set to 6 and its gap extension penalty parameter to 2. The sequences of other Ad's were pooled from the GenBank (accession Nos. as described hereinbefore). Abbreviations are POL for DNA polymerase, pTP for precursor terminal protein, DBP for DNA binding protein and EP for endoproteinase. The percent of amino acid sequence identity (%id) and similarity (%s) is presented in table which exhibit the uniqueness of the HEV genome.

TABLE 2

Comparison of the amino acid sequences of HEV proteins, with Ad's of different species

| Virus | Ad2 | | EDS | | Ovine | | CELO | |
|-------|-----|-----|-----|-----|-------|-----|------|-----|
| Protein | % id | % s | % id | % s | % id | % s | % id | % s |
| 52K   | 23.4 | 35.5 | 27.1 | 34.9 | 25.6 | 34.4 | 28.7 | 40.4 |
| IIIa  | 31.2 | 40.9 | 34.2 | 43.7 | 32.3 | 44.3 | 30.8 | 41.2 |
| penton | 48.6 | 58.1 | 52.9 | 61.4 | 52.6 | 61.4 | 49.7 | 59.3 |
| PVI   | 29.9 | 38.4 | 37.3 | 45.0 | 37.3 | 45.6 | 41.0 | 49.7 |
| hexon | 52.8 | 59.4 | 53. | 62.3 | 55.9 | 63.3 | 54.7 | 62.0 |
| EP    | 44.2 | 53.8 | 44.8 | 55.7 | 41.0 | 52.5 | 50.7 | 59.5 |
| 100K  | 36.1 | 45.3 | 38.4 | 47.5 | 36.6 | 47.4 | 38.6 | 48.8 |
| PVIII | 23.1 | 33.7 | 30.1 | 37.7 | 29.3 | 35.4 | 24.8 | 33.4 |
| fiber | 25.7 | 33.6 | 30.1 | 37.6 | 29.3 | 35.4 | 24.8 | 33.4 |
| IVa2  | 33.3 | 44.3 | 35.3 | 46.5 | 36.9 | 46.2 | 36.7 | 46.9 |
| POL   | 41.1 | 52.9 | 43.7 | 54.9 | 44.8 | 54.5 | 42.0 | 53.7 |

TABLE 2-continued

Comparison of the amino acid sequences of HEV proteins, with Ad's of different species

| Virus | Ad2 | | EDS | | Ovine | | CELO | |
|---|---|---|---|---|---|---|---|---|
| Protein | % id | % s | % id | % s | % id | % s | % id | % s |
| pTP | 34.3 | 44.8 | 37.4 | 45.8 | 34.5 | 46.6 | 35.9 | 47.7 |
| DBP | 28.4 | 40.5 | 28.4 | 40.5 | 36.0 | 43.7 | 34.4 | 43.9 |

Characterization of the HEV Genome Regions in Comparison to Other Members of the Ad Family In general, a genome is characterized by two major areas, the early region and the Late region, according to the stage of translation thereof. Each region comprises sequences which, inter alia, encode for different products, as detailed, for example, in Table 1.

In an attempt to identify the content of each region, the inventors deduced the following information.

Early Region (E)

E1—In general, in human Ad's (as deduced from human Ad 5), the E1 region comprises E1A and E1B. E1A encodes two major proteins whereas E1B encodes two major proteins and later in infection three smaller proteins. E1A transactivates expression of E3, E4 and partially E2 [Shenk, T. & Flint, J. Adv. Cancer Res. 57:47–85 (1991)] and induced DNA synthesis and cell transformation [Bayley, S. T. & Myniryk, J. S. J. Oncol. 5:425–444 (1994)]. In addition, this region is plays a role in the stimulation of specific human gene expression of infected cells.

No functional homologous region to this E1 was identified in the corresponding location in the HEV genome. Some ORF's were identified in sites in which E1 genes are located in other Ad's genomes, however, these sequences are not similar to any E1 sequence or to unassigned ORF's in other aviadenoviruses.

E2—E2 region encompass E2A and E2B regions and is located in the genome from 18013 to 16976 and 8557 to 3432, respectively. The E2A region consists of a gene which encodes the DNA binding protein (DBP). The DBP is divided, in Ad2, into two clusters. The C-terminal cluster is involved in binding to the viral DNA and activating replication of the major late promoter. High identity levels were found in this cluster among the C-terminus of DBP's from various Ad's. DBP is located between the EP and 100K genes, on the complementary strand. The DBP size, in HEV, is 345 amino acids long which is smaller than in other Ad's (382, 387, 441 and 539 in Ova, EDS, CELO and Ad2, respectively). The sequence VFQCCNP of HEV DBP (amino acids 255 to 261, SEQ ID NO:32) was found to be conserved in Ad2, ES and Ova. The Ova has a charged motif, KKRK (amino acids 11 to 14, SEQ ID NO:41) which is used for nuclear localization and it seems the HEV DBP has a similar motif KKNK (amino acids 35 to 38, SEQ ID NO:42) which may have the same function. A motif comprising Leu 515, Pro 516 and Pro 526, that serves in the cooperative binding of the subunits is partially conserved in HEV and correspond to residues Leu 316, Pro 317, and Pro 323. this motif was completely conserved in EDS and is missing from CELO.

The E2B region contains a sequence which encodes essentially two functional proteins, a DNA Polymerase (POL) and a pre-terminal (pTP) protein.

The pTP primes the Ad DNA replication [Salas, M. Science 149:1108 (1965); Smart, J. E. & Stillman, B. W. J. Biol. Chem. 25:13499–13506 (1982); Stillman, B. W. et al. Cell 23:497–508 (1981)]. This protein is processed at two sites by viral protease to a mature terminal protein (TP), which takes place through two cleavages by viral endoproteinase and was shown to be conserved among the different serotypes of the Ad family [Webster A. et al. J. Virol. 71:6381–6389 (1997)]. in HEV, pTP consists of 597 residues. Two cleavage sites were identified, at residues 169 and 297, which is similar to the terminal protein of EDS (consisting of 581 amino acids and is cleaved at residues 156 and 265). A sequence similar to that reported as a nuclear localization signal in Ad2 (RLPVRRRRRRVP, residues 380–391, SEQ ID NO:33) and in EDS (TLPARTRRTRRP, residues 308–319, SEQ ID NO:34) was identified in HEV (SLPLIRRIRRPP, residues 341–352, SEQ ID NO:35).

E3—An ORE of 900 bp lays between the regions coding for HEV pIIIa and the fiber protein (nucleic acids 21214 to 22113in SEQ ID NO:1). This ORF bares only little similarity to one of the gene products of the predicted E3 of Ova [Vrati S. et al. (1996) ibid.]. E3 has been mapped to this region in most Ad's. Two short additional ORF's are found near this ORF, both have no similarity to any published Ad sequence (data not shown). One of the E3 products, E3gp19K, binds to MHC class I antigens in the endoplasmic reticulum and blocks the cytolysis of viral infected cells. Such an interaction is species specific [Hermiston, T. W. et. al. Virology 238:145–156 (1993)]. The size of E3 varies from 2.5 kb in human Ad to 1.0–1.5 kb in canine Ad [Dragulev, B. P. et. al., Virology 183:298–305 (1991)] and only 0.5 kb in mouse Ad [Raviprakash, K. S. et. al. L. Virol. 63:5455–5458 (1989)].

E4—In general, E4 region modulates viral gene expression and DNA replication and inhibits host cell protein synthesis by interacting with host cell systems [Leppard, K. N. et al. J. Gen. Virol. 78:2131–2138 (1997)]. E4 in human Ad has a sequence similar to that in bovine Ad however, a lower degree of similarity to other Ad's such as ovine Ad [Vrati, S. et. al. (1996) ibid.] and murine Ad [Ball, A. O. et al., Virology 180:257–265 (1991)] and a possible similarity to E4 in CELO [Weiss, R. S. et al. J. Virol. 71:1857–1770 (1997)]. Nevertheless, no homologous sequence to E4 was found in HEV genome.

Delayed Early Genes

In general, a pIX gene, known from other members of the Ad family to be located in this region, strengthen hexon-hexon interactions [Boulanger, P. et al. J. Gen. Virol. 44:783–800 (1979); Van Oostrum, J. & Burnet, R. M. J. Virol. 56:439–446 (1985)] and has transcriptional properties, such as stimulating the major late promotor [Lutz, P. & Kedinger, C. J. Virol. 70:1396–1405 (1996)].

No sequences homologous to pIX were found in any of the avian Ad's or in ovine Ad.

The IVa2 gene, also located in this region, was recently identified as a component which contributes to the activation of the major late promoter [Lutz, P. & Kedinger, C. (1996) ibid.], is shorter in HEV compared to other Ad's.

Late Region (L) Proteins

The identification of the genes in the ORF's of the late region were deduced by comparison to the genomes of EDS and adenovirus 2 (Ad2), pooled from the GenBank (accession numbers Y09598 and J01917, respectively). The comparison is depicted in FIG. 1.

L1—The L1 region comprises the genes which encodes the 52K protein and the IIIa protein. The IIIa protein is known to bridge between the hexon and the core proteins.

L2—The L2 region comprises the genes encoding the structural protein, penton base (PB) and core protein I and core protein II (CP I and CP II, repetitively).

The penton base is bound to hexon protein at each vertex of the icosahedral structure. It is the base for the fiber, and together they constitute the penton. In most human Ad's, a tripeptide sequence, Arg/Gly/Asp (RGD) was identified and reported ad the binding site of the virus to cellular integrin, causing thereby endocytosis of the virus by the cell [Mathias, P et al. J. Virol. 68:6811–6814 (1994)]. A corresponding sequence was not identified in HEV, as in other avian Ad's and ovine Ad. The fact that no RGD sequence was found on the penton base indicates that the penetration of this Ad differs from that described for human Ad.

The core protein I and II (CP I and CP II) genes are located between the coding genes of PB and pVI proteins. CP I was found to be rich in arginine (17%), proline (11%) and alanine (13%). The molecular weights of CPI and CPII (11 kDa and 6 kDa, respectively) are smaller than the corresponding proteins in human Ad2 (48 kDa and 18 kDa) but are similar in size to the corresponding proteins in CELO (20 kDa, 12 kDa and 9.5 kDa). The core of human Ad's are slightly different, consisting of four proteins, pV, pVII mu and teiminal protein wherein PV, pVII, seems to be the counterparts of CPI and CPII.

L3—The L3 region contains genes encoding the pVI protein, the hexon protein and the endoproteinase (EP).

The pVI nucleotide sequence of HEV is substantially of the same size as in other avian Ad's. Two cleavage sites for the viral endoporteinase wee identified on both ends of the protein. The sequence LRGGK (residues 24 to 28, SEQ ID NO:36) in the N-terminal resembles a conserved cleavage site [Freimuth, P. & Andreson, C. W. Virology 193:348–355 (1993)]. Cleavage at the C-terminal of the pVI protein, gave rise to a peptide of 11 amino acids (FIG. 2). Sequence alignment of this peptide exhibits partial homology to C-terminals of several other pVI proteins. This 11 amino acid peptide was shown to act as a cofactor of the viral protease [Mangel, W. F. et. al. J. Virol. 68:6811–6814 (1993)] by forming a disulfide bond with the protease via a conserved cysteine residue (FIG. 2). The conserved sequence of this peptide was proposed by Vrati et al. [Vrati, S. et. al. (1996) ibid.], and is GXXXXXRRY/RCF/Y (SEQ ID NO:37, in which Y/R and F/Y are denoted by X).

The hexon protein, being a monomer of the major outer capsid is important in the determination of the capsid diameter. The HEV hexon protein (97 kDa) was found to be similar in size to other Avian Ad's.

The gene encoding the HEV endoproteinase (EP) aligned with the amino Acid sequences of other Ad's (CELO, EDS, Ad12 and Ad2) is depicted in FIG. 3 which shows that the HEV EP has 9 additional amino acid residues at the C-termiinal thereof When comparing with the active site of the viral EP of Ad2 which comprises amino acids His54, Glu71 and Cys122, the Glu71 residue is replaced in other Ad's by a similar amino acid, the aspartic acid (FIG. 3). In addition, these three amino acids are surrounded by a highly conserved region which probably forms the active cavity. In the process of the viral maturation, the EP cleaves several structural proteins. The cleavage site comprising the sequence (MLI)XGXG or (MLI)XGGX (SEQ ID NOS:38 and 39, respectively) as determined in other Ad's, was also identified in HEV EP, in a similar location. Table 3 shows that EP is one of the most conserved proteins of the Ad's L4—the L4 region comprises the genes encoding for the 100K protein and the pVIII protein. it seems the 100K protein is required for assembly of the hexon. Possibly, the 100K protein is required also for translation of the Viral RNA.

L5—the L5 region comprises the gene encoding another structural protein, the fiber protein consisting of a globular head, a shaft and a tail. The fiber protein plays an important role in the first attachment of the virus to the cell receptor, which is specific and with high affinity [Mei Y. F. & Wadell P. C. EMBO J. 11:751:760 (1992)]. All the elements described for the fiber protein of other Ad's were identified in HEV fiber (FIGS. 5A-1, 5A-2 and 5A-3).

Undefined ORF's

Eight ORF's encoding for putative polypeptides consisting of more than 100 amino acids were detected in the HEV genome. The relative location of these ORF's was found to correlate with the E1A, E1B and E4 regions identified in other Ad's. However, no functional homology was detected between these polypeptides and products encoded by these early regions, in other Ad's. Additional unidentified ORF's coding for shorter polypeptides, comprising only 50–100 amino acids, were found scattered throughout the HEV genome, 16 on one strand and 21 on the other strand.

Control Regions

Major late promoter—A TATA box for the major late promoter was identified starting at nucleotide 5384 (TTATATT). The ATG codon (+1) was found 30 nucleotides upstream. The CAAT sequence is located between nucleotides −81 to −78.

Stop codons—for several genes, as additional stop codon is present within 20 nucleotides downstream from the recognized stop codon (FIG. 6). It is possible that it is suggested that such additional stop codons ensure the accurate termination of translation.

Inverted Terminal Repeats—although relatively short, (39 bp), HEV ITR's include two conserved motifs identified in other Ad's (FIG. 4). Within the more conserved region, between nucleotides 9 to 18, only an arginine residue, at position 12, is missing from HEV (FIG. 4a). In human Ad, this Arg residue was found to be a part of a TAAT region which is involved in the initiation of DNA replication [Rawlins, D. R. et. al. Ann. Rev. Biochem. 60:39–71 (1984); Stillman, B. W. et. al. Cell 23:497–508 (1982)]. It has been suggested [Chen M. et al. J. Biol. Chem. 265: 18634–18642 (1990)] that a complex of two viral proteins (pTP and POL) bind to this sequence.

In addition, a GGGNGG region (nucleotides 26 to 31, SEQ ID NO:40), consisting part of a domain referred to in human Ad's as domain B (nucleotides 19 to 39) may correspond to the sequence reported as binding the SP1 transcription factor. An additional domain, referred to in human Ad's as domain C consists of nucleotides 40 to 51. Cellular factors bind to domains B and C to enhance the efficiency of the of the initiation of DNA replication. It seems that HEV consists of domain B however is missing domain C (FIG. 4b).

Table 2 exhibits ORF's of HEV, to which, when compared to other published Ad sequences, no homologues were found.

TABLE 2

ORF to which no homologous sequences were found in comparison to any other published adenovirus sequence

|      | START | STOP  | No. of residues | Mol. wt |
|------|-------|-------|-----------------|---------|
| ORF1 | 399   | 1139  | 246             | 27327   |
| ORF2 | 616   | 918   | 100             | 11220   |
| ORF3 | 1220  | 1951  | 243             | 26953   |
| ORF4 | 1497  | 1871  | 124             | 14495   |
| ORF5 | 4477  | 4974  | 166             |         |
| ORF6 | 17178 | 17537 | 120             | 14004   |
| ORF7 | 24509 | 24823 | 104             |         |
| ORF8 | 24847 | 25164 | 106             | 11902   |

Overlap—very short overlaps appear in the major genes. Only four of the unassigned ORF's seem to overlap with identified genes.

Example 6

Identification of Non-essential Regions in the DNA of HEV and Insertion of Foreign DNA Thereto Engineered virus vectors are developed, inter alia, for purposes of recombinant vaccination by way of expression of antigens from one or more pathogens, or for gene therapy (e.g. for the production of therapeutic proteins or peptides). In order to construct viral vectors, non-essential regions in the DNA sequence of the virus to be engineered must be identified. These sequences are then removed, to increase the capacity of the vector and enable the insertion of desired foreign DNA's.

Non-essential regions in the DNA sequence of HEV may be determined experimentally by adding foreign marker genes at particular sites and identification of viral replication and protein expression. In general, the genome of Ad's, as studied from the genome of Ad5, contains two regions frequently used for insertion of foreign DNA [Moss, B. et al. Vaccine 6:161–163 (1988)]. These are the early region 3 (E3), a lot of which can be deleted without interfering with the ability of the virus to replicate in cultured cells, and the early region 1 (E1), which is essential for viral replication in most human cell lines.

For high level expression of proteins of peptides, the most suitable vectors may be those containing substitutions in E1, with transcription driven by strong promoters. The construction of vectors of this type, in which transcription of inserts is under the control of an extra copy of the Ad major late promoter, has already been described.

Nonetheless, for use as vaccines, substitution of E3 sequences with genes encoding foreign proteins or peptide products such as specific antigens is likely to be the most promising approach since this results in vectors that can replicate both in most human cells in culture and in animals. Deletion of E3 sequences results in vectors with capacity of 4–5 kb inserts. Inserts in E3, in the left to right (E3 parallel) orientation are generally expressed as transcripts originating either from the E3 promoter, or from the major late promoter. Amounts of protein produced in cells infected with such vectors vary depending on the inserted gene but are almost invariably adequate to induce a good immune response in appropriate animals.

The construction of engineered Ad vectors, comprising a foreign gene, may be performed using standard techniques [Molecular Cloning, a laboratory manual, 2nd Eds., Sambrook, J.; Fritsch, E. F.; Maniatis, T. Cold Spring Harbor Laboratory Press (1989)]. For example, the foreign gene to be expressed is first inserted into a subgenomic viral DNA segment propagated in a suitable plasmid, for example, a bacterial plasmid. The resulting construct is 'rescued' into fill length infectious viral DNA by cotransfection into tissue culture cells with either a second viral DNA segment or a second plasmid, containing the rest of the viral genome plus the overlapping sequences required for homologous recombination. Identification of the desired viral recombinant is by plaque isolation and analysis of viral DNA structure by restriction and gel electrophoresis.

What is claimed is:

1. An isolated DNA sequence which comprises:

a) a nucleotide sequence as shown in SEQ ID NO:1; or b) a nucleotide sequence which corresponds to the sequence shown in SEQ ID NO:1 within the scope of the degeneracy of the genetic code.

2. The isolated DNA sequence as claimed in claim 1 which is genomic DNA or cDNA.

3. A non-virulent HEV encoded by the DNA sequence of claim 1.

4. A host cell transformed with a nucleotide sequence which comprises:

a) a nucleotide sequence as shown in SEQ ID NO:1; or b) a nucleotide sequence which corresponds to the sequence shown in SEQ ID NO:1 within the scope of the degeneracy of the genetic code.

5. A host cell as claimed in claim 4, said host cell being a eukaryotic host cell, wherein said eukaryotic host cell is an insect cell, a plant cell, a mammalian cell, a bird cell, or a yeast cell, or a prokaryotic host cell.

6. A process for the production of transformed or transfected host cells as claimed in claim 4, which process comprises:

a) transforming a host cell with a DNA sequence which comprises:

i) a nucleotide sequence as shown in SEQ ID NO:1; or ii) a nucleotide sequence which corresponds to the sequence shown in SEQ ID NO:1 within the scope of the degeneracy of the genetic code;

b) isolating the transformed or transfected cells obtained by step (a); and c) culturing the host cell isolated in step (b) under conditions in which propagation of said cells takes place.

7. A method of eliciting an immune response in an animal against Hemorrhagic enteritis virus (HEV) by administering to the animal the nucleotide sequence as claimed in claim 1.

8. The host cell of claim 5, wherein the prokaryotic host cell is a bacterial cell.

9. The pharmaceutical composition comprising as active ingredient a therapeutically effective amount of the cells of claim 4, and a pharmaceutically acceptable carrier.

* * * * *

SEQUENCE LISTING

```
<160> NUMBER OF SEQ ID NOS: 42

<210> SEQ ID NO 1
<211> LENGTH: 26270
<212> TYPE: DNA
<213> ORGANISM: hemorrhagic enteritis virus
<220> FEATURE:
<221> NAME/KEY: misc_feature
<222> LOCATION: (25290)..(25290)
<223> OTHER INFORMATION: N=Unknown

<400> SEQUENCE: 1
caatcaatat atataccgca tgcttgggag gggatttcgg cttgaaaagt gattttcttt      60
ttactgtact tttctttttg ttttctacat gtttcatttt ttgttttctg gttattttac     120
gtttaaattg tctaattgct tttaaaaagt tgatttgttc gttttctgtt tgaattgtgg     180
gcggttaaat tctgtgtcga tcttggtcat gtgtttcgga ttggcgctta aagcgctttc     240
atttcccgta aacggtgttg taattttcga gtcatcacaa ctgaccttgt cgtccgtgcg     300
gggtaagacc atggagtttc ccttttctgt tactcctgat agccctaagt ggccagtgaa     360
gcgaaaatgg gaagggatag aatgtggcta tataaagtat gggatacggg ctggagaata     420
```

-continued

```
ttctccggct ggtccaaggg ctgtgcgtta ccctcttcca ttttgatgaa atagatagag    480
agttggaatt tgattctcat gctttgaggt ctgttggaca aactgctgtt ttttcgcctg    540 gagattttc gtcagcattt ttcaaaaatc cttttgttat tgaattgcaa agtggtagat    600
tgcttgctgg tggagatgtc agatatgagt ctcttaccgc agaccacagg attgacattg    660
cagttgccat cagtgacgat ggaggactta cctggccaag gaagtcgttc gtgttacagt    720
ctaagccgga tgtcgagaat ggaatgttca tggatggatg tattttggag gctccttcgg    780
gagttgtgca cttgtttgcc gtgtactttg aaagtgcaaa ttataagtcc gttgtggacc    840
ctgaatatga ctttgtgcac gtcacgtctg aggatggcgg gatcacttgg agtgatatta    900
agtctctcaa gagcttgaag acgtcaaatg aagattattt ttttcaatgt ggcggcaatg    960
gcttagtaat gtcaaatgga acactggttg ttccttgtgt ttcgtggaag gatggatttc   1020
cacaatatag cactattatt tattcaacta atggagttga ctggacaaga cctcttatac   1080
taatactatc atcaatgact gtgtggactg tcaagtgtct gaaattgatg gagatttagt   1140
tagattagga agaaggccta ttacttattc tcctacaagt cctatagata atactttacg   1200 atttttttatt tcttctgata tgggcacaac ctgggaaacg cttcctgggg atagcacttt   1260
aaaagtttgg cttggcgttt catgttcttt agttaacgta cacacagttg ataatgtgaa   1320
tgtgttatta aatactgcaa tgtattatcg tgatgataat gacaaggcgt tgggtcttca   1380
aatgtttttg tatccacatg ctcagtggag gcctgttgga attgttgcta attctgtttt   1440
gactcggggt aatattgtgc aatctacgtc ttttggtaaa ttatttgttt tttctgatgt   1500
ttcagttaat cagggtagcg ctttgtcact ttatgatatt agtaggtatt ttcatgtgt   1560 atctactttg cctggatata atgttaattt gggttttcct gttactatcg aaggttctgc   1620
gaaacttcca tcaactagcc cgctcaagtt taggtatgat gggagatctt actggattgg   1680
gggatttctg gaacctagaa caggtggcac tttttctact tctcaacaag ttatgtttgc   1740
aattagaatt ggctggccaa tttttaatga tggtaatatt gttgctttg acaaacttc   1800 caatggtcaa ttgtatcctt ttttatttaa atatgaattt ttgtatggcg aattattttt   1860 ttcatgtttta gatacgtcta agttaactcc gtcactagct gcttgtactt cattatactt   1920
tcctgagagt agaattggac tattttgtta atttcttttca gaatgccttt cttctactta   1980
gttggtgctg gcagtgcata ttgtgagcgt tgtaaagaag tttgtgaaaa gagaaggaag   2040
aggtcaacaa caagaactac aagaactaaa agatctaaac cttctcacct tcaatatgtg   2100
cgttactatc ctggcacagt ggtttcctgt tggctgggat ggtactgata agcctgttac   2160
tgtcactaga attcctgact actggacgta cgacagagct gtttctagtc gtcaatctaa   2220
tactgtggtt cctgttaata cttctggaga aaatccaact gtggttgctg tgccgagact   2280
tttgcgaaaa aggaaagctt cagatatgtg aaaagtttga ataaaaattt tattaaattt   2340
catcatacat gcgttttgt ttttcttcca agtacctttt cttattttt aatttacata   2400 agtgaatgtt acagatttta tttacagagt ctagaagtaa actttgcata tctaaacata   2460
aaggtataat acttttccct ccctcgagta ttgctgacca ttgaaatgat tcccttgttg   2520
gacaagtatt aaacattaca aaagaatatt tcggatttttt ttcagataca atactgttta   2580
atagtatcgt tcgtacgtta gagtccattc ctcctgatcg attatgtaca aaattagata   2640
attgtagtgg ttggttttttt gtgcttaaaa tgtgtaattt ggcttgagtc ttcaagtcca   2700
taatattatt accgtttcct gataacggat ttacattatg taaaacaacg aacatataga   2760
```

-continued

```
atgcatgacc atatctacta gatagctttg atggtaaact acaatataat gggcttatat    2820
ttggtttctg tattaatttc tgcatacatt catctagaat tacgcatact ggcccttttt    2880
tggtatgaat attaaagata gaattttcgt tgttaacatc tagattctct ggggtaatga    2940
catcatcaaa agcacattct agaaaattaa tggtgaatac ctttgtggtt gggtaaaggg    3000
tattatcttg agcagaataa tttccttctt gtagttgagt tttccataat attacttcgt    3060
catatgaaat agttcctttt gtaggagtta tgaagatgat cgtttctggc attggttgta    3120
ttttttttgaa tcccagtaaa tttctaatta attggctttt cccgcaacct gtaggtccga    3180
ttactaaact aataagtgga tcagagttca tattgataga aggcagttca gagtttttag    3240
ttagatacat cttgttaatg ttgttaattt cgttgtattt cctcatattg cttctcaagt    3300
ctatattaga gttatagctt tcaaattctt taaatggcgg caaatcacat cctggtagta    3360
tgcttgagtt aatactgtct acagcagttt tccattgtcc aactacatcg tagaattctt    3420
caacttcatt attcatcttc gaattcctgt agtaagatag gatttgttat tctggggttt    3480
gggtggtaga gatcataagg aattaaagtg tttgtcttta gaaagtaaag ggttggatca    3540
ttccacggcc gtagttcgcg tattaattgt atttcatgaa cagaaaaggg ggagaatttt    3600
ccgtaagact tacataacgt tcttttcaaa gcagttcttt ctgtttggaa gatctcacca    3660
gattttaatt ctgaagtgtg gtagttgaag cattcttcca ggatttcaaa agttatgtct    3720
gcggtacagt gacccttttgc tcgtaatttt cctgttttttg aattttttgca ggtggtacac    3780
gtgatttctt taagggcgta cagctttgga gcgagaaaaa acttttttga agaatatgca    3840
ggtgaattac acaaattaca ccaagtttca cattctactg cccaaacaat tgaaggtttt    3900
ttaggatcaa atgttagttg tgaattttttg tttttaattc tatgttgtcc atattttaac    3960
atattttgat gtccttttttc tgtgagaaat agactgtctg tgtcaccgta gattgattta    4020
atggttttga attgaactgg tatactatct tcatcactgt ataggatttc gcgccactcg    4080
ctcataaagg ctcttgtcca cgctaatacg aagcttgcta gttgagttgg atatcttttg    4140
tttgtcggat gtaaattcgt tgattttaac atgtaaatag tgaggttttc tgatgtgacg    4200
tctaagatgt tgaatggttt gtaggttccc acgtgagcag tcgaagttga agtttgtgag    4260
gctgggcttt catccataaa ttctaaactg ttaaacggac tggtaagctc atcatccagt    4320
tctaaatttc tctctgcact gtcagttcgg ttttttaagg taaatgttaa attttctata    4380
ctaacatatg gaaggttgta agttggtaga gtagtaatgc tgtcaatggt tagttgtttg    4440
ttcaataatt gatttcttat tttaggattt tcttgaatgt ggttttcgaa aattgtaatg    4500
tcattgcttt ctcttgtagc aaaactaccg tatagtgcat tacttaggag tttgctgatt    4560
gctcttttaa caggatttttt ttcaacggtg cttttttctt ttgctagaat attttttagta    4620
acatattcta agcagcaagt gttccacgtt gggaatactg tgtttagctt gtggggaata    4680
atgtttactt tccatcctct attatggagt gtgataatat caattgaggt aacaatttca    4740
tttttcagta tttcgttcgt ccaacataat ttgccgcttt gtcttgaaca taatggcggt    4800
agaggatcaa gatgttctgg aggtggcggg atggcgtcaa tcattactac cattggcttt    4860
atatcagtaa aatatgatag ttttgtttta gtttttttta atttttcgtt taactttgta    4920
atttcattgt ttctttcttt ctctcctatt ggaaatccgt atggcattgg atgagttaga    4980
gcactagcat acatgccgca aatatcgtaa acaaaaattt tttctttgaa tattcctaag    5040
tgtgttgggt aacaacgtcc acctctaacg gactgacgga tgaaactgta catttcatca    5100
gatggtgcta ctatgtctgg cagggtggag gcttttgttc cattttgttt gaagtgtaac    5160
```

```
tgtctaaaaa tggcgtgaga attagatgaa atagtcggtc ttttaaaaat attaaaattg    5220
cattttaggt ttagttcctc tttgatgaat gtatcgaaag tatttaggag ggttttttgtt   5280 agttcttccg ttatttttaac gtctttaata caatagtcga ttaattcttt aacaatgtca   5340
tatttgactt ccttttttc taaccaaatt tcttttttgtt cgttatattc ttctttgcta   5400
gaccaatatt tttctgatgg aaacgagtct gagtctgtag ataatgaatt ggttgacatg    5460
tactcattta tagctttgaa cggacaacaa cctttgtgaa tttttaagtt gtatgctttg    5520
gccgcttctt ttagagaagt gtgtgttatt tggaaagtat ctctgaccat agacttgata   5580
tataaatttt ttatactttc tggatgtgga attccttctt taatctgtga aagtatttca   5640
cttttattat ttttttttttc ttctttagct acatagtagt ctgggttggg gaatttaatt   5700
gtaatatcgt taaaaagtat tctgccttgt cttggcataa aatttctttc aactgtgaaa   5760 agggagtga tgtctaggtt ttcgtcttga aggatttgtg ttgctaatag aatttcatcg    5820
aatgactgaa tgttgtgtcc gatgatgtaa aattctatga aaattggttt aactttcaga   5880
ctcattatga ggttagtatg ttcacttaaa ttgatatttg taattgattc taaattttgt    5940
gtttgagcga aatcttcgag aatttctcgg ttttctggtg ttaaaattaa ttttgtgaag   6000
taatctgtga gtgcaaatag gatgttattt cttaattttc tgaactccgt actaatgaag   6060
tttttaactt tagaaaacca gaagtacgta gaattttttg tttgaataga ttttattttg   6120
gctatttctg tttacagat attgataaga caatcatctc cgaaaattga aaagcatagt    6180
agaagaggat ttaataaaac tccagatgtt tcagctagtg taaatgtttc tatatcgtag   6240
ataaggaaga gttttttttgt gttttcattt tctcctatag gttgaaatgg tatagttttcc 6300 cagaattttc ttgtgtcatt gtctacgctg ttgtagtagt aagtagatct taagtcattg   6360
caggtatgaa ttgcggagta gattctacca catgagctgc attttgttg tttgagtccat   6420 gattttatcc agcataattt tgacttatca tatatgaagt ctaattcaat atattcatgc   6480
gatgttttga attcattttg gatcataaca catccagtta atttttttcca gatagttatt   6540 gatttgaccg gtaagttttt tacattttca atatcgctgt ttgtgggctt gtatttacta   6600
caaatgagga tatatgattg tgcatctttt actttttttg caagtttttt acaattaaat    6660
aaattatatg tccaagctat ttctattata gtggcttttta tgtctttttt acatatttgc   6720
aacctgtatg gaatttcgtt ttgagtggta taaatgtatt tgctcatctt ggttgtctta   6780
atcttctcat ttccttgtgtt cttacagccg aagcattgtt aattatttgt ctgtttgtag   6840
caattgttac aagaccaata ggcttgattt taaaggaaag agttactgtg ttgattaaat   6900
cttcattaag tctagcttgg tttagaaggt cgtttggatc tccagattct ggtctgtgtg   6960
atagggatgt aagtaggtct tcttgttctg cttgagtttc aatactatct ggccttctgt   7020
cacatattat tagaaggtca ttgatgattg ttctaaaatat tcttaaaaat ggagaaatgt    7080
ttgtgttagt ccaaactctg tgaaggttaa catttccttc atgatctcgt ccagtcatta   7140
tgacttggac atattgcata tttacatatc ttctgaaaat aacgtttaag tttaatagag   7200
catgataata aaatagtgta ctactgatgt gttcagctat gaaaaagtaa aatatgaatc   7260
ttcttataaa ctctctagtt acccttcctt gttcatttgc tctctgtaaa agattgtaaa   7320
ataactgacc gaaagaaaaa atttcatgtt ctcttgcagg ttctgttaat tctgctctta    7380
gttcattaag gatattttga aaaattcgaa ggatttcatt gcctaattct tcttccattt    7440
cttcttcttc aggtccggca cttggacctt ctcctgcatc ttcctcttcc acaggacttg   7500
```

```
gtggggtct  tcttattctt  ctgattaaag  gtaagctgtc  tataaacctc  gaaactatct   7560
gtcctctatt  tcttctcatt  tgttcagtta  tggctctttg  attttctctc  tgtcttaaaa   7620
atggtaagtc  tgttctagtg  ccacttctta  atcttgcacc  accttttaga  tttgttttcc   7680
actctttgaa  aggaaatatc  attgaattta  atgctgtgat  atatgataca  gcgtagttta   7740
tatccatttc  aggctgccat  ttgtcgtatt  ctgttttgag  gatttgaagc  caattatcct   7800
tcaacggtac  gtatatttt   tcatctttaa  attgccaatt  ataaataaat  tttgcaagta   7860
gttctaaagt  gtagttaatg  cactttaatg  tgttaatatc  tttttcagtt  tcatattgat   7920
acctttgatt  gaaagcaaaa  cttttggagt  taataaaatc  tcttaaattt  gttacgtaca   7980
tttttattat  ttcattttgg  atatttatat  tttcgtaagc  ttctggttgt  aatgtaacac   8040
ctgttccttg  catgttactt  ctagattcaa  tgtcagctct  aattctatta  ataagaattt   8100
cttcttgaaa  ctggtttaag  ttatcttcgt  agttttctgg  aatggtgcgc  acattacttg   8160
tgttaattgt  atatgaacaa  tcacttagaa  tagaccaaaa  atttctaggt  cttcttgtag   8220
tagattgatc  agcttcatag  tttaattttg  tatatgttct  gctttcaaaa  cggtagttat   8280
tgttcacatt  gaatagataa  gcgtagccaa  tcagcaaatg  aggaggcggc  aatccgttta   8340
aaggaggatt  taaaacggca  gggccttgtg  gtgctaaatt  ttctaacatt  aaaatctgat   8400
agttaaagaa  tgtactgcac  catcttaatc  caggaatact  tcttacaaac  ataggatgt    8460 tgacttgatc  tgtgaattgt  gttaaatgca  taaatctgat  ggtgtcttct  tcttggttag   8520
ttaggcgggc  ataattgtta  atctgaaaga  aagacatttg  tctttcagat  gaataccatt   8580
atgaaagcaa  tgcaaacaga  tagaggtaga  ctagaagcag  caacacccat  gtcttcaccg   8640
gctatttctg  gagaacctga  aagtccgtta  caacctttta  ctgagcaaat  ggagaaggaa   8700
gaatctaaag  tgcctcaaaa  taatcttttc  agggatggca  atgttaatga  acatttaaga   8760
gatattcgat  attatagtgg  aaaatctgtt  cagctagatg  gggatcaaaa  gctaaaaggt   8820
tcagactttg  gagaagacta  tccgtgtttt  tcaaaaggag  agaattttat  gaaagcagct   8880
aagttaaaaa  gagatgcaga  ttatactgaa  acttatgaag  tatctgctca  agatgcagat   8940
aataattttt  ataaggtcat  gttaatgaga  cctgaaacat  tatttggttt  gtattatttt   9000
gaaagtatca  taaagaacat  tatgagtgat  cctagtaata  ctgttttct   tagaaggttg   9060 tgtgctttgg  ctgttgaatg  gaatggaagg  ttaaaaggtt  tcataccgga  attgccagat   9120
gataggcatg  agtggttgag  agatttaatt  accctattag  ctgccatttg  taggtcatgt   9180
gttacggttg  atgaacaagt  ggcagctata  aacactagtc  tagtagaaat  ggcattaaat   9240
ttttcttctg  cagcttctgt  aataccttct  gcagctttag  gtgtacaaac  tagaagtatt   9300
ttgagttcta  tatgtaagga  aattttacaa  aatatgtgtc  aaattggagt  ttgtaaggat   9360
aattatcgac  cagctgtgca  atattatgca  gatcagcctg  gaatctcaca  tagtacatac   9420
ttttctagtt  tgagagacgt  tctacaatca  aacggaagaa  atgtcttcta  aggatgtggc   9480
agagatctta  tctggaaatg  ctcctagatt  gtcaaaggaa  tttagaaata  tgcccgtagc   9540
taataaaatg  attgagttgg  agaaagcaat  tgttcagcct  aaaaagacag  atactccaac   9600
catgctttct  ataattgtta  aacaattagt  tgatacaggg  gctatttcc   ctgaagaagc   9660 ttctgctgtt  tatagcaggt  tgttggacag  gcttgtaaag  tttaactcta  ttagaaatca   9720
taataactta  gaaggtcttg  ttaatgatat  acagcaaggg  cagaaaagtg  ttgtaatgtc   9780
taatcttaaa  gctaatagaa  acatgtctaa  tgttgttgta  ttacagaatt  tcttgcagca   9840
gctgccaaaa  actgtttcaa  aaggccagca  gaattatgac  tctttttaaag  gtttattgaa  9900
```

-continued

```
acagtttgtg attgattata atcaatttat agaagtttat aaatcaggtc cggatacatt      9960
tttacagtat aactttggtc cagctgtaca aaaaattaat ttaaatcaat cttttagaaa     10020
tttgtcaaat ttatggggag ctgttgtgcg atctgaagat gatattccat ctttgtcagc     10080
tttattagaa ccgcaaacga gatatttgtt gcttttactg tctcccatag ctatcgagca     10140
gtattttaca agagatagct ttgtatggta tatgttgaaa ctatataaaa ataccgttgc     10200
tcctccaatg agtactgagc cattagtaga gttgggtaat gttatagcta gtcttggacc     10260
gagttatgat caattaaagt tgcagcaagg attgaattat ttggtaacta accaaagaca     10320
agaatataaa ccatcagtac ctgacttgac taaagaagaa gaagcattac ttcgttattt     10380 tcaaactttta cttagaacaa aagttgctgg tacaacacgt cagttaagac agtcagattt     10440
agataatgtt attcaaaatg taaatcctgc tgctttccag ggcaatgtgg attttattaa     10500
taggcttttt gatttttta gtaaaatctt gaaataaat ccagatttt taactagaat       10560 agtttatgat tctcaatgga aactacctcc agctttcttt ttgaagtctg taattactcc     10620
tcaagatttg ttacaatttc ctcaacctaa aagaattcca gatcctaata tagttcaggt     10680
tcctgtttct aatgttactg ttccagttcc agcgcccagg actaaattta aaatgccaca     10740
acctgtgtcc aggccttcaa aaacagccta taggtctaaa tatcagtatc ctagtgaatc     10800
tgatacagat actgactcag aaattgaggt atttggtaag ccttacggac aataaaacc     10860 agctacaatc gacattgaca acttgtctgc tcaatttaaa agactgaaag gaagggttt      10920 agatatttct aattatatga gaagaaaagc aagaaatgtt aatgttagac catactgacc     10980
aattcctggt tcattttaga tggaatcttc gaacactgcc actagaattt ttgctccaac     11040
ggaagggaga acagtataa tttacagcaa cttgcctcct gttcaagata caaccaaaat      11100
attttatata gataacaagg ccattgatat agagtcatat aatcaagaga agatcattc      11160 taattattat actaatataa ttcaaacaca gaacatttca actattgatt caagtataca     11220
gcaaattcag ttagatgaaa ggtctagatg gggaggagaa ctacatacaa gcttagtaac     11280
atctgttatg aattgtacta acatttttaa ttcagataga tgtttagtga aaattcagac     11340
tattaagagt ccacctacat ttgaatggaa agaattgaaa atacctgagg gaaactatgt     11400
tttaaatgag tttattgatt tattaaatga aggtattact tctttatacc ttcagtatgg     11460
caggcaacag ggtgtacttg aagaagacat aggaataaaa tttgatactc gcaattttga     11520
aattggtaaa gatccaacta ctaatcttgt tactcctggt aaatacttgt ttaagggtta     11580
tcatgctgat ataatacttc ttcctggttg ggctattgat ttttctttt ctagattggg      11640 taacatttta ggtattagaa aacgtgagac ttataaagct ggcttttga ttgaatatga      11700 tgacttgaca aatggtaata ttccaccact gttggatgtt gctaactata agtctacaag     11760
tcaagctaaa ccattattac aggatccatc tggcagatct taccacgtta tggatagtga     11820
ttctaacaga cctgtgactg catataggtc ttttgttttg tcatataaca atgaaggtgc     11880
tgcaaaatta aagttttga tgtgtatgag tgatataacg gggggtctca atcagctgta      11940
ttggtgtttg cctgattctt ataaaccgcc agtatctttt aagcaagaaa cgcaagtaga     12000
taaactgcct gttgttggta tgcaactttt tccttttgtt tctaaatctg tgtattctgg     12060
tgctgctgtt tacacacagt taattgaaca gcagactaat ttgacacaaa ttttttaacag    12120 atttcatgat aatgaaattt taaaacaagc tccatatgtg aatcaagttt tattggctga    12180
aaatgtgccc ataaatgtta atcagggaac aataccaata ttttcaactc ttccaggagt    12240
```

```
acagagagtg gttgtggaag acgataggag aagaactgta ccctacgtta ccaagtcact   12300
tgctacagta tatccgaagg ttttgtctag caaaactttg caataatgca ttctgttgtt   12360
tattctccag gggacagtag aggatggggt attggtaatt caagtatgcg agattattat   12420
ttgataggtg gcgctttgca accgtctgat atttatactg ttagggttcg tgaacattgg   12480
agacgtaaaa ggaggccaac tgctcaaact ggaaattctg ctgtaacccc acgacgtaga   12540
agacggagaa caattgcaat tcaagtacca gctccaacta gagtactaag aaatagaata   12600
gttacacctg ttgtgcctgc agttcctgta cctgctccta cagtttctgc tgtaccagta   12660
cctgctgctc ctgtagctgt agctgctaag agacgtagag taggttagaa atgtttgaaa   12720
atttagcacc cagaaaaggt ctaaaaaccg aaacacggaa tgtaaagttt agtaatgaat   12780
tgagaggtgg ttttgttgtc tctgttttag ttccttttgct ttcttcttta ataggcgcag   12840
ctcctgccat tgctggaact gtaattgcag ctagaaattc taagtagtgt tttttcttac   12900
agatatgttt tcaaatttag ctccacgact tggacacaca tcatttttcaa ctgtatctgt   12960 tgggtctgct gaactgcgtg gaggaaagat taattgggge tctttaggtt cttccatttc   13020
aaatgcttta agaacaactg gcagatattt aggccagaaa gctactaaat ttgcaaatag   13080
taaaacattt agtgatatta aggccggtat tcaagatagt ggtttagtaa gaaatgtggc   13140
aggattagca ggtcaaacat tgaattcttt agtcgatatt ggaaggttta agttgaatc   13200 tgaacttcaa aaattaagag atagagtatt aaatacaatt ccagcagatc agttagctca   13260
aattttactg aactatcagc aaactcatga tcaggtgcct atgcctgtca caccaggtga   13320
tgctattcct ttaccaccac cacctccagc tgctattgaa cctagaaaac gtccttatgt   13380
tgaggaaata gacgataatc ctaacgatgc agaagtggtt attgacaccc ctgctttgtc   13440
tactgttcct gctatacctg cacctcctcc tactgttgct tttgtaccctt ctattaaacg   13500 tcctagaatt aggggaactg tgaatctga atggcaaact cacttgaata aaatgttggg   13560
tcagggtgtt agatttacct caacaaatca atgttattaa ttttttagat ggacatatca   13620
aatgctacgc caaaacttga tatattccac atagctggac cagatgcttc agaatatctt   13680
tcagaaaatc tcgttaattt catctccagt acagaatcgt attttccaat taataaaaaaa   13740 tttagagaaa caattgtagc accaacaaaa ggtgtgacga cagaacaatc tcagaaattg   13800
caagttaaaa ttgttccaac tttgacacaa gatttagaaa atagttttac tgctagattt   13860
actattgctg ttggcgatgg tcgggttttg gatatgggaa gtacgtattt tgatattagg   13920
ggtaacattg atcggggacc ttcatttaag ccatatggtg gtacagcata taatcctcta   13980
gctccaaggt cagctcaatt taataatatt aaaactgtgg gtggtaaaac atatttgact   14040
gctcaagcta ctaaattttt ttcaacatct ggaaatggtt gtgcagctgc taatactgaa   14100
gcaagttcat ttacaaattt agttccttca cctaatactg gttcagcaga agttctttt   14160 gatcctacaa cagagggagc tagttgcaga gctataacac ttggcagttc tgtaacagat   14220
gcaacttgtt atggagctta tacacctatt caaaatgcta atggttcaat tttacctcca   14280
tctgttacgc ctgataaaaa atttgccgat gctggtaaat ctggcagtgt tacatgtact   14340
gctgctattt gttgtgataa tgttactgta caatatccag atactagaat agttgcttat   14400
gactctactg ataaaatagc aactagaatg ggtaacagaa ttaattatat tggatttaga   14460
gataatttta taggttttgat gtattatgat aatggtgcac atagtggttc tttggctaca   14520
gaaacaggag atataaattt ggtagaacaa ttgcaagata gaaatacaga aattagttat   14580
caatatatgt tagcggattt gatgagtagg aatcattatt atagtcagtg gaatcaagct   14640
```

```
gtagatgatt atgatttaaa tgttagagta cttacaaata ttggttatga agagggtcct    14700
ccaggttact gttatccaag cacaggcatg ggcaactatc ctaatactgt catgtcggtt    14760
gggacattag tggataataa tggtacaact gctacaacaa cgtcaaatac tgtagctgtg    14820
atgggttttg gcagtgttcc tactatggaa attaacgttc aagcttattt gcaaaaatgt    14880
tggatgtatg ctaacattgc agaatattta cctgataagt ataaaaaagc tattcaaggt    14940
actagtgaaa ctgatccaac aacttatagt tatatgaata gtaggcttcc taatgtgaat    15000
atggctgatc tctttacaca tattggcggg cgttatagtt tggatgtaat ggataatgtt    15060
aatcctttta atcatcatag aaatagaggt ttgcaatata gaagtcaaat tttgggtaat    15120
ggtagaaatg tccgttttca tattcaggta cctcagaaat tttttgctat taagaatcta    15180
ttgttacttc ctggaactta tagttatgaa tggtggttca ggaaagatcc aaacttagta    15240
ctacagtcta cgttgggaaa tgatttaaga aaagatggag caagcattca gtttagcagt    15300
attagtcttt atgcgagttt ttttcctatg gatcacgcta cttgtagtga gcttatttta    15360
atgcttagaa acgatcaaaa tgatcaaact tttatggatt atatgggtgc aaagaataat    15420
ttgtatttag ttcctgctaa tcaaactaat gttcagattg aaataccttc tagagcttgg    15480
acagcattta gaggctggag ttttaaccga attaaaactg ctgagacacc agctgtgtgg    15540
tctacttatg atcttaattt taaatattct ggctcaatac cttatctaga tggtacattt    15600
tatctttctc acacttttaa ctctatgtct attttgtttg attcagcaat aacatggcca    15660
ggtaatgata gaatgttagt tccgaatttt tttgaaataa aagagagat agatacggag    15720 ggatacacta ctagtcagtc taatatgact aaagattggt atttgattca atgtctgca    15780 aattataacc agggtatca cggttatagt tttccagcag ataaagtata cagacagtat    15840
gattttatgt caaattttga ttctatgtct gttcaagtac cccggtcagg tctggcattt    15900
ttgtttaatg aaaattataa cttgatagta aataattcag gattttttgcc cagtaggacg    15960 gctccaattg ctggagttaa tgaaggccat cctatccag caaactggcc agcgccatta    16020
ataggtaata gtcctgatag tgttgttaca gttaggaaat tttttatgtga taagtatttta    16080 tggacaatac cttttttcaag caatttttatg aatatgggtg aattgactga ccttggacag    16140 agttttgctgt atactgagtc tgcacatagt ttgcaaataa catttaatgt tgatccaatg    16200
cctgagccta cgtacattta cttactttat agtgtttttg attgtgttag ggtcaatcaa    16260
cctaacaaaa attacttatc tgcagcttat ttcagaactc cttttgctac tggaactgct    16320
tcagtataaa atggctggaa cttcaagttc agaattgatt acattagtac gttctttagg    16380
tttgggttct tatttttttag gagtttatga taaacacttt cctggttttt taaatgatcg    16440
cagattagca tatgctattg taaatacggg tgattatatg tctggaggtt tacattggat    16500
agcttttgct tacgacccta atggtcgaaa attttacatt tttgatccat tggttggtc    16560 aaaaaaggag ctttggaagt tttacaagtt tcagtatgat agaattgtta agaacagc    16620 gttacagaat ggtagatgta ttaaattagt tagatctgta gatactgttc agtgtccttg    16680
ttctgctgca tgtggtttgt attgtgtgtt attttttagct tcatttttatt attttagaaa    16740 ttctcctatg tataataatc ctattattga tgttgttact ggcgtgccgc atagtaagat    16800
gaaatcttct tacggcatag ctatattaca ttgtaatcaa gaaagattgt ataactggct    16860
gtattacaac tctgtatatt ttcgagataa tgaattggaa ataaagagaa atacaagaat    16920
aaattctatt ttagttcatt atctctttat tgtattgttt ttatttgcgc gttaacaaaa    16980
```

-continued

| | | | | |
|---|---|---|---|---|
| agcgtcatca | tcactttcca | cctcgtgttg | agccacaata | gcttgcttaa aagaatgctt | 17040 |
| tttaggattg | aatacaaaag | caggcaacat | tattttagta | ggggagccat catctatggt | 17100 |
| ttccttcagc | ttagtatata | tatctttgct | aattttcata | gcctgtctca catcaatcat | 17160 |
| tgacaattta | aaatcacaat | gtttgtgagt | ctgattatct | ttatccttag catttctttt | 17220 |
| aagtctaatg | ggattgcaac | attgaaacac | aaggtgtgt | ttatacttgg cagttgcaag | 17280 |
| aagcatatca | tcatgacaac | tctcagggtc | tatgtcattc | gctccaggta tttcaaaagc | 17340 |
| agtcattttg | cagatttgtc | tgccaagctg | aatgttttca | tgaccatagt tacagaagca | 17400 |
| ctttgtaact | ataatcattt | tttcagaaat | ttcacatttc | tttgctttag gaaacatagc | 17460 |
| acttgtccaa | tcaatattat | gaagaaaggc | agcttttgct | ttttctttgt tgccaaaatt | 17520 |
| cattccacaa | gagtctggtg | aatgaatagt | tggccactga | acattactat ctaatggaca | 17580 |
| gactatattg | ctataatttg | ttagctttat | cacgtctttt | tgatttttt ctttctctaa | 17640 |
| tctgccctca | ccagctgtca | gagctctcat | tccttcctct | gattgaggag acaggctgta | 17700 |
| agttatgggt | tttgaaagca | taacagtgcc | atgaaaacat | ctaatgttat cttcatccca | 17760 |
| attatgaacc | cagatattgg | ctccaaggca | attataattg | caaattaagc cgctatcatt | 17820 |
| atacacaaaa | ctgcttacga | tacggccagc | aaagtgataa | aaagatttag cggaggaaat | 17880 |
| cgtaagatta | agatctggtt | tattcttctt | aacatatgtc | tcaaccagtt tggcccagta | 17940 |
| atcagaagta | ggtaaaatat | tcgcttcagc | ttggcatgca | aacaatgctt gtaatcctgt | 18000 |
| agcgtattgc | atagcttttt | ggtgacagtt | ttcaaattca | tcattttcca cccgctgtct | 18060 |
| cttaaggcaa | ggctcctcct | ctgagtctaa | aaaaattaa | atttattaca tttaaatgca | 18120 |
| aatagttttg | catacgattc | tgattggtct | tacttaccaa | ccaatgagcg ctggtcagaa | 18180 |
| gacatgatct | ataaaagagg | aaaagagaga | ggaaattcta | aaattataat ggcttcgtct | 18240 |
| gaggaggtcg | tagactctgc | agcgcaagaa | ttcaatgaac | ccttcccgcc agcaccagaa | 18300 |
| acattaccag | attcagaagt | tgatatagaa | cttatgaatc | gtgacttggg tgagtttgaa | 18360 |
| acaaattctt | ttagcatcca | cttaaggaga | caagcacaat | tgtgcaaatt ggctttacaa | 18420 |
| gctaaattca | aatatttacc | agaatctgta | gctgaaattg | gagatgcatt cgaatcattc | 18480 |
| attttttaatc | caattactga | atctgaccga | aaacaacaag | agcctagact caattttac | 18540 |
| cctccatttg | ctgtgccaga | acgaacagca | acttacaata | gctttttttca aattatgtct | 18600 |
| ctaccatttta | gctgcttagc | taacagatca | ggtagtaaaa | aatataagac tctaaaatca | 18660 |
| attacaaaat | ttgaagtctt | acccaagttt | gaatcagata | tgtttgtgat ttcagactgt | 18720 |
| cttgggtccg | aagtctcagc | aacagattct | ctgccaagga | aaacaaggtt ggttaattta | 18780 |
| caatctgata | acataagatt | aatgtccatg | aaagaaaaac | tgaagcatgt aactcaattt | 18840 |
| gcttatccag | ccttgaacat | tcctccaaaa | atttataaaa | ctctaattga dacactatat | 18900 |
| aaacctattc | aacagggaga | ggatgatgaa | tctgattatg | tgttttcaga tgatgatgtt | 18960 |
| agacaagtct | ttatttcaaa | tttagaggat | tttgaaaaat | ttactgatgg agagatagga | 19020 |
| gaattaacaa | attgtttcag | aaaaaacttg | cttcaggcaa | tacagtatgt gctacctta | 19080 |
| aaacttatgc | aaggtacttt | tagacatccg | tgctttgtaa | agaaattaca agagatgtta | 19140 |
| cattatactt | ttcatcatgg | ctatatcaag | ttaattagtt | ctattacggg ccacaatttg | 19200 |
| agtaaatata | taacttttca | ctgcatgaca | tatgagaata | acaataacaa tccaaatctt | 19260 |
| cacacaacat | tagatttgaa | tgatggtgaa | gattatatgg | ttgatacaat tttttatac | 19320 |
| ttgataatga | cttggcagac | tgcaatgggt | gtgtggcaac | aaaatatcaa tgagaagaat | 19380 |

```
ttagctagta tgaaagattt tttaactaaa aacggaccaa aattgatttt gtgtcgtgat   19440
tcagatagca tggctgatat gctagcagat tggataacag atggcggagt cttgcttcag   19500
atttttaggg atgctttacc agattttatg tcacagactc aattgaataa ctttagaaca   19560
tttattttag cgagaagtaa tatagtgagc tgtatggttt caacagtagt taaagatttt   19620
gtaccattag attttaaaga atctccacca caattgtggc cacatgttta ctgcttgaga   19680
ctgtcttatt ttttctacaa tcatggagat tatcaacaaa ttttttattg ggacgataat   19740
aaacctacag aaaatgaaat ttttгtгttat tgcaatcttt gtgctcctca tagaacacca   19800
atgctgaaca cagctttaca caatgaaatt ttagcaattg ggtcgtttga cttttttgtt   19860
ccaagtagtg atggtaaagg tggagaaaga gttacattaa ctccgggatt atgggctaat   19920
aaatttttga atcattttgt aagttctgaa tattttccat ttgaagttaa aaaatatgta   19980
gaccatccag aatgtttcaa aatacctcct acagcatgtg taattactaa gcctgagatt   20040
ttaagtagtt tgaaagagat aaagaagagg agagaaaagt ttttaattga aaaaggttct   20100
ggtatttatt tggatcctca aacgggagat aacttaagtg atgctaaaat tgtttcacag   20160
cccagaagag gcagcagtgg cggaaaaaca gaaaaagaag aaacggcaaa gaagaatccc   20220
aggtagttat tctaaatgga agcaatactg cacagatgta aaagaagcaa ttgcagttgt   20280
cggaagacag ccagtttgtg ttaagagata tctcacagca aagggcatac aaattccttc   20340
atcaaccatt aattattatg taaacaagtt tataagttgt gaagaagata gtaaattttc   20400
ctttttttaa tttataggcg agcccataca tgaaggaaca tatcaagaaa tattaaaact   20460
tagaaaagaa atttggatta ctgtgagaga cttaaaagat tatctatata ataatgagat   20520
aaacgaagaa attcatatac agaatagaac tttaaattct atcttagcta agcattctac   20580
atgttcagat ttaaatgcat tatttaagat gcatttggat gctaaggctt tacaatatca   20640
atatgagaaa aagctccgca ccatacctga taagaagtct cagaagaaaa agagatagct   20700
tctaccctga cagcaaattt tatagagaag acctccccta gtcacctgac caagcttggc   20760
gggcaatatg gatcccgttc cgttagaata tatttggcag tacaaccctg tgactggtag   20820
agttggagga gcaaatcaga attacggaca gaggattaat gttttgcata caaatcgtta   20880
cctctacaac agaatgcaga atgtgcagaa aaaagcaac gaaagagcca ctgaaagagg   20940
attactatct ctgaagggag gaagcacatt gccgactatt gcagaagatg aacctgccca   21000
gttgaactcg gctataгттc gcatggcagg attgaatgac ttgaacacgg ttcaagcacc   21060
ggattcatct aatctgcaaa acctggccaa cattgcactt gaagctgctg aacacaacaa   21120
agctacctca tctctcctaa caacgaagaa gттттgттgaa gaгтттccтc ctgttgttta   21180 cgaaaatcct ttttctggct ctaattttgc ttatgaattt aatcctctgt attcaccgtc   21240
cgggaatgag ttctccaatc ctccatttaa attcaccgga gгтgctaттa gcctcacagg   21300 acaacaccca gtcctctcgg gaggtgctgt tatcttatca ggacagaatc cggtactgga   21360
caaagcataa acatgagtgt caatctatta attgtatgac ggatgttgtt aatgtaatgg   21420

atcttgtttt tgattgtgat tatcctgagt ttaaatctgg aagcagtgtt atgttttctc   21480

atcgcttttc ttacttaaca gattgcaaaa ataaaacaat attaccgctt gttgatgaaa   21540

attgtgaatt aatgctagtt aatgatgaga tatgtgtagt tgtaaaatgt tactgtgatg   21600
aagaattttc agatcattgt cttactatta acttgaaatt aатgтgтасг ttagtaatga   21660 aattaataga tgggctttac ccattgccgc ttcgcctgc agatttacct gcttcagctt   21720
```

```
gtgttgcaac agcgctaaaa aatgagaaca agagagactt tttacataat agcttttgca   21780
ataaatgcag aataccagta ttgctttgct tatgtactga aaatgcttta acgaaggaag   21840
aatttatgca tcaattagtt aattttccat tatgtagtaa ctgttttaaa ggtaatagtg   21900
attgtagttg tgcattttat atctgtaagt tgtattcttt ttatcgaagc agagtttcct   21960
ccggtttagt taggaagaag ttaaatgatg ttaagaggtt agcatattta ggatcatgta   22020
acgttgatat gtgtattaac tgtggaagaa gtcttaagga ttgtttgtgt tctgaagctt   22080
atcagttatt atataagaaa tgcctttctt attgatagat tgtttacgaa gcagaagcag   22140
agtttctcct ccaatttagt aagattatta ttactgtgcc tagatattac tatgtgttca   22200
ggaagaagtt ttacggattg tctgtgctct tacaagaaat aaaaaatttg acatttactt   22260
acctgtctac ctggtcatgt attgatggga agagagtttc caaaattaag tctgagtttt   22320
ggatacagta tcgaattaac caatagagac acgtttgaca cagaagctgt gttgctgacg   22380
gtctatattc tgtttgtatt cctttttcca ttccatccac agaatcttca gatacagttt   22440
ggatgttttg tttaagtaaa ttctgattga tttctcttgg tttgcaacag gaacaacatt   22500
tgctgcattt attgcccatg gctactcctg gaaagcgttc tgcagaggaa ccagatcaac   22560
agaccttgaa aaagtcaaaa caatctgacc aaagtcaggg tttaaatcta gcatatcctt   22620
ttgataaaat aacagaattt gaagcaacac ctccctttat tcatgttggg caaggcttag   22680
acatatcaga tttatcgtta aatatgagaa ttggcaaagg attaaagttt gaaaatggta   22740
atctagttgt atcagatcaa cagtataatg ttacaccacc tttaattgca gatcagtcaa   22800
cattaggttt aaagtataat ccggatgttc tttctttaac acattcaggt gctttaactt   22860
tgccaactat tcaacatccc ctccaggctt cagctgaaa atttgaactt gctttgtcat   22920
caggttaaaa atctgatgat caaggtttaa ctttagattt ggatcctgta ttttctacag   22980
aatcatcaaa attttgctt aattgttcat tgccgttaga taagaatagt gacaagttaa   23040
cgttaaaatt tggtaatggt cttggattga ataatgacca gctagagaat actatgactt   23100
ataatcttcc tttaaaacgt gatggaacta atgttagtct ttcatttgga actaatttca   23160
aaatattgaa tgagatgtta gatttaaatc ttgtggcacc tatgtctaat tcagcaggag   23220
gattagcatt gcaatttaaa agccctttgt cagcagatga tggtatttta tcaattaaaa   23280
cagatacatc tttgggtata acaggaaata aattaggaat aagattggcc cctaacagtg   23340
gtctgcaaat aacaccaaat ggtctagcag ttagtgttaa tgctgtgcaa attctaagta   23400
gtcctttaat tactgcagcg tctataggcc caccaacaac aatggttact ggaacagtgt   23460
caccgggcag agcaacaaat ggtcaatttg taaccaaaac tgctaaagtt ttacgttata   23520
aatttgtgag atgggatgct ctgttaatca tacagtttat agataacata ggtgtaatag   23580
aaaaccctac cttttatcgt aacaaaagta ttgaattaag atctgctgat ttcttgagtc   23640
ctacgttaaa taatacatat atagtgccat tgaatggagg ggtaagggta gaatcaccta   23700
ctattcctgt acaattagaa gttatacttg aaaacaattc ctctttcatt caagtagggt   23760
ttgttaggtt aacagttaag aatggtaacc ctcatatgat tattcagtgt aatcctgtac   23820
ctgggaatat taaatgata aagataaaat ctgtaatgct ttttacttgt ttgataggct   23880
gatgaaataa actagtgatg caactttcgg ttttagtgac tcactttcga tttaaacacc   23940
tgcaggaagt ttttgctttc ttttttatcc tacatacggt tagaacgtta gattctcaca   24000
tatttgactt tgcaggtgcg cagagcggga aatttttatt ttgcatattt tttatttta   24060
tgtctggctt taaccacaac tcctttacga ttggctatta aaatgtcaag ttaagacaag   24120
```

-continued

```
tgtgaattttt ctcattagta atgctgtggc gcgaaacaca tatttttta tctaaagcct    24180
tcgagtaacc acaactttta tatgattggc tacttaagtt tcagttaggg taaatgtgaa    24240
gtttctcatg agaaatgcta tgccgccaaa aaaaaattta catcttgctg cagttcaaag    24300
ggtaaattct ttttccacta acatttcatg tctttcaagc gggaaaatgc ttggtcgagc    24360
caaagaactt aaatagttag tttgtggcca tggtttgaat gcttcactga ttaaatagac    24420
agattgctat tgagttagag cgggtaaaac tgagccaaga atctgagcgt gtagtataaa    24480
aaggactcac acttacacac ttacaatcat gcctctgact tggtggttgc aagctgacat    24540
tcacttcaat gaagatgacc aatttcagca gaacttaagt cttactcttc aagcaatggc    24600
tgagaacaaa gaagaaaaag actgtaaatt caacgtaact attcataagg aaattgaacc    24660
tgaattgaat actattttg atactcaaat ggatacctgg ttatcttgcg ctttactaa     24720
aatgactgtt ttttcaactg gtaaaggaga tatatttttg cgcatttat ttagaacttg     24780
tgctatacct tttttactgc tggagtggaa ggaagaaaat taaaatctaa aattgaacaa    24840
tcaatgtacg agacctttgg aagctgccta tctatggact ttattaaggt tgcttctgtt    24900
gctgtgcaag gctacgatct gcctgctatc aactgtaatg ttggaaaacc tctcgtgttg    24960
ctggtggcca cgcaagatga accgaatttt cgtgaaatac ctggaccata tcaaagat      25020
gtgtggatgc gtcactgtta cacaccaccg gaattaacgc ctgatgaaga tgatgacctt    25080
tgtacaccat tagccagtca tttctctat gatttgatc catcaattgt gcctgatatt     25140
gccttgttag acctttttga ataaaaata cttaaacaga aaatcgtgta atgtatttat     25200
tatgcgaaaa cagtaccata aggtaatgag tggtcttctc ctaccaaacg cacgtggtca    25260
aagaaattaa ctccattact tatacactgn aaaagcacac cacgcaagta cacaaggcca    25320
gtagtcaatg ttttccaagt catacagtgc aatccgacgc tctgtataaa cattaaccgt    25380
gttactcgaa atcaacatta ggccacttac catcaagcat gtagtcgaaa catgtaatgg    25440
aaatccgaga ctcatttcta gtgttacaac atcaaagtca tcggaacagt ttaccaaaaa    25500
ttatattcag aaaagtttaa atgtacccgt attttccaac atgatggatt catcgtcttc    25560
ggtctttaaa acatacacga accggagttg atgatggtgt aggcatcgtt tctcgcgagc    25620
ctgatgagaa cgggttcgta gaatgtactt ttggcacttg tattcttctg tcttctactt    25680
cattatcaga ttctccaaca tccatctaca acaaaaatgg agggtaaatt tttgccaact    25740
aatgcacaat aagctatgaa catcattatg acagatgcag taaatatgac ggtatattag    25800
tgagcggtta aaaagtatta tcattgcagc gtgtctgcct gctcttatct gtagattgtg    25860
ttttagaccg ggaggcattt tttccagtat taacagcgaa tgaatgtagt aaactacagg    25920
ttccggcatc ggaatcacga aaggcatcgg catttcaatt tcggcattca tgtcctataa    25980
aatacgattt aaaacatata tagtctctat acaacgttta aaggattgat ttgtgaaaaa    26040
aaagattata aagacttacg atttgagagg attgagaaga atttgaaaga actgccgcgg    26100
atcctgcttg tgattcttta aaatggcgat tatccgcctt cttttccggt tctctaacga    26160
acacgtgtcc taaagaggat gtcatcatat ttgaccatgt aatatcctgt tcaattttgt    26220
catctgaaag tcgaaatccc ctcccaagca tgcggtatat atattgattg              26270
```

<210> SEQ ID NO 2
<211> LENGTH: 900
<212> TYPE: DNA
<213> ORGANISM: hemorrhagic enteritis virus -continued

<400> SEQUENCE: 2

```
atgaatacca ttatgaaagc aatgcaaaca gatagaggta gactagaagc agcaacaccc     60
atgtcttcac cggctatttc tggagaacct gaaagtccgt tacaaccttt tactgagcaa    120
atggagaagg aagaatctaa agtgcctcaa aataatcttt tcagggatgg caatgttaat    180
gaacatttaa gagatattcg atattatagt ggaaaatctg ttcagctaga tggggatcaa    240
aagctaaaag gttcagactt tggagaagac tatccgtgtt tttcaaaagg agagaatttt    300
atgaaagcag ctaagttaaa aagagatgca gattatactg aaacttatga agtatctgct    360
caagatgcag ataataattt ttataaggtc atgttaatga gacctgaaac attatttggt    420
ttgtattatt ttgaaagtat cataaagaac attatgagtg atcctagtaa tactgttttt    480
cttagaaggt tgtgtgcttt ggctgttgaa tggaatggaa ggttaaaagg tttcataccg    540
gaattgccag atgataggca tgagtggttg agagatttaa ttaccctatt agctgccatt    600
tgtaggtcat gtgttacggt tgatgaacaa gtggcagcta taaacactag tctagtagaa    660
atggcattaa atttttcttc tgcagcttct gtaatacctt ctgcagcttt aggtgtacaa    720
actagaagta ttttgagttc tatatgtaag gaaattttac aaaatatgtg tcaaattgga    780
gtttgtaagg ataattatcg accagctgtg caatattatg cagatcagcc tggaatctca    840
catagtacat acttttctag tttgagagac gttctacaat caaacggaag aaatgtcttc    900
```

```
<210> SEQ ID NO 3
<211> LENGTH: 300
<212> TYPE: PRT
<213> ORGANISM: hemorrhagic enteritis virus

<400> SEQUENCE: 3

Met Asn Thr Ile Met Lys Ala Met Gln Thr Asp Arg Gly Arg Leu Glu
1               5                   10                  15

Ala Ala Thr Pro Met Ser Ser Pro Ala Ile Ser Gly Glu Pro Glu Ser
            20                  25                  30

Pro Leu Gln Pro Phe Thr Glu Gln Met Glu Lys Glu Glu Ser Lys Val
        35                  40                  45

Pro Gln Asn Asn Leu Phe Arg Asp Gly Asn Val Asn Glu His Leu Arg
    50                  55                  60

Asp Ile Arg Tyr Tyr Ser Gly Lys Ser Val Gln Leu Asp Gly Asp Gln
65                  70                  75                  80

Lys Leu Lys Gly Ser Asp Phe Gly Glu Asp Tyr Pro Cys Phe Ser Lys
                85                  90                  95

Gly Glu Asn Phe Met Lys Ala Ala Lys Leu Lys Arg Asp Ala Asp Tyr
            100                 105                 110

Thr Glu Thr Tyr Glu Val Ser Ala Gln Asp Ala Asp Asn Asn Phe Tyr
        115                 120                 125

Lys Val Met Leu Met Arg Pro Glu Thr Leu Phe Gly Leu Tyr Tyr Phe
    130                 135                 140

Glu Ser Ile Ile Lys Asn Ile Met Ser Asp Pro Ser Asn Thr Val Phe
145                 150                 155                 160

Leu Arg Arg Leu Cys Ala Leu Ala Val Glu Trp Asn Gly Arg Leu Lys
                165                 170                 175

Gly Phe Ile Pro Glu Leu Pro Asp Asp Arg His Glu Trp Leu Arg Asp
            180                 185                 190

Leu Ile Thr Leu Leu Ala Ala Ile Cys Arg Ser Cys Val Thr Val Asp
        195                 200                 205
```

-continued

```
Glu Gln Val Ala Ala Ile Asn Thr Ser Leu Val Glu Met Ala Leu Asn
    210                 215                 220

Phe Ser Ser Ala Ala Ser Val Ile Pro Ser Ala Ala Leu Gly Val Gln
225                 230                 235                 240

Thr Arg Ser Ile Leu Ser Ser Ile Cys Lys Glu Ile Leu Gln Asn Met
                245                 250                 255

Cys Gln Ile Gly Val Cys Lys Asp Asn Tyr Arg Pro Ala Val Gln Tyr
            260                 265                 270

Tyr Ala Asp Gln Pro Gly Ile Ser His Ser Thr Tyr Phe Ser Ser Leu
        275                 280                 285

Arg Asp Val Leu Gln Ser Asn Gly Arg Asn Val Phe
    290                 295                 300

<210> SEQ ID NO 4
<211> LENGTH: 1515
<212> TYPE: DNA
<213> ORGANISM: hemorrhagic enteritis virus

<400> SEQUENCE: 4
atgtcttcta aggatgtggc agagatctta tctggaaatg ctcctagatt gtcaaaggaa     60
tttagaaata tgcccgtagc taataaaatg attgagttgg agaaagcaat tgttcagcct    120
aaaaagacag atactccaac catgctttct ataattgtta aacaattagt tgatacaggg    180
gctattttcc ctgaagaagc ttctgctgtt tatagcaggt tgttggacag gcttgtaaag    240
tttaactcta ttagaaatca taataactta gaaggtcttg ttaatgatat acagcaaggg    300
cagaaaagtg ttgtaatgtc taatcttaaa gctaatagaa acatgtctaa tgttgttgta    360
ttacagaatt tcttgcagca gctgccaaaa actgtttcaa aaggccagca gaattatgac    420
tcttttaaag gtttattgaa acagtttgtg attgattata atcaatttat agaagtttat    480
aaatcaggtc cggatacatt tttacagtat aactttggtc cagctgtaca aaaaattaat    540
ttaaatcaat cttttagaaa tttgtcaaat ttatggggag ctgttgtgcg atctgaagat    600
gatattccat ctttgtcagc tttattagaa ccgcaaacga gatatttgtt gcttttactg    660
tctcccatag ctatcgagca gtattttaca agagatagct ttgtatggta tatgttgaaa    720
ctatataaaa ataccgttgc tcctccaatg agtactgagc cattagtaga gttgggtaat    780
gttatagcta gtcttggacc gagttatgat caattaaagt tgcagcaagg attgaattat    840
ttggtaacta accaaagaca agaatataaa ccatcagtac ctgacttgac taaagaagaa    900
gaagcattac ttcgttattt tcaaacttta cttagaacaa aagttgctgg tacaacacgt    960
cagttaagac agtcagattt agataatgtt attcaaaatg taaatcctgc tgctttccag   1020
ggcaatgtgg attttattaa taggcttttt gattttttta gtaaaatctt gaaaataaat   1080
ccagattttt taactagaat agtttatgat tctcaatgga aactacctcc agctttcttt   1140
ttgaagtctg taattactcc tcaagatttg ttacaatttc ctcaacctaa aagaattcca   1200
gatcctaata tagttcaggt tcctgtttct aatgttactg ttccagttcc agcgcccagg   1260
actaaattta aaatgccaca acctgtgtcc aggccttcaa aaacagccta taggtctaaa   1320
tatcagtatc ctagtgaatc tgatacagat actgactcag aaattgaggt atttggtaag   1380
ccttacggac caataaaacc agctacaatc gacattgaca acttgtctgc tcaatttaaa   1440
agactgaaag gaaagggttt agatatttct aattatatga gaagaaaagc aagaaatgtt   1500
aatgttagac catac                                                     1515
```

-continued

<210> SEQ ID NO 5
<211> LENGTH: 505
<212> TYPE: PRT
<213> ORGANISM: hemorrhagic enteritis virus

<400> SEQUENCE: 5

```
Met Ser Ser Lys Asp Val Ala Glu Ile Leu Ser Gly Asn Ala Pro Arg
1               5                   10                  15

Leu Ser Lys Glu Phe Arg Asn Met Pro Val Ala Asn Lys Met Ile Glu
            20                  25                  30

Leu Glu Lys Ala Ile Val Gln Pro Lys Lys Thr Asp Thr Pro Thr Met
        35                  40                  45

Leu Ser Ile Ile Val Lys Gln Leu Val Asp Thr Gly Ala Ile Phe Pro
    50                  55                  60

Glu Glu Ala Ser Ala Val Tyr Ser Arg Leu Leu Asp Arg Leu Val Lys
65                  70                  75                  80

Phe Asn Ser Ile Arg Asn His Asn Asn Leu Glu Gly Leu Val Asn Asp
                85                  90                  95

Ile Gln Gln Gly Gln Lys Ser Val Val Met Ser Asn Leu Lys Ala Asn
            100                 105                 110

Arg Asn Met Ser Asn Val Val Val Leu Gln Asn Phe Leu Gln Gln Leu
        115                 120                 125

Pro Lys Thr Val Ser Lys Gly Gln Gln Asn Tyr Asp Ser Phe Lys Gly
    130                 135                 140

Leu Leu Lys Gln Phe Val Ile Asp Tyr Asn Gln Phe Ile Glu Val Tyr
145                 150                 155                 160

Lys Ser Gly Pro Asp Thr Phe Leu Gln Tyr Asn Phe Gly Pro Ala Val
                165                 170                 175

Gln Lys Ile Asn Leu Asn Gln Ser Phe Arg Asn Leu Ser Asn Leu Trp
            180                 185                 190

Gly Ala Val Val Arg Ser Glu Asp Asp Ile Pro Ser Leu Ser Ala Leu
        195                 200                 205

Leu Glu Pro Gln Thr Arg Tyr Leu Leu Leu Leu Leu Ser Pro Ile Ala
    210                 215                 220

Ile Glu Gln Tyr Phe Thr Arg Asp Ser Phe Val Trp Tyr Met Leu Lys
225                 230                 235                 240

Leu Tyr Lys Asn Thr Val Ala Pro Pro Met Ser Thr Glu Pro Leu Val
                245                 250                 255

Glu Leu Gly Asn Val Ile Ala Ser Leu Gly Pro Ser Tyr Asp Gln Leu
            260                 265                 270

Lys Leu Gln Gln Gly Leu Asn Tyr Leu Val Thr Asn Gln Arg Gln Glu
        275                 280                 285

Tyr Lys Pro Ser Val Pro Asp Leu Thr Lys Glu Glu Glu Ala Leu Leu
    290                 295                 300

Arg Tyr Phe Gln Thr Leu Leu Arg Thr Lys Val Ala Gly Thr Thr Arg
305                 310                 315                 320

Gln Leu Arg Gln Ser Asp Leu Asp Asn Val Ile Gln Asn Val Asn Pro
                325                 330                 335

Ala Ala Phe Gln Gly Asn Val Asp Phe Ile Asn Arg Leu Phe Asp Phe
            340                 345                 350

Phe Ser Lys Ile Leu Lys Ile Asn Pro Asp Phe Leu Thr Arg Ile Val
        355                 360                 365

Tyr Asp Ser Gln Trp Lys Leu Pro Pro Ala Phe Phe Leu Lys Ser Val
    370                 375                 380
```

```
Ile Thr Pro Gln Asp Leu Leu Gln Phe Pro Gln Pro Lys Arg Ile Pro
385                 390                 395                 400

Asp Pro Asn Ile Val Gln Val Pro Val Ser Asn Val Thr Val Pro Val
                405                 410                 415

Pro Ala Pro Arg Thr Lys Phe Lys Met Pro Gln Pro Val Ser Arg Pro
                420                 425                 430

Ser Lys Thr Ala Tyr Arg Ser Lys Tyr Gln Tyr Pro Ser Glu Ser Asp
                435                 440                 445

Thr Asp Thr Asp Ser Glu Ile Glu Val Phe Gly Lys Pro Tyr Gly Pro
                450                 455                 460

Ile Lys Pro Ala Thr Ile Asp Ile Asp Asn Leu Ser Ala Gln Phe Lys
465                 470                 475                 480

Arg Leu Lys Gly Lys Gly Leu Asp Ile Ser Asn Tyr Met Arg Arg Lys
                485                 490                 495

Ala Arg Asn Val Asn Val Arg Pro Tyr
                500                 505

<210> SEQ ID NO 6
<211> LENGTH: 1344
<212> TYPE: DNA
<213> ORGANISM: hemorrhagic enteritis virus

<400> SEQUENCE: 6
atggaatctt cgaacactgc cactagaatt tttgctccaa cggaagggag aaacagtata      60
atttacagca acttgcctcc tgttcaagat acaaccaaaa tattttatat agataacaag     120
gccattgata tagagtcata taatcaagag aaagatcatt ctaattatta tactaatata     180
attcaaacac agaacatttc aactattgat tcaagtatac agcaaattca gttagatgaa     240
aggtctagat ggggaggaga actacataca agcttagtaa catctgttat gaattgtact     300
aaacatttta attcagatag atgtttagtg aaaattcaga ctattaagag tccacctaca     360
tttgaatgga agaattgaa atacctgag ggaaactatg ttttaaatga gtttattgat       420
ttattaaatg aaggtattac ttctttatac cttcagtatg caggcaaca gggtgtactt      480
gaagaagaca taggaataaa atttgatact cgcaattttg aaattggtaa agatccaact     540
actaatcttg ttactcctgg taaatacttg tttaagggtt atcatgctga tataatactt     600
cttcctggtt gggctattga ttttctttt tctagattgg gtaacatttt aggtattaga      660
aaacgtgaga cttataaagc tggcttttg attgaatatg atgacttgac aaatggtaat      720
attccaccac tgttggatgt tgctaactat aagtctacaa gtcaagctaa accattatta    780
caggatccat ctggcagatc ttaccacgtt atggatagtt attctaacag acctgtgact    840
gcatataggt cttttgtttt gtcatataac aatgaaggtg ctgcaaaatt aaagttttg     900
atgtgtatga gtgatataac gggggtctc aatcagctgt attggtgttt gcctgattct    960
tataaaccgc cagtatcttt taagcaagaa acgcaagtag ataaactgcc tgttgttggt   1020
atgcaacttt ttcctttttg ctttaaatct gtgtattctg gtgctgctgt ttacacacag   1080
ttaattgaac agcagactaa tttgacacaa attttaaca gatttcatga taatgaaatt    1140
ttaaaacaag ctccatatgt gaatcaagtt ttattggctg aaaatgtgcc cataaatgtt   1200
aatcagggaa caataccaat attttcaact cttccaggag tacagagagt ggttgtggaa   1260
gacgatagga gaagaactgt accctacgtt accaagtcac ttgctacagt atatccgaag   1320
gttttgtcta gcaaaacttt gcaa                                           1344
```

```
<210> SEQ ID NO 7
<211> LENGTH: 448
<212> TYPE: PRT
<213> ORGANISM: hemorrhagic enteritis virus

<400> SEQUENCE: 7

Met Glu Ser Ser Asn Thr Ala Thr Arg Ile Phe Ala Pro Thr Glu Gly
1               5                   10                  15

Arg Asn Ser Ile Ile Tyr Ser Asn Leu Pro Pro Val Gln Asp Thr Thr
                20                  25                  30

Lys Ile Phe Tyr Ile Asp Asn Lys Ala Ile Asp Ile Glu Ser Tyr Asn
            35                  40                  45

Gln Glu Lys Asp His Ser Asn Tyr Tyr Thr Asn Ile Ile Gln Thr Gln
        50                  55                  60

Asn Ile Ser Thr Ile Asp Ser Ser Ile Gln Gln Ile Gln Leu Asp Glu
65                  70                  75                  80

Arg Ser Arg Trp Gly Gly Glu Leu His Thr Ser Leu Val Thr Ser Val
                85                  90                  95

Met Asn Cys Thr Lys His Phe Asn Ser Asp Arg Cys Leu Val Lys Ile
                100                 105                 110

Gln Thr Ile Lys Ser Pro Pro Thr Phe Glu Trp Lys Glu Leu Lys Ile
            115                 120                 125

Pro Glu Gly Asn Tyr Val Leu Asn Glu Phe Ile Asp Leu Leu Asn Glu
        130                 135                 140

Gly Ile Thr Ser Leu Tyr Leu Gln Tyr Gly Arg Gln Gln Gly Val Leu
145                 150                 155                 160

Glu Glu Asp Ile Gly Ile Lys Phe Asp Thr Arg Asn Phe Glu Ile Gly
                165                 170                 175

Lys Asp Pro Thr Thr Asn Leu Val Thr Pro Gly Lys Tyr Leu Phe Lys
            180                 185                 190

Gly Tyr His Ala Asp Ile Ile Leu Leu Pro Gly Trp Ala Ile Asp Phe
        195                 200                 205

Ser Phe Ser Arg Leu Gly Asn Ile Leu Gly Ile Arg Lys Arg Glu Thr
210                 215                 220

Tyr Lys Ala Gly Phe Leu Ile Glu Tyr Asp Asp Leu Thr Asn Gly Asn
225                 230                 235                 240

Ile Pro Pro Leu Leu Asp Val Ala Asn Tyr Lys Ser Thr Ser Gln Ala
                245                 250                 255

Lys Pro Leu Leu Gln Asp Pro Ser Gly Arg Ser Tyr His Val Met Asp
            260                 265                 270

Ser Asp Ser Asn Arg Pro Val Thr Ala Tyr Arg Ser Phe Val Leu Ser
        275                 280                 285

Tyr Asn Asn Glu Gly Ala Ala Lys Leu Lys Phe Leu Met Cys Met Ser
290                 295                 300

Asp Ile Thr Gly Gly Leu Asn Gln Leu Tyr Trp Cys Leu Pro Asp Ser
305                 310                 315                 320

Tyr Lys Pro Pro Val Ser Phe Lys Gln Glu Thr Gln Val Asp Lys Leu
                325                 330                 335

Pro Val Val Gly Met Gln Leu Phe Pro Phe Val Phe Lys Ser Val Tyr
            340                 345                 350

Ser Gly Ala Ala Val Tyr Thr Gln Leu Ile Glu Gln Thr Asn Leu
        355                 360                 365

Thr Gln Ile Phe Asn Arg Phe His Asp Asn Glu Ile Leu Lys Gln Ala
370                 375                 380
```

```
Pro Tyr Val Asn Gln Val Leu Leu Ala Glu Asn Val Pro Ile Asn Val
385                 390                 395                 400

Asn Gln Gly Thr Ile Pro Ile Phe Ser Thr Leu Pro Gly Val Gln Arg
            405                 410                 415

Val Val Val Glu Asp Asp Arg Arg Thr Val Pro Tyr Val Thr Lys
        420                 425                 430

Ser Leu Ala Thr Val Tyr Pro Lys Val Leu Ser Ser Lys Thr Leu Gln
            435                 440                 445
```

<210> SEQ ID NO 8
<211> LENGTH: 360
<212> TYPE: DNA
<213> ORGANISM: hemorrhagic enteritis virus

<400> SEQUENCE: 8

```
atgcattctg ttgtttattc tccaggggac agtagaggat ggggtattgg taattcaagt      60
atgcgagatt attatttgat aggtggcgct ttgcaaccgt ctgatattta tactgttagg    120
gttcgtgaac attggagacg taaaaggagg ccaactgctc aaactggaaa ttctgctgta    180
accccacgac gtagaagacg gagaacaatt gcaattcaag taccagctcc aactagagta    240
ctaagaaata gaatagttac acctgttgtg cctgcagttc ctgtacctgc tcctacagtt    300
tctgctgtac cagtacctgc tgctcctgta gctgtagctg taagagacg tagagtaggt    360
```

<210> SEQ ID NO 9
<211> LENGTH: 120
<212> TYPE: PRT
<213> ORGANISM: hemorrhagic enteritis virus

<400> SEQUENCE: 9

```
Met His Ser Val Val Tyr Ser Pro Gly Asp Ser Arg Gly Trp Gly Ile
1               5                   10                  15

Gly Asn Ser Ser Met Arg Asp Tyr Tyr Leu Ile Gly Gly Ala Leu Gln
            20                  25                  30

Pro Ser Asp Ile Tyr Thr Val Arg Val Arg Glu His Trp Arg Arg Lys
        35                  40                  45

Arg Arg Pro Thr Ala Gln Thr Gly Asn Ser Ala Val Thr Pro Arg Arg
    50                  55                  60

Arg Arg Arg Arg Thr Ile Ala Ile Gln Val Pro Ala Pro Thr Arg Val
65                  70                  75                  80

Leu Arg Asn Arg Ile Val Thr Pro Val Val Pro Ala Val Pro Val Pro
                85                  90                  95

Ala Pro Thr Val Ser Ala Val Pro Val Pro Ala Ala Pro Val Ala Val
            100                 105                 110

Ala Ala Lys Arg Arg Arg Val Gly
        115                 120
```

<210> SEQ ID NO 10
<211> LENGTH: 174
<212> TYPE: DNA
<213> ORGANISM: hemorrhagic enteritis virus

<400> SEQUENCE: 10

```
atgtttgaaa atttagcacc cagaaaaggt ctaaaaaccg aaacacggaa tgtaaagttt      60
agtaatgaat tgagaggtgg ttttgttgtc tctgttttag ttcctttgct ttcttcttta    120
ataggcgcag ctcctgccat tgctggaact gtaattgcag ctagaaattc taag          174
```

<210> SEQ ID NO 11
<211> LENGTH: 58
<212> TYPE: PRT
<213> ORGANISM: hemorrhagic enteritis virus

<400> SEQUENCE: 11

Met Phe Glu Asn Leu Ala Pro Arg Lys Gly Leu Lys Thr Glu Thr Arg
1               5                   10                  15

Asn Val Lys Phe Ser Asn Glu Leu Arg Gly Gly Phe Val Val Ser Val
            20                  25                  30

Leu Val Pro Leu Leu Ser Ser Leu Ile Gly Ala Ala Pro Ala Ile Ala
        35                  40                  45

Gly Thr Val Ile Ala Ala Arg Asn Ser Lys
    50                  55

<210> SEQ ID NO 12
<211> LENGTH: 693
<212> TYPE: DNA
<213> ORGANISM: hemorrhagic enteritis virus

<400> SEQUENCE: 12
atgttttcaa atttagctcc acgacttgga cacacatcat tttcaactgt atctgttggg      60
tctgctgaac tgcgtggagg aaagattaat tggggctctt taggttcttc catttcaaat    120
gctttaagaa caactggcag atatttaggc cagaaagcta ctaaatttgc aaatagtaaa    180
acatttagtg atattaaggc cggtattcaa gatagtggtt tagtaagaaa tgtggcagga    240
ttagcaggtc aaacattgaa ttctttagtc gatattggaa ggtttaaagt tgaatctgaa    300
cttcaaaaat taagagatag agtattaaat acaattccag cagatcagtt agctcaaatt    360
ttactgaact atcagcaaac tcatgatcag gtgcctatgc ctgtcacacc aggtgatgct    420
attcctttac caccaccacc tccagctgct attgaaccta gaaaacgtcc ttatgttgag    480
gaaatagacg ataatcctaa cgatgcagaa gtggttattg acacccctgc tttgtctact    540
gttcctgcta tacctgcacc tcctcctact gttgcttttg taccttctat taaacgtcct    600
agaattaggg gaactggtga atctgaatgg caaactcact tgaataaaat gttgggtcag    660
ggtgttagat ttacctcaac aaatcaatgt tat                                  693

<210> SEQ ID NO 13
<211> LENGTH: 231
<212> TYPE: PRT
<213> ORGANISM: hemorrhagic enteritis virus

<400> SEQUENCE: 13

Met Phe Ser Asn Leu Ala Pro Arg Leu Gly His Thr Ser Phe Ser Thr
1               5                   10                  15

Val Ser Val Gly Ser Ala Glu Leu Arg Gly Gly Lys Ile Asn Trp Gly
            20                  25                  30

Ser Leu Gly Ser Ser Ile Ser Asn Ala Leu Arg Thr Thr Gly Arg Tyr
        35                  40                  45

Leu Gly Gln Lys Ala Thr Lys Phe Ala Asn Ser Lys Thr Phe Ser Asp
    50                  55                  60

Ile Lys Ala Gly Ile Gln Asp Ser Gly Leu Val Arg Asn Val Ala Gly
65                  70                  75                  80

Leu Ala Gly Gln Thr Leu Asn Ser Leu Val Asp Ile Gly Arg Phe Lys
                85                  90                  95

Val Glu Ser Glu Leu Gln Lys Leu Arg Asp Arg Val Leu Asn Thr Ile
            100                 105                 110

```
Pro Ala Asp Gln Leu Ala Gln Ile Leu Leu Asn Tyr Gln Gln Thr His
        115                 120                 125

Asp Gln Val Pro Met Pro Val Thr Pro Gly Asp Ala Ile Pro Leu Pro
    130                 135                 140

Pro Pro Pro Ala Ala Ile Glu Pro Arg Lys Arg Pro Tyr Val Glu
145             150                 155                 160

Glu Ile Asp Asp Asn Pro Asn Asp Ala Glu Val Val Ile Asp Thr Pro
                165                 170                 175

Ala Leu Ser Thr Val Pro Ala Ile Pro Ala Pro Pro Thr Val Ala
            180                 185                 190

Phe Val Pro Ser Ile Lys Arg Pro Arg Ile Arg Gly Thr Gly Glu Ser
        195                 200                 205

Glu Trp Gln Thr His Leu Asn Lys Met Leu Gly Gln Gly Val Arg Phe
    210                 215                 220

Thr Ser Thr Asn Gln Cys Tyr
225             230

<210> SEQ ID NO 14
<211> LENGTH: 2718
<212> TYPE: DNA
<213> ORGANISM: hemorrhagic enteritis virus

<400> SEQUENCE: 14
```

| | | | | | |
|---|---|---|---|---|---|
| atggacatat | caaatgctac | gccaaaactt | gatatattcc | acatagctgg | accagatgct     60 |
| tcagaatatc | tttcagaaaa | tctcgttaat | ttcatctcca | gtacagaatc | gtattttcca    120 |
| attaataaaa | aatttagaga | aacaattgta | gcaccaacaa | aggtgtgac | gacagaacaa    180 |
| tctcagaaat | tgcaagttaa | aattgttcca | actttgacac | aagatttaga | aaatagtttt    240 |
| actgctagat | ttactattgc | tgttggcgat | ggtcgggttt | tggatatggg | aagtacgtat    300 |
| tttgatatta | ggggtaacat | tgatcgggga | ccttcattta | agccatatgg | tggtacagca    360 |
| tataatcctc | tagctccaag | gtcagctcaa | tttaataata | ttaaaactgt | gggtggtaaa    420 |
| acatatttga | ctgctcaagc | tactaaattt | ttttcaacat | ctggaaatgg | ttgtgcagct    480 |
| gctaatactg | aagcaagttc | atttacaaat | ttagttcctt | cacctaatac | tggttcagca    540 |
| gaaagttctt | ttgatcctac | aacagaggga | gctagttgca | gagctataac | acttggcagt    600 |
| tctgtaacag | atgcaacttg | ttatggagct | tatacaccta | ttcaaaatgc | taatggttca    660 |
| attttacctc | catctgttac | gcctgataaa | aaatttgccg | atgctggtaa | atctggcagt    720 |
| gttacatgta | ctgctgctat | ttgttgtgat | aatgttactg | tacaatatcc | agatactaga    780 |
| atagttgctt | atgactctac | tgataaaata | gcaactagaa | tgggtaacag | aattaattat    840 |
| attggattta | gagataattt | tataggtttg | atgtattatg | ataatggtgc | acatagtggt    900 |
| tctttggcta | cagaaacagg | agatataaat | ttggtagaac | aattgcaaga | tagaaataca    960 |
| gaaattagtt | atcaatatat | gttagcggat | ttgatgagta | ggaatcatta | ttatagtcag   1020 |
| tggaatcaag | ctgtagatga | ttatgattta | aatgttagag | tacttacaaa | tattggttat   1080 |
| gaagagggtc | ctccaggtta | ctgttatcca | agcacaggca | tgggcaacta | tcctaatact   1140 |
| gtcatgtcgg | ttgggacatt | agtggataat | aatggtacaa | ctgctacaac | aacgtcaaat   1200 |
| actgtagctg | tgatgggttt | tggcagtgtt | cctactatgg | aaattaacgt | tcaagcttat   1260 |
| ttgcaaaaat | gttggatgta | tgctaacatt | gcagaatatt | tacctgataa | gtataaaaaa   1320 |
| gctattcaag | gtactagtga | aactgatcca | acaacttata | gttatatgaa | tagtaggctt   1380 |

-continued

```
cctaatgtga atatggctga tctctttaca catattggcg ggcgttatag tttggatgta    1440
atggataatg ttaatccttt taatcatcat agaaatagag gtttgcaata tagaagtcaa    1500
attttgggta atggtagaaa tgtccgtttt catattcagg tacctcagaa atttttttgct   1560 attaagaatc tattgttact tcctggaact tatagttatg aatggtggtt caggaaagat    1620
ccaaacttag tactacagtc tacgttggga atgatttaa gaaaagatgg agcaagcatt     1680
cagtttagca gtattagtct ttatgcgagt ttttttccta tggatcacgc tacttgtagt    1740
gagcttattt taatgcttag aaacgatcaa atgatcaaa cttttatgga ttatatgggt     1800
gcaaagaata atttgtattt agttcctgct aatcaaacta atgttcagat tgaaatacct    1860
tctagagctt ggacagcatt tagaggctgg agttttaacc gaattaaaac tgctgagaca    1920
ccagctgtgt ggtctactta tgatcttaat tttaaatatt ctggctcaat accttatcta    1980
gatggtacat tttatctttc tcacactttt aactctatgt ctattttgtt tgattcagca    2040
ataacatggc caggtaatga taaatgtta gttccgaatt tttttgaaat aaaaagagag     2100
atagatacgg agggatacac tactagtcag tctaatatga ctaaagattg gtatttgatt    2160
caaatgtctg caaattataa ccaggggtat cacggttata gttttccagc agataaagta    2220
tacagacagt atgattttat gtcaaattt gattctatgt ctgttcaagt accccggtca     2280
ggtctggcat ttttgtttaa tgaaaattat aacttgatag taaataattc aggattttg     2340 cccagtagga cggctccaat tgctggagtt aatgaaggcc atccttatcc agcaaactgg    2400
ccagcgccat taataggtaa tagtcctgat agtgttgtta cagttaggaa attttatgt     2460 gataagtatt tatggacaat acctttttca agcaatttta tgaatatggg tgaattgact    2520
gaccttggac agagtttgct gtatactgag tctgcacata gtttgcaaat aacatttaat    2580
gttgatccaa tgcctgagcc tacgtacatt tacttacttt atagtgtttt tgattgtgtt    2640
agggtcaatc aacctaacaa aaattactta tctgcagctt atttcagaac tccttttgct    2700
actggaactg cttcagta                                                   2718
```

<210> SEQ ID NO 15
<211> LENGTH: 906
<212> TYPE: PRT
<213> ORGANISM: hemorrhagic enteritis virus

<400> SEQUENCE: 15

```
Met Asp Ile Ser Asn Ala Thr Pro Lys Leu Asp Ile Phe His Ile Ala
1               5                   10                  15

Gly Pro Asp Ala Ser Glu Tyr Leu Ser Glu Asn Leu Val Asn Phe Ile
            20                  25                  30

Ser Ser Thr Glu Ser Tyr Phe Pro Ile Asn Lys Lys Phe Arg Glu Thr
        35                  40                  45

Ile Val Ala Pro Thr Lys Gly Val Thr Thr Glu Gln Ser Gln Lys Leu
    50                  55                  60

Gln Val Lys Ile Val Pro Thr Leu Thr Gln Asp Leu Glu Asn Ser Phe
65                  70                  75                  80

Thr Ala Arg Phe Thr Ile Ala Val Gly Asp Gly Arg Val Leu Asp Met
                85                  90                  95

Gly Ser Thr Tyr Phe Asp Ile Arg Gly Asn Ile Asp Arg Gly Pro Ser
            100                 105                 110

Phe Lys Pro Tyr Gly Gly Thr Ala Tyr Asn Pro Leu Ala Pro Arg Ser
        115                 120                 125

Ala Gln Phe Asn Asn Ile Lys Thr Val Gly Gly Lys Thr Tyr Leu Thr
```

-continued

```
            130                 135                 140
Ala Gln Ala Thr Lys Phe Phe Ser Thr Ser Gly Asn Gly Cys Ala Ala
145                 150                 155                 160

Ala Asn Thr Glu Ala Ser Ser Phe Thr Asn Leu Val Pro Ser Pro Asn
                165                 170                 175

Thr Gly Ser Ala Glu Ser Ser Phe Asp Pro Thr Thr Glu Gly Ala Ser
            180                 185                 190

Cys Arg Ala Ile Thr Leu Gly Ser Ser Val Thr Asp Ala Thr Cys Tyr
            195                 200                 205

Gly Ala Tyr Thr Pro Ile Gln Asn Ala Asn Gly Ser Ile Leu Pro Pro
            210                 215                 220

Ser Val Thr Pro Asp Lys Lys Phe Ala Asp Ala Gly Lys Ser Gly Ser
225                 230                 235                 240

Val Thr Cys Thr Ala Ala Ile Cys Cys Asp Asn Val Thr Val Gln Tyr
                245                 250                 255

Pro Asp Thr Arg Ile Val Ala Tyr Asp Ser Thr Asp Lys Ile Ala Thr
            260                 265                 270

Arg Met Gly Asn Arg Ile Asn Tyr Ile Gly Phe Arg Asp Asn Phe Ile
            275                 280                 285

Gly Leu Met Tyr Tyr Asp Asn Gly Ala His Ser Gly Ser Leu Ala Thr
            290                 295                 300

Glu Thr Gly Asp Ile Asn Leu Val Glu Gln Leu Gln Asp Arg Asn Thr
305                 310                 315                 320

Glu Ile Ser Tyr Gln Tyr Met Leu Ala Asp Leu Met Ser Arg Asn His
                325                 330                 335

Tyr Tyr Ser Gln Trp Asn Gln Ala Val Asp Asp Tyr Asp Leu Asn Val
            340                 345                 350

Arg Val Leu Thr Asn Ile Gly Tyr Glu Glu Gly Pro Pro Gly Tyr Cys
            355                 360                 365

Tyr Pro Ser Thr Gly Met Gly Asn Tyr Pro Asn Thr Val Met Ser Val
            370                 375                 380

Gly Thr Leu Val Asp Asn Asn Gly Thr Thr Ala Thr Thr Thr Ser Asn
385                 390                 395                 400

Thr Val Ala Val Met Gly Phe Gly Ser Val Pro Thr Met Glu Ile Asn
                405                 410                 415

Val Gln Ala Tyr Leu Gln Lys Cys Trp Met Tyr Ala Asn Ile Ala Glu
            420                 425                 430

Tyr Leu Pro Asp Lys Tyr Lys Lys Ala Ile Gln Gly Thr Ser Glu Thr
            435                 440                 445

Asp Pro Thr Thr Tyr Ser Tyr Met Asn Ser Arg Leu Pro Asn Val Asn
            450                 455                 460

Met Ala Asp Leu Phe Thr His Ile Gly Gly Arg Tyr Ser Leu Asp Val
465                 470                 475                 480

Met Asp Asn Val Asn Pro Phe Asn His His Arg Asn Arg Gly Leu Gln
                485                 490                 495

Tyr Arg Ser Gln Ile Leu Gly Asn Gly Arg Asn Val Arg Phe His Ile
            500                 505                 510

Gln Val Pro Gln Lys Phe Phe Ala Ile Lys Asn Leu Leu Leu Leu Pro
            515                 520                 525

Gly Thr Tyr Ser Tyr Glu Trp Trp Phe Arg Lys Asp Pro Asn Leu Val
            530                 535                 540

Leu Gln Ser Thr Leu Gly Asn Asp Leu Arg Lys Asp Gly Ala Ser Ile
545                 550                 555                 560
```

Gln Phe Ser Ser Ile Ser Leu Tyr Ala Ser Phe Phe Pro Met Asp His
                565                 570                 575

Ala Thr Cys Ser Glu Leu Ile Leu Met Leu Arg Asn Asp Gln Asn Asp
            580                 585                 590

Gln Thr Phe Met Asp Tyr Met Gly Ala Lys Asn Asn Leu Tyr Leu Val
        595                 600                 605

Pro Ala Asn Gln Thr Asn Val Gln Ile Glu Ile Pro Ser Arg Ala Trp
    610                 615                 620

Thr Ala Phe Arg Gly Trp Ser Phe Asn Arg Ile Lys Thr Ala Glu Thr
625                 630                 635                 640

Pro Ala Val Trp Ser Thr Tyr Asp Leu Asn Phe Lys Tyr Ser Gly Ser
                645                 650                 655

Ile Pro Tyr Leu Asp Gly Thr Phe Tyr Leu Ser His Thr Phe Asn Ser
            660                 665                 670

Met Ser Ile Leu Phe Asp Ser Ala Ile Thr Trp Pro Gly Asn Asp Arg
        675                 680                 685

Met Leu Val Pro Asn Phe Phe Glu Ile Lys Arg Glu Ile Asp Thr Glu
    690                 695                 700

Gly Tyr Thr Thr Ser Gln Ser Asn Met Thr Lys Asp Trp Tyr Leu Ile
705                 710                 715                 720

Gln Met Ser Ala Asn Tyr Asn Gln Gly Tyr His Gly Tyr Ser Phe Pro
                725                 730                 735

Ala Asp Lys Val Tyr Arg Gln Tyr Asp Phe Met Ser Asn Phe Asp Ser
            740                 745                 750

Met Ser Val Gln Val Pro Arg Ser Gly Leu Ala Phe Leu Phe Asn Glu
        755                 760                 765

Asn Tyr Asn Leu Ile Val Asn Asn Ser Gly Phe Leu Pro Ser Arg Thr
    770                 775                 780

Ala Pro Ile Ala Gly Val Asn Glu Gly His Pro Tyr Pro Ala Asn Trp
785                 790                 795                 800

Pro Ala Pro Leu Ile Gly Asn Ser Pro Asp Ser Val Val Thr Val Arg
                805                 810                 815

Lys Phe Leu Cys Asp Lys Tyr Leu Trp Thr Ile Pro Phe Ser Ser Asn
            820                 825                 830

Phe Met Asn Met Gly Glu Leu Thr Asp Leu Gly Gln Ser Leu Leu Tyr
        835                 840                 845

Thr Glu Ser Ala His Ser Leu Gln Ile Thr Phe Asn Val Asp Pro Met
    850                 855                 860

Pro Glu Pro Thr Tyr Ile Tyr Leu Leu Tyr Ser Val Phe Asp Cys Val
865                 870                 875                 880

Arg Val Asn Gln Pro Asn Lys Asn Tyr Leu Ser Ala Ala Tyr Phe Arg
                885                 890                 895

Thr Pro Phe Ala Thr Gly Thr Ala Ser Val
            900                 905

<210> SEQ ID NO 16
<211> LENGTH: 644
<212> TYPE: DNA
<213> ORGANISM: hemorrhagic enteritis virus

<400> SEQUENCE: 16
atggctggaa cttcaagttc agaattgatt acattagtac gttctttagg tttgggttct      60
tattttttag gagtttatga taaacacttt cctggttttt taaatgatcg cagattagca     120

-continued

```
tatgctattg taaatacggg tgattatatg tctggaggtt tacattggat agcttttgct    180
tacgacccta atggtcgaaa attttacatt tttgatccat ttggttggtc aaaaaaggag    240
ctttggaagt tttacaagtt tcagtatgat agaattgtta gaagaacagc gttacagaat    300
ggtagatgta ttaaattagt tagatctgta gatactgttc agtgtccttg ttctgctgca    360
tgtggtttgt attgtgtgtt atttttagct tcattttatt attttagaaa ttctcctatg    420
tataataatc ctattattga tgttgttact ggcgtgccgc atagtaagat gaaatcttct    480
tacggcatag ctatattaca ttgtaatcaa gaaagattgt ataactggct gtattacaac    540
tctgtatatt ttcgagataa tgaattggaa ataaagagaa atacaagaat aaattctatt    600
ttagttcatt atctctttat tgtattgttt ttatttgcgc gtta                     644
```

```
<210> SEQ ID NO 17
<211> LENGTH: 214
<212> TYPE: PRT
<213> ORGANISM: hemorrhagic enteritis virus

<400> SEQUENCE: 17

Met Ala Gly Thr Ser Ser Ser Glu Leu Ile Thr Leu Val Arg Ser Leu
1               5                   10                  15

Gly Leu Gly Ser Tyr Phe Leu Gly Val Tyr Asp Lys His Phe Pro Gly
            20                  25                  30

Phe Leu Asn Asp Arg Arg Leu Ala Tyr Ala Ile Val Asn Thr Gly Asp
        35                  40                  45

Tyr Met Ser Gly Gly Leu His Trp Ile Ala Phe Ala Tyr Asp Pro Asn
    50                  55                  60

Gly Arg Lys Phe Tyr Ile Phe Asp Pro Phe Gly Trp Ser Lys Lys Glu
65                  70                  75                  80

Leu Trp Lys Phe Tyr Lys Phe Gln Tyr Asp Arg Ile Val Arg Arg Thr
                85                  90                  95

Ala Leu Gln Asn Gly Arg Cys Ile Lys Leu Val Arg Ser Val Asp Thr
            100                 105                 110

Val Gln Cys Pro Cys Ser Ala Ala Cys Gly Leu Tyr Cys Val Leu Phe
        115                 120                 125

Leu Ala Ser Phe Tyr Tyr Phe Arg Asn Ser Pro Met Tyr Asn Asn Pro
    130                 135                 140

Ile Ile Asp Val Val Thr Gly Val Pro His Ser Lys Met Lys Ser Ser
145                 150                 155                 160

Tyr Gly Ile Ala Ile Leu His Cys Asn Gln Glu Arg Leu Tyr Asn Trp
                165                 170                 175

Leu Tyr Tyr Asn Ser Val Tyr Phe Arg Asp Asn Glu Leu Glu Ile Lys
            180                 185                 190

Arg Asn Thr Arg Ile Asn Ser Ile Leu Val His Tyr Leu Phe Ile Val
        195                 200                 205

Leu Phe Leu Phe Ala Arg
    210

<210> SEQ ID NO 18
<211> LENGTH: 2040
<212> TYPE: DNA
<213> ORGANISM: hemorrhagic enteritis virus

<400> SEQUENCE: 18
atgatctata aaagaggaaa agagagagga aattctaaaa ttataatggc ttcgtctgag     60
gaggtcgtag actctgcagc gcaagaattc aatgaaccct tcccgccagc accagaaaca    120
```

```
ttaccagatt cagaagttga tatagaactt atgaatcgtg acttgggtga gtttgaaaca      180
aattctttta gcatccactt aaggagacaa gcacaattgt gcaaattggc tttacaagct      240
aaattcaaat atttaccaga atctgtagct gaaattggag atgcattcga atcattcatt      300
tttaatccaa ttactgaatc tgaccgaaaa caacaagagc ctagactcaa tttttaccct      360
ccatttgctg tgccagaacg aacagcaact tacaatagct tttttcaaat tatgtctcta      420
ccatttagct gcttagctaa cagatcaggt agtaaaaaat ataagactct aaaatcaatt      480
acaaaatttg aagtcttacc caagtttgaa tcagatatgt ttgtgatttc agactgtctt      540
gggtccgaag tctcagcaac agattctctg ccaaggaaaa caaggttggt taatttacaa      600
tctgataaca taagattaat gtccatgaaa gaaaaactga agcatgtaac tcaatttgct      660
tatccagcct tgaacattcc tccaaaaatt tataaaactc taattgagac actatataaa      720
cctattcaac agggagagga tgatgaatct gattatgtgt tttcagatga tgatgttaga      780
caagtcttta tttcaaattt agaggatttt gaaaaattta ctgatggaga gataggagaa      840
ttaacaaatt gtttcagaaa aaacttgctt caggcaatac agtatgtgct acctttaaaa      900
cttatgcaag gtacttttag acatccgtgc tttgtaaaga aattacaaga gatgttacat      960
tatactttc atcatggcta tatcaagtta attagttcta ttacgggcca caatttgagt     1020
aaatatataa cttttcactg catgacatat gagaataaca ataacaatcc aaatcttcac     1080
acaacattag atttgaatga tggtgaagat tatatggttg atacaatttt tttatacttg     1140
ataatgactt ggcagactgc aatgggtgtg tggcaacaaa atatcaatga agaatttta      1200
gctagtatga aagatttttt aactaaaaac ggaccaaaat tgattttgtg tcgtgattca     1260
gatagcatgg ctgatatgct agcagattgg ataacagatg gcggagtctt gcttcagatt     1320
tttagggatg ctttaccaga ttttatgtca cagactcaat tgaataactt tagaacattt     1380
attttagcga gaagtaatat agtgagctgt atggtttcaa cagtagttaa agattttgta     1440
ccattagatt ttaaagaatc tccaccacaa ttgtggccac atgtttactg cttgagactg     1500
tcttatttt tctacaatca tggagattat caacaaattt tttattggga cgataataaa     1560
cctacagaaa atgaaatttt ttgttattgc aatctttgtg ctcctcatag aacaccaatg     1620
ctgaacacag ctttacacaa tgaaatttta gcaattgggc cgtttgactt ttttgttcca     1680
agtagtgatg gtaaaggtgg agaaagagtt acattaactc cgggattatg ggctaataaa     1740
tttttgaatc attttgtaag ttctgaatat tttccatttg aagttaaaaa atatgtagac     1800
catccagaat gtttcaaaat acctcctaca gcatgtgtaa ttactaagcc tgagatttta     1860
agtagtttga aagagataaa gaagaggaga gaaaagtttt taattgaaaa aggttctggt     1920
atttatttgg atcctcaaac gggagataac ttaagtgatg ctaaaattgt tcacagccc      1980
agaagaggca gcagtggcgg aaaaacagaa aagaagaaa cggcaaagaa gaatcccagg     2040
```

<210> SEQ ID NO 19
<211> LENGTH: 680
<212> TYPE: PRT
<213> ORGANISM: hemorrhagic enteritis virus

<400> SEQUENCE: 19

Met Ile Tyr Lys Arg Gly Lys Glu Arg Gly Asn Ser Lys Ile Ile Met
1               5                   10                  15

Ala Ser Ser Glu Glu Val Val Asp Ser Ala Ala Gln Glu Phe Asn Glu
            20                  25                  30

-continued

```
Pro Phe Pro Ala Pro Glu Thr Leu Pro Asp Ser Glu Val Asp Ile
         35                  40                  45

Glu Leu Met Asn Arg Asp Leu Gly Glu Phe Glu Thr Asn Ser Phe Ser
 50                  55                  60

Ile His Leu Arg Arg Gln Ala Gln Leu Cys Lys Leu Ala Leu Gln Ala
 65                  70                  75                  80

Lys Phe Lys Tyr Leu Pro Glu Ser Val Ala Glu Ile Gly Asp Ala Phe
                 85                  90                  95

Glu Ser Phe Ile Phe Asn Pro Ile Thr Glu Ser Asp Arg Lys Gln Gln
                100                 105                 110

Glu Pro Arg Leu Asn Phe Tyr Pro Pro Phe Ala Val Pro Glu Arg Thr
            115                 120                 125

Ala Thr Tyr Asn Ser Phe Phe Gln Ile Met Ser Leu Pro Phe Ser Cys
            130                 135                 140

Leu Ala Asn Arg Ser Gly Ser Lys Lys Tyr Lys Thr Leu Lys Ser Ile
145                 150                 155                 160

Thr Lys Phe Glu Val Leu Pro Lys Phe Glu Ser Asp Met Phe Val Ile
                165                 170                 175

Ser Asp Cys Leu Gly Ser Glu Val Ser Ala Thr Asp Ser Leu Pro Arg
            180                 185                 190

Lys Thr Arg Leu Val Asn Leu Gln Ser Asp Asn Ile Arg Leu Met Ser
            195                 200                 205

Met Lys Glu Lys Leu Lys His Val Thr Gln Phe Ala Tyr Pro Ala Leu
210                 215                 220

Asn Ile Pro Pro Lys Ile Tyr Lys Thr Leu Ile Glu Thr Leu Tyr Lys
225                 230                 235                 240

Pro Ile Gln Gln Gly Glu Asp Asp Glu Ser Asp Tyr Val Phe Ser Asp
            245                 250                 255

Asp Asp Val Arg Gln Val Phe Ile Ser Asn Leu Glu Asp Phe Glu Lys
            260                 265                 270

Phe Thr Asp Gly Glu Ile Gly Glu Leu Thr Asn Cys Phe Arg Lys Asn
            275                 280                 285

Leu Leu Gln Ala Ile Gln Tyr Val Leu Pro Leu Lys Leu Met Gln Gly
    290                 295                 300

Thr Phe Arg His Pro Cys Phe Val Lys Lys Leu Gln Glu Met Leu His
305                 310                 315                 320

Tyr Thr Phe His His Gly Tyr Ile Lys Leu Ile Ser Ser Ile Thr Gly
                325                 330                 335

His Asn Leu Ser Lys Tyr Ile Thr Phe His Cys Met Thr Tyr Glu Asn
            340                 345                 350

Asn Asn Asn Asn Pro Asn Leu His Thr Thr Leu Asp Leu Asn Asp Gly
            355                 360                 365

Glu Asp Tyr Met Val Asp Thr Ile Phe Leu Tyr Leu Ile Met Thr Trp
    370                 375                 380

Gln Thr Ala Met Gly Val Trp Gln Gln Asn Ile Asn Glu Lys Asn Leu
385                 390                 395                 400

Ala Ser Met Lys Asp Phe Leu Thr Lys Asn Gly Pro Lys Leu Ile Leu
                405                 410                 415

Cys Arg Asp Ser Asp Ser Met Ala Asp Met Leu Ala Asp Trp Ile Thr
            420                 425                 430

Asp Gly Gly Val Leu Leu Gln Ile Phe Arg Asp Ala Leu Pro Asp Phe
            435                 440                 445

Met Ser Gln Thr Gln Leu Asn Asn Phe Arg Thr Phe Ile Leu Ala Arg
```

| | | | | | | 450 | | | | | 455 | | | | | 460 | | |
|---|---|---|---|---|---|---|---|---|---|---|---|---|---|---|---|---|---|---|

Ser Asn Ile Val Ser Cys Met Val Ser Thr Val Lys Asp Phe Val
465 470 475 480

Pro Leu Asp Phe Lys Glu Ser Pro Pro Gln Leu Trp Pro His Val Tyr
485 490 495

Cys Leu Arg Leu Ser Tyr Phe Phe Tyr Asn His Gly Asp Tyr Gln Gln
500 505 510

Ile Phe Tyr Trp Asp Asp Asn Lys Pro Thr Glu Asn Glu Ile Phe Cys
515 520 525

Tyr Cys Asn Leu Cys Ala Pro His Arg Thr Pro Met Leu Asn Thr Ala
530 535 540

Leu His Asn Glu Ile Leu Ala Ile Gly Ser Phe Asp Phe Phe Val Pro
545 550 555 560

Ser Ser Asp Gly Lys Gly Gly Glu Arg Val Thr Leu Thr Pro Gly Leu
565 570 575

Trp Ala Asn Lys Phe Leu Asn His Phe Val Ser Ser Glu Tyr Phe Pro
580 585 590

Phe Glu Val Lys Lys Tyr Val Asp His Pro Glu Cys Phe Lys Ile Pro
595 600 605

Pro Thr Ala Cys Val Ile Thr Lys Pro Glu Ile Leu Ser Ser Leu Lys
610 615 620

Glu Ile Lys Lys Arg Arg Glu Lys Phe Leu Ile Glu Lys Gly Ser Gly
625 630 635 640

Ile Tyr Leu Asp Pro Gln Thr Gly Asp Asn Leu Ser Asp Ala Lys Ile
645 650 655

Val Ser Gln Pro Arg Arg Gly Ser Ser Gly Gly Lys Thr Glu Lys Glu
660 665 670

Glu Thr Ala Lys Lys Asn Pro Arg
675 680

<210> SEQ ID NO 20
<211> LENGTH: 600
<212> TYPE: DNA
<213> ORGANISM: hemorrhagic enteritis virus

<400> SEQUENCE: 20

```
atggatcccg ttccgttaga atatatttgg cagtacaacc ctgtgactgg tagagttgga      60
ggagcaaatc agaattacgg acagaggatt aatgttttgc atacaaatcg ttacctctac     120
aacagaatgc agaatgtgca gaaaaaaagc aacgaaagag ccactgaaag aggattacta     180
tctctgaagg gaggaagcac attgccgact attgcagaag atgaacctgc ccagttgaac     240
tcggctatag ttcgcatggc aggattgaat gacttgaaca cggttcaagc accggattca     300
tctaatctgc aaaacctggc caacattgca cttgaagctg ctgaacacaa caaagctacc     360
tcatctctcc taacaacgaa gaagtttgtt gaagagtttc ctcctgttgt ttacgaaaat     420
ccttttctg gctctaattt tgcttatgaa tttaatcctc tgtattcacc gtccgggaat     480
gagttctcca atcctccatt taaattcacc ggaggtgcta ttagcctcac aggacaacac     540
ccagtcctct cgggaggtgc tgttatctta tcaggacaga atccggtact ggacaaagca     600
```

<210> SEQ ID NO 21
<211> LENGTH: 200
<212> TYPE: PRT
<213> ORGANISM: hemorrhagic enteritis virus

<400> SEQUENCE: 21

```
Met Asp Pro Val Pro Leu Glu Tyr Ile Trp Gln Tyr Asn Pro Val Thr
 1               5                  10                  15
Gly Arg Val Gly Gly Ala Asn Gln Asn Tyr Gly Gln Arg Ile Asn Val
                20                  25                  30
Leu His Thr Asn Arg Tyr Leu Tyr Asn Arg Met Gln Asn Val Gln Lys
            35                  40                  45
Lys Ser Asn Glu Arg Ala Thr Glu Arg Gly Leu Leu Ser Leu Lys Gly
     50                  55                  60
Gly Ser Thr Leu Pro Thr Ile Ala Glu Asp Pro Ala Gln Leu Asn
 65                  70                  75                  80
Ser Ala Ile Val Arg Met Ala Gly Leu Asn Asp Leu Asn Thr Val Gln
                85                  90                  95
Ala Pro Asp Ser Ser Asn Leu Gln Asn Leu Ala Asn Ile Ala Leu Glu
                100                 105                 110
Ala Ala Glu His Asn Lys Ala Thr Ser Ser Leu Leu Thr Thr Lys Lys
            115                 120                 125
Phe Val Glu Glu Phe Pro Pro Val Val Tyr Glu Asn Pro Phe Ser Gly
    130                 135                 140
Ser Asn Phe Ala Tyr Glu Phe Asn Pro Leu Tyr Ser Pro Ser Gly Asn
145                 150                 155                 160
Glu Phe Ser Asn Pro Pro Phe Lys Phe Thr Gly Gly Ala Ile Ser Leu
                165                 170                 175
Thr Gly Gln His Pro Val Leu Ser Gly Gly Ala Val Ile Leu Ser Gly
            180                 185                 190
Gln Asn Pro Val Leu Asp Lys Ala
            195                 200

<210> SEQ ID NO 22
<211> LENGTH: 1362
<212> TYPE: DNA
<213> ORGANISM: hemorrhagic enteritis virus

<400> SEQUENCE: 22
atggctactc ctggaaagcg ttctgcagag gaaccagatc aacagacctt gaaaaagtca      60
aaacaatctg accaaagtca gggtttaaat ctagcatatc cttttgataa aataacagaa     120
tttgaagcaa cacctccctt tattcatgtt gggcaaggct agacatatc agatttatcg     180
ttaaatatga gaattggcaa aggattaaag tttgaaaatg gtaatctagt tgtatcagat     240
caacagtata atgttacacc acctttaatt gcagatcagt caacattagg tttaaagtat     300
aatccggatg ttctttcttt aacacattca ggtgctttaa ctttgccaac tattcaacat     360
cccctccagg cttcagctgg aaaatttgaa cttgctttgt catcaggttt aaaatctgat     420
gatcaaggtt aactttaga tttggatcct gtatttttcta cagaatcatc aaaattttg      480
cttaattgtt cattgccgtt agataagaat agtgacaagt taacgttaaa atttggtaat     540
ggtcttggat tgaataatga ccagctagag aatactatga cttataatct tcctttaaaa     600
cgtgatggaa ctaatgttag tctttcattt ggaactaatt tcaaaatatt gaatgagatg     660
ttagatttaa atcttgtggc acctatgtct aattcagcag gaggattagc attgcaattt     720
aaaagccctt tgtcagcaga tgatggtatt ttatcaatta aaacagatac atctttgggt     780
ataacaggaa ataaattagg aataagattg gcccctaaca gtggtctgca aataacacca     840
aatggtctag cagttagtgt taatgctgtg caaattctaa gtagtccttt aattactgca     900
gcgtctatag gcccaccaac aacaatggtt actggaacag tgtcaccggg cagagcaaca     960
```

-continued

```
aatggtcaat ttgtaaccaa aactgctaaa gttttacgtt ataaatttgt gagatgggat   1020
gctctgttaa tcatacagtt tatagataac ataggtgtaa tagaaaaccc taccttttat   1080
cgtaacaaaa gtattgaatt aagatctgct gatttcttga gtcctacgtt aaataataca   1140
tatatagtgc cattgaatgg aggggtaagg gtagaatcac ctactattcc tgtacaatta   1200
gaagttatac ttgaaaacaa ttcctctttc attcaagtag ggtttgttag gttaacagtt   1260
aagaatggta accctcatat gattattcag tgtaatcctg tacctgggaa tattaaaatg   1320
ataaagataa aatctgtaat gctttttact tgtttgatag gc                      1362
```

<210> SEQ ID NO 23
<211> LENGTH: 454
<212> TYPE: PRT
<213> ORGANISM: hemorrhagic enteritis virus

<400> SEQUENCE: 23

```
Met Ala Thr Pro Gly Lys Arg Ser Ala Glu Glu Pro Asp Gln Gln Thr
1               5                   10                  15

Leu Lys Lys Ser Lys Gln Ser Asp Gln Ser Gln Gly Leu Asn Leu Ala
            20                  25                  30

Tyr Pro Phe Asp Lys Ile Thr Glu Phe Glu Ala Thr Pro Pro Phe Ile
        35                  40                  45

His Val Gly Gln Gly Leu Asp Ile Ser Asp Leu Ser Leu Asn Met Arg
    50                  55                  60

Ile Gly Lys Gly Leu Lys Phe Glu Asn Gly Asn Leu Val Val Ser Asp
65                  70                  75                  80

Gln Gln Tyr Asn Val Thr Pro Pro Leu Ile Ala Asp Gln Ser Thr Leu
                85                  90                  95

Gly Leu Lys Tyr Asn Pro Asp Val Leu Ser Leu Thr His Ser Gly Ala
            100                 105                 110

Leu Thr Leu Pro Thr Ile Gln His Pro Leu Gln Ala Ser Ala Gly Lys
        115                 120                 125

Phe Glu Leu Ala Leu Ser Ser Gly Leu Lys Ser Asp Asp Gln Gly Leu
    130                 135                 140

Thr Leu Asp Leu Asp Pro Val Phe Ser Thr Glu Ser Ser Lys Phe Leu
145                 150                 155                 160

Leu Asn Cys Ser Leu Pro Leu Asp Lys Asn Ser Asp Lys Leu Thr Leu
                165                 170                 175

Lys Phe Gly Asn Gly Leu Gly Leu Asn Asn Asp Gln Leu Glu Asn Thr
            180                 185                 190

Met Thr Tyr Asn Leu Pro Leu Lys Arg Asp Gly Thr Asn Val Ser Leu
        195                 200                 205

Ser Phe Gly Thr Asn Phe Lys Ile Leu Asn Glu Met Leu Asp Leu Asn
    210                 215                 220

Leu Val Ala Pro Met Ser Asn Ser Ala Gly Gly Leu Ala Leu Gln Phe
225                 230                 235                 240

Lys Ser Pro Leu Ser Ala Asp Asp Gly Ile Leu Ser Ile Lys Thr Asp
                245                 250                 255

Thr Ser Leu Gly Ile Thr Gly Asn Lys Leu Gly Ile Arg Leu Ala Pro
            260                 265                 270

Asn Ser Gly Leu Gln Ile Thr Pro Asn Gly Leu Ala Val Ser Val Asn
        275                 280                 285

Ala Val Gln Ile Leu Ser Ser Pro Leu Ile Thr Ala Ala Ser Ile Gly
    290                 295                 300
```

```
Pro Pro Thr Thr Met Val Thr Gly Thr Val Ser Pro Gly Arg Ala Thr
305                 310                 315                 320

Asn Gly Gln Phe Val Thr Lys Thr Ala Lys Val Leu Arg Tyr Lys Phe
            325                 330                 335

Val Arg Trp Asp Ala Leu Leu Ile Ile Gln Phe Ile Asp Asn Ile Gly
        340                 345                 350

Val Ile Glu Asn Pro Thr Phe Tyr Arg Asn Lys Ser Ile Glu Leu Arg
        355                 360                 365

Ser Ala Asp Phe Leu Ser Pro Thr Leu Asn Asn Thr Tyr Ile Val Pro
    370                 375                 380

Leu Asn Gly Gly Val Arg Val Glu Ser Pro Thr Ile Pro Val Gln Leu
385                 390                 395                 400

Glu Val Ile Leu Glu Asn Asn Ser Ser Phe Ile Gln Val Gly Phe Val
            405                 410                 415

Arg Leu Thr Val Lys Asn Gly Asn Pro His Met Ile Ile Gln Cys Asn
                420                 425                 430

Pro Val Pro Gly Asn Ile Lys Met Ile Lys Ile Lys Ser Val Met Leu
            435                 440                 445

Phe Thr Cys Leu Ile Gly
    450

<210> SEQ ID NO 24
<211> LENGTH: 1101
<212> TYPE: DNA
<213> ORGANISM: hemorrhagic enteritis virus

<400> SEQUENCE: 24
atgaataatg aagttgaaga attctacgat gtagttggac aatggaaaac tgctgtagac      60
agtattaact caagcatact accaggatgt gatttgccgc catttaaaga atttgaaagc     120
tataactcta atatagactt gagaagcaat atgaggaaat acaacgaaat taacaacatt     180
aacaagatgt atctaactaa aaactctgaa ctgccttcta tcaatatgaa ctctgatcca     240
cttattagtt tagtaatcgg acctacaggt tgcgggaaaa gccaattaat tagaaattta     300
ctgggattca aaaaaataca accaatgcca gaaacgatca tcttcataac tcctacaaaa     360
ggaactattt catatgacga agtaatatta tggaaaactc aactacaaga aggaaattat     420
tctgctcaag ataatacccct ttacccaacc acaaaggtat tcaccattaa ttttctagaa     480
tgtgcttttg atgatgtcat taccccagag aatctagatg ttaacaacga aaattctatc     540
tttaatattc ataccaaaaa agggccagta tgcgtaattc tagatgaatg tatgcagaaa     600
ttaatacaga aaccaaatat aagcccatta tattgtagtt taccatcaaa gctatctagt     660
agatatggtc atgcattcta tatgttcgtt gttttacata atgtaaatcc gttatcagga     720
aacggtaata atattatgga cttgaagact caagccaaat tacacatttt aagcacaaaa     780
aaccaaccac tacaattatc taattttgta cataatcgat caggaggaat ggactctaac     840
gtacgaacga tactattaaa cagtattgta tctgaaaaaa atccgaaata ttcttttgta     900
atgtttaata cttgtccaac aagggaatca tttcaatggt cagcaatact cgagggaggg     960
aaaagtatta tacctttatg tttagatatg caaagtttac ttctagactc tgtaaataaa    1020
atctgtaaca ttcacttatg taaattaaaa aataagaaaa ggtacttgaa agaaaaacaa    1080
aaacgcatgt atgatgaaat t                                               1101

<210> SEQ ID NO 25
```

```
<211> LENGTH: 367
<212> TYPE: PRT
<213> ORGANISM: hemorrhagic enteritis virus

<400> SEQUENCE: 25

Met Asn Asn Glu Val Glu Glu Phe Tyr Asp Val Val Gly Gln Trp Lys
1               5                   10                  15

Thr Ala Val Asp Ser Ile Asn Ser Ser Ile Leu Pro Gly Cys Asp Leu
            20                  25                  30

Pro Pro Phe Lys Glu Phe Glu Ser Tyr Asn Ser Asn Ile Asp Leu Arg
        35                  40                  45

Ser Asn Met Arg Lys Tyr Asn Glu Ile Asn Asn Ile Asn Lys Met Tyr
    50                  55                  60

Leu Thr Lys Asn Ser Glu Leu Pro Ser Ile Asn Met Asn Ser Asp Pro
65                  70                  75                  80

Leu Ile Ser Leu Val Ile Gly Pro Thr Gly Cys Gly Lys Ser Gln Leu
                85                  90                  95

Ile Arg Asn Leu Leu Gly Phe Lys Lys Ile Gln Pro Met Pro Glu Thr
            100                 105                 110

Ile Ile Phe Ile Thr Pro Thr Lys Gly Thr Ile Ser Tyr Asp Glu Val
        115                 120                 125

Ile Leu Trp Lys Thr Gln Leu Gln Glu Gly Asn Tyr Ser Ala Gln Asp
    130                 135                 140

Asn Thr Leu Tyr Pro Thr Thr Lys Val Phe Thr Ile Asn Phe Leu Glu
145                 150                 155                 160

Cys Ala Phe Asp Asp Val Ile Thr Pro Glu Asn Leu Asp Val Asn Asn
                165                 170                 175

Glu Asn Ser Ile Phe Asn Ile His Thr Lys Lys Gly Pro Val Cys Val
            180                 185                 190

Ile Leu Asp Glu Cys Met Gln Lys Leu Ile Gln Lys Pro Asn Ile Ser
        195                 200                 205

Pro Leu Tyr Cys Ser Leu Pro Ser Lys Leu Ser Ser Arg Tyr Gly His
    210                 215                 220

Ala Phe Tyr Met Phe Val Val Leu His Asn Val Asn Pro Leu Ser Gly
225                 230                 235                 240

Asn Gly Asn Asn Ile Met Asp Leu Lys Thr Gln Ala Lys Leu His Ile
                245                 250                 255

Leu Ser Thr Lys Asn Gln Pro Leu Gln Leu Ser Asn Phe Val His Asn
            260                 265                 270

Arg Ser Gly Gly Met Asp Ser Asn Val Arg Thr Ile Leu Leu Asn Ser
        275                 280                 285

Ile Val Ser Glu Lys Asn Pro Lys Tyr Ser Phe Val Met Phe Asn Thr
    290                 295                 300

Cys Pro Thr Arg Glu Ser Phe Gln Trp Ser Ala Ile Leu Glu Gly Gly
305                 310                 315                 320

Lys Ser Ile Ile Pro Leu Cys Leu Asp Met Gln Ser Leu Leu Leu Asp
                325                 330                 335

Ser Val Asn Lys Ile Cys Asn Ile His Leu Cys Lys Leu Lys Asn Lys
            340                 345                 350

Lys Arg Tyr Leu Lys Glu Lys Gln Lys Arg Met Tyr Asp Glu Ile
        355                 360                 365

<210> SEQ ID NO 26
<211> LENGTH: 3336
<212> TYPE: DNA
```

-continued

<213> ORGANISM: hemorrhagic enteritis virus

<400> SEQUENCE: 26

```
ttcatcttcg aattcctgta gtaagatagg atttgttatt ctggggtttg ggtggtagag     60
atcataagga attaaagtgt ttgtctttag aaagtaaagg gttggatcat tccacggccg    120
tagttcgcgt attaattgta tttcatgaac agaaaagggg gagaattttc cgtaagactt    180
acataacgtt cttttcaaag cagttctttc tgtttggaag atctcaccag attttaattc    240
tgaagtgtgg tagttgaagc attcttccag gatttcaaaa gttatgtctg cggtacagtg    300
accctttgct cgtaattttc ctgtttttga atttttgcag gtggtacacg tgatttcttt    360
aagggcgtac agctttggag cgagaaaaat actttttgaa gaatatgcag gtgaattaca    420
caaattacac caagtttcac attctactgc ccaaacaatt gaaggttttt taggatcaaa    480
tgttagttgt gaatttttgt ttttaattct atgttgtcca tattttaaca tattttgatg    540
tcctttttct gtgagaaata gactgtctgt gtcaccgtag attgatttaa tggttttgaa    600
ttgaactggt atactatctt catcactgta taggatttcg cgccactcgc tcataaaggc    660
tcttgtccac gctaatacga agcttgctag ttgagttgga tatcttttgt ttgtcggatg    720
taaattcgtt gattttaaca tgtaaatagt gaggttttct gatgtgacgt ctaagatgtt    780
gaatggtttg taggttccca cgtgagcagt cgaagttgaa gtttgtgagg ctgggctttc    840
atccataaat tctaaactgt taaacggact ggtaagctca tcatccagtt ctaaatttct    900
ctctgcactg tcagttcggt tttttaaggt aaatgttaaa ttttctatac taacatatgg    960
aaggttgtaa gttggtagag tagtaatgct gtcaatggtt agttgtttgt tcaataattg   1020
atttcttatt ttaggatttt cttgaatgtg gttttcgaaa attgtaatgt cattgctttc   1080
tcttgtagca aaactaccgt atagtgcatt acttaggagt ttgctgattg ctcttttaac   1140
aggatttttt tcaacggtgg ctttttcttt tgctagaata tttttagtaa catattctaa   1200
gcagcaagtg ttccacgttg ggaatactgt gtttagcttg tggggaataa tgtttacttt   1260
ccatcctcta ttatggagtg tgataatatc aattgaggta acaatttcat ttttcagtat   1320
ttcgttcgtc caacataatt tgccgctttg tcttgaacat aatggcggta gaggatcaag   1380
atgttctgga ggtggcggga tggcgtcaat cattactacc attggcttta tatcagtaaa   1440
atatgatagt tttgttttag tttttttttaa tttttcgttt aactttgtaa tttcattgtt   1500
tctttctttc tctcctattg gaaatccgta tggcattgga tgagttagag cactagcata   1560
catgccgcaa atatcgtaaa caaaaatttt ttctttgaat attcctaagt gtgttgggta   1620
acaacgtcca cctctaacgg actgacggat gaaactgtac atttcatcag atggtgctac   1680
tatgtctggc agggtggagg cttttgttcc attttgtttg aagtgtaact gtctaaaaat   1740
ggcgtgagaa ttagatgaaa tagtcggtct tttaaaaata ttaaaattgc attttaggtt   1800
tagttcctct ttgatgaatg tatcgaaagt atttaggagg gtttttgtta gttcttccgt   1860
tattttaacg tctttaatac aatagtcgat taattcttta acaatgtcat atttgacttc   1920
ctttttttct aaccaaattt ctttttgttc gttatattct tctttgctag accaatattt   1980
ttctgatgga aacgagtctg agtctgtaga taatgaattg gttgacatgt actcatttat   2040
agctttgaac ggacaacaac ctttgtgaat ttttaagttg tatgctttgg ccgcttcttt   2100
tagagaagtg tgtgttattt ggaaagtatc tctgaccata gacttgatat ataaattttt   2160
tatactttct ggatgtggaa ttccttcttt aatctgtgaa agtatttcac ttttattatt   2220
ttttttttct tctttagcta catagtagtc tgggttgggg aatttaattg taatatcgtt   2280
```

-continued

```
aaaaagtatt ctgccttgtc ttggcataaa atttctttca actgtgaaaa ggggagtgat   2340
gtctaggttt tcgtcttgaa ggatttgtgt tgctaataga atttcatcga atgactgaat   2400
gttgtgtccg atgatgtaaa attctatgaa aattggttta actttcagac tcattatgag   2460
gttagtatgt tcacttaaat tgatatttgt aattgattct aaattttgtg tttgagcgaa   2520
atcttcgaga atttctcggt tttctggtgt taaaattaat tttgtgaagt aatctgtgag   2580
tgcaaatagg atgttatttc ttaattttct gaactccgta ctaatgaagt ttttaacttt   2640
agaaaaccag aagtacgtag aattttttgt ttgaatagat tttattttgg ctatttctgt   2700
tttacagata ttgataagac aatcatctcc gaaaattgaa aagcatagta gaagaggatt   2760
taataaaact ccagatgttt cagctagtgt aaatgtttct atatcgtaga taaggaagag   2820
tttttttgtg ttttcatttt ctcctatagg ttgaaatggt atagtttccc agaattttct   2880
tgtgtcattg tctacgctgt tgtagtagta agtagatctt aagtcattgc aggtatgaat   2940
tgcggagtag attctaccac atgagctgca tttttgttgt tgagtccatg attttatcca   3000
gcataatttt gacttatcat atatgaagtc taattcaata tattcatgcg atgttttgaa   3060
ttcattttgg atcataacac atccagttaa ttttttccag atagttattg atttgaccgg   3120
taagtttttt acattttcaa tatcgctgtt tgtgggcttg tatttactac aaatgaggat   3180
atatgattgt gcatctttta cttttttgc aagtttttta caattaaata aattatatgt   3240
ccaagctatt tctattatag tggcttttat gtctttttta catatttgca acctgtatgg   3300
aatttcgttt tgagtggtat aaatgtattt gctcat                             3336
```

<210> SEQ ID NO 27
<211> LENGTH: 1112
<212> TYPE: PRT
<213> ORGANISM: hemorrhagic enteritis virus

<400> SEQUENCE: 27

```
Met Ser Lys Tyr Ile Tyr Thr Thr Gln Asn Glu Ile Pro Tyr Arg Leu
1               5                   10                  15

Gln Ile Cys Lys Lys Asp Ile Lys Ala Thr Ile Ile Glu Ile Ala Trp
            20                  25                  30

Thr Tyr Asn Leu Phe Asn Cys Lys Lys Leu Ala Lys Lys Val Lys Asp
        35                  40                  45

Ala Gln Ser Tyr Ile Leu Ile Cys Ser Lys Tyr Lys Pro Thr Asn Ser
    50                  55                  60

Asp Ile Glu Asn Val Lys Asn Leu Pro Val Lys Ser Ile Thr Ile Trp
65                  70                  75                  80

Lys Lys Leu Thr Gly Cys Val Met Ile Gln Asn Glu Phe Lys Thr Ser
                85                  90                  95

His Glu Tyr Ile Glu Leu Asp Phe Ile Tyr Asp Lys Ser Lys Leu Cys
            100                 105                 110

Trp Ile Lys Ser Trp Thr Gln Gln Gln Lys Cys Ser Ser Cys Gly Arg
        115                 120                 125

Ile Tyr Ser Ala Ile His Thr Cys Asn Asp Leu Arg Ser Thr Tyr Tyr
    130                 135                 140

Tyr Asn Ser Val Asp Asn Asp Thr Arg Lys Phe Trp Glu Thr Ile Pro
145                 150                 155                 160

Phe Gln Pro Ile Gly Glu Asn Glu Asn Thr Lys Lys Leu Phe Leu Ile
                165                 170                 175

Tyr Asp Ile Glu Thr Phe Thr Leu Ala Glu Thr Ser Gly Val Leu Leu
```

-continued

```
                180                 185                 190
Asn Pro Leu Leu Leu Cys Phe Ser Ile Phe Gly Asp Asp Cys Leu Ile
            195                 200                 205
Asn Ile Cys Lys Thr Glu Ile Ala Lys Ile Lys Ser Ile Gln Thr Lys
            210                 215                 220
Asn Ser Thr Tyr Phe Trp Phe Ser Lys Val Lys Asn Phe Ile Ser Thr
225                 230                 235                 240
Glu Phe Arg Lys Leu Arg Asn Asn Ile Leu Phe Ala Leu Thr Asp Tyr
                245                 250                 255
Phe Thr Lys Leu Ile Leu Thr Pro Glu Asn Arg Glu Ile Leu Glu Asp
                260                 265                 270
Phe Ala Gln Thr Gln Asn Leu Glu Ser Ile Thr Asn Ile Asn Leu Ser
                275                 280                 285
Glu His Thr Asn Leu Ile Met Ser Leu Lys Val Lys Pro Ile Phe Ile
                290                 295                 300
Glu Phe Tyr Ile Ile Gly His Asn Ile Gln Ser Phe Asp Glu Ile Leu
305                 310                 315                 320
Leu Ala Thr Gln Ile Leu Gln Asp Glu Asn Leu Asp Ile Thr Pro Leu
                325                 330                 335
Phe Thr Val Glu Arg Asn Phe Met Pro Arg Gln Gly Arg Ile Leu Phe
                340                 345                 350
Asn Asp Ile Thr Ile Lys Phe Pro Asn Pro Asp Tyr Tyr Val Ala Lys
                355                 360                 365
Glu Glu Lys Lys Asn Asn Lys Ser Glu Ile Leu Ser Gln Ile Lys Glu
                370                 375                 380
Gly Ile Pro His Pro Glu Ser Ile Lys Asn Leu Tyr Ile Lys Ser Met
385                 390                 395                 400
Val Arg Asp Thr Phe Gln Ile Thr His Thr Ser Leu Lys Glu Ala Ala
                405                 410                 415
Lys Ala Tyr Asn Leu Lys Ile His Lys Gly Cys Cys Pro Phe Lys Ala
                420                 425                 430
Ile Asn Glu Tyr Met Ser Thr Asn Ser Leu Ser Thr Asp Ser Asp Ser
                435                 440                 445
Phe Pro Ser Glu Lys Tyr Trp Ser Ser Lys Glu Glu Tyr Asn Glu Gln
                450                 455                 460
Lys Glu Ile Trp Leu Glu Lys Lys Glu Val Lys Tyr Asp Ile Val Lys
465                 470                 475                 480
Glu Leu Ile Asp Tyr Cys Ile Lys Asp Val Lys Ile Thr Glu Glu Leu
                485                 490                 495
Thr Lys Thr Leu Leu Asn Thr Phe Asp Thr Phe Ile Lys Glu Glu Leu
                500                 505                 510
Asn Leu Lys Cys Asn Phe Asn Ile Phe Lys Arg Pro Thr Ile Ser Ser
                515                 520                 525
Asn Ser His Ala Ile Phe Arg Gln Leu His Phe Lys Gln Asn Gly Thr
                530                 535                 540
Lys Ala Ser Thr Leu Pro Asp Ile Val Ala Pro Ser Asp Glu Met Tyr
545                 550                 555                 560
Ser Phe Ile Arg Gln Ser Val Arg Gly Gly Arg Cys Tyr Pro Thr His
                565                 570                 575
Leu Gly Ile Phe Lys Glu Lys Ile Phe Val Tyr Asp Ile Cys Gly Met
                580                 585                 590
Tyr Ala Ser Ala Leu Thr His Pro Met Pro Tyr Gly Phe Pro Ile Gly
                595                 600                 605
```

-continued

```
Glu Lys Glu Arg Asn Asn Glu Ile Thr Lys Leu Asn Glu Lys Leu Lys
    610                 615                 620
Lys Thr Lys Thr Lys Leu Ser Tyr Phe Thr Asp Ile Lys Pro Met Val
625                 630                 635                 640
Val Met Ile Asp Ala Ile Pro Pro Pro Glu His Leu Asp Pro Leu
                645                 650                 655
Pro Pro Leu Cys Ser Arg Gln Ser Gly Lys Leu Cys Trp Thr Asn Glu
                660                 665                 670
Ile Leu Lys Asn Glu Ile Val Thr Ser Ile Asp Ile Ile Thr Leu His
                675                 680                 685
Asn Arg Gly Trp Lys Val Asn Ile Ile Pro His Lys Leu Asn Thr Val
    690                 695                 700
Phe Pro Thr Trp Asn Thr Cys Cys Leu Glu Tyr Val Thr Lys Asn Ile
705                 710                 715                 720
Leu Ala Lys Glu Lys Ala Thr Val Glu Lys Asn Pro Val Lys Arg Ala
                725                 730                 735
Ile Ser Lys Leu Leu Ser Asn Ala Leu Tyr Gly Ser Phe Ala Thr Arg
                740                 745                 750
Glu Ser Asn Asp Ile Thr Ile Phe Glu Asn His Ile Gln Glu Asn Pro
                755                 760                 765
Lys Ile Arg Asn Gln Leu Leu Asn Lys Gln Leu Thr Ile Asp Ser Ile
    770                 775                 780
Thr Thr Leu Pro Thr Tyr Asn Leu Pro Tyr Val Ser Ile Glu Asn Leu
785                 790                 795                 800
Thr Phe Thr Leu Lys Asn Arg Thr Asp Ser Ala Glu Arg Asn Leu Glu
                805                 810                 815
Leu Asp Asp Glu Leu Thr Ser Pro Phe Asn Ser Leu Glu Phe Met Asp
                820                 825                 830
Glu Ser Pro Ala Ser Gln Thr Ser Thr Ser Thr Ala His Val Gly Thr
                835                 840                 845
Tyr Lys Pro Phe Asn Ile Leu Asp Val Thr Ser Glu Asn Leu Thr Ile
    850                 855                 860
Tyr Met Leu Lys Ser Thr Asn Leu His Pro Thr Asn Lys Arg Tyr Pro
865                 870                 875                 880
Thr Gln Leu Ala Ser Phe Val Leu Ala Trp Thr Arg Ala Phe Met Ser
                885                 890                 895
Glu Trp Arg Glu Ile Leu Tyr Ser Asp Glu Asp Ser Ile Pro Val Gln
                900                 905                 910
Phe Lys Thr Ile Lys Ser Ile Tyr Gly Asp Thr Asp Ser Leu Phe Leu
    915                 920                 925
Thr Glu Lys Gly His Gln Asn Met Leu Lys Tyr Gly Gln His Arg Ile
    930                 935                 940
Lys Asn Lys Asn Ser Gln Leu Thr Phe Asp Pro Lys Lys Pro Ser Ile
945                 950                 955                 960
Val Trp Ala Val Glu Cys Glu Thr Trp Cys Asn Leu Cys Asn Ser Pro
                965                 970                 975
Ala Tyr Ser Ser Lys Ser Ile Phe Leu Ala Pro Lys Leu Tyr Ala Leu
                980                 985                 990
Lys Glu Ile Thr Cys Thr Thr Cys  Lys Asn Ser Lys Thr  Gly Lys Leu
    995                 1000                1005
Arg Ala  Lys Gly His Cys Thr  Ala Asp Ile Thr Phe  Glu Ile Leu
    1010                1015                1020
```

-continued

```
Glu Glu  Cys Phe Asn Tyr His  Thr Ser Glu Leu Lys  Ser Gly Glu
    1025                 1030                 1035

Ile Phe  Gln Thr Glu Arg Thr  Ala Leu Lys Arg Thr  Leu Cys Lys
    1040                 1045                 1050

Ser Tyr  Gly Lys Phe Ser Pro  Phe Ser Val His Glu  Ile Gln Leu
    1055                 1060                 1065

Ile Arg  Glu Leu Arg Pro Trp  Asn Asp Pro Thr Leu  Tyr Phe Leu
    1070                 1075                 1080

Lys Thr  Asn Thr Leu Ile Pro  Tyr Asp Leu Tyr His  Pro Asn Pro
    1085                 1090                 1095

Arg Ile  Thr Asn Pro Ile Leu  Leu Gln Glu Phe Glu  Asp Glu
    1100                 1105                 1110

<210> SEQ ID NO 28
<211> LENGTH: 1791
<212> TYPE: DNA
<213> ORGANISM: hemorrhagic enteritis virus

<400> SEQUENCE: 28
atgtctttct ttcagattaa caattatgcc cgcctaacta accaagaaga agacaccatc     60
agatttatgc atttaacaca attcacagat caagtcaaca tccctatgtt tgtaagaagt    120
attcctggat taagatggtg cagtacattc tttaactatc agattttaat gttagaaaat    180
ttagcaccac aaggccctgc cgttttaaat cctcctttaa acggattgcc gcctcctcat    240
ttgctgattg gctacgctta tctattcaat gtgaacaata actaccgttt tgaaagcaga    300
acatatacaa aattaaacta tgaagctgat caatctacta caagaagacc tagaaatttt    360
tggtctattc taagtgattg ttcatataca attaacacaa gtaatgtgcg caccattcca    420
gaaaactacg aagataactt aaaccagttt caagaagaaa ttcttattaa tagaattaga    480
gctgacattg aatctagaag taacatgcaa ggaacaggtg ttacattaca accagaagct    540
tacgaaaata taaatatcca aaatgaaata aataaaatgt acgtaacaaa tttaagagat    600
tttattaact ccaaaagttt tgctttcaat caaaggtatc aatatgaaac tgaaaaagat    660
attaacacat taaagtgcat taactacact ttagaactac ttgcaaaatt tatttataat    720
tggcaattta aagatgaaaa aatatacgta ccgttgaagg ataattggct tcaaatcctc    780
aaaacagaat acgacaaatg gcagcctgaa atggatataa actacgctgt atcatatatc    840
acagcattaa attcaatgat atttcctttc aaagagtgga aacaaatctt aaaaggtggt    900
gcaagattaa gaagtggcac tagaacagac ttaccatttt taagacagag agaaaatcaa    960
agagccataa ctgaacaaat gagaagaaat agaggacaga tagtttcgag gtttatagac   1020
agcttacctt taatcagaag aataagaaga cccccaccaa gtcctgtgga agaggaagat   1080
gcaggagaag gtccaagtgc cggacctgaa gaagaagaaa tggaagaaga attaggcaat   1140
gaaatccttc gaatttttca aaatatcctt aatgaactaa gagcagaatt aacagaacct   1200
gcaagagaac atgaaatttt ttctttcggt cagttatttt acaatctttt acagagagca   1260
aatgaacaag gaagggtaac tagagagttt ataagaagat tcatatttta ctttttcata   1320
gctgaacaca tcagtagtac actattttat tatcatgctc tattaaactt aaacgttatt   1380
ttcagaagat atgtaaatat gcaatatgtc caagtcataa tgactggacg agatcatgaa   1440
ggaaatgtta accttcacag agtttggact aacacaaaca tttctccatt tttaagaata   1500
tttagaacaa tcatcaatga ccttctaata atatgtgaca gaaggccaga tagtattgaa   1560
actcaagcag aacaagaaga cctacttaca tccctatcac acagaccaga atctggagat   1620
```

```
ccaaacgacc ttctaaacca agctagactt aatgaagatt taatcaacac agtaactctt    1680
tcctttaaaa tcaagcctat tggtcttgta acaattgcta caaacagaca ataattaac     1740 aatgcttcgg ctgtaagaac acaagaaatg agaagattaa gacaaccaag a             1791
```

<210> SEQ ID NO 29
<211> LENGTH: 597
<212> TYPE: PRT
<213> ORGANISM: hemorrhagic enteritis virus

<400> SEQUENCE: 29

```
Met Ser Phe Phe Gln Ile Asn Asn Tyr Ala Arg Leu Thr Asn Gln Glu
1               5                   10                  15

Glu Asp Thr Ile Arg Phe Met His Leu Thr Gln Phe Thr Asp Gln Val
                20                  25                  30

Asn Ile Pro Met Phe Val Arg Ser Ile Pro Gly Leu Arg Trp Cys Ser
            35                  40                  45

Thr Phe Phe Asn Tyr Gln Ile Leu Met Leu Glu Asn Leu Ala Pro Gln
        50                  55                  60

Gly Pro Ala Val Leu Asn Pro Leu Asn Gly Leu Pro Pro His
65                  70                  75                  80

Leu Leu Ile Gly Tyr Ala Tyr Leu Phe Asn Val Asn Asn Tyr Arg
                85                  90                  95

Phe Glu Ser Arg Thr Tyr Thr Lys Leu Asn Tyr Glu Ala Asp Gln Ser
            100                 105                 110

Thr Thr Arg Arg Pro Arg Asn Phe Trp Ser Ile Leu Ser Asp Cys Ser
        115                 120                 125

Tyr Thr Ile Asn Thr Ser Asn Val Arg Thr Ile Pro Glu Asn Tyr Glu
    130                 135                 140

Asp Asn Leu Asn Gln Phe Gln Glu Glu Ile Leu Ile Asn Arg Ile Arg
145                 150                 155                 160

Ala Asp Ile Glu Ser Arg Ser Asn Met Gln Gly Thr Gly Val Thr Leu
                165                 170                 175

Gln Pro Glu Ala Tyr Glu Asn Ile Asn Ile Gln Asn Glu Ile Asn Lys
            180                 185                 190

Met Tyr Val Thr Asn Leu Arg Asp Phe Ile Asn Ser Lys Ser Phe Ala
        195                 200                 205

Phe Asn Gln Arg Tyr Gln Tyr Glu Thr Glu Lys Asp Ile Asn Thr Leu
    210                 215                 220

Lys Cys Ile Asn Tyr Thr Leu Glu Leu Leu Ala Lys Phe Ile Tyr Asn
225                 230                 235                 240

Trp Gln Phe Lys Asp Glu Lys Ile Tyr Val Pro Leu Lys Asp Asn Trp
                245                 250                 255

Leu Gln Ile Leu Lys Thr Glu Tyr Asp Lys Trp Gln Pro Glu Met Asp
            260                 265                 270

Ile Asn Tyr Ala Val Ser Tyr Ile Thr Ala Leu Asn Ser Met Ile Phe
        275                 280                 285

Pro Phe Lys Glu Trp Lys Thr Asn Leu Lys Gly Gly Ala Arg Leu Arg
    290                 295                 300

Ser Gly Thr Arg Thr Asp Leu Pro Phe Leu Arg Gln Arg Glu Asn Gln
305                 310                 315                 320

Arg Ala Ile Thr Glu Gln Met Arg Arg Asn Arg Gly Gln Ile Val Ser
                325                 330                 335

Arg Phe Ile Asp Ser Leu Pro Leu Ile Arg Arg Ile Arg Arg Pro Pro
```

|  |  |  |  |  |  |  |  |  |  |
|--|--|--|--|--|--|--|--|--|--|
| | | 340 | | | 345 | | | 350 | |
| Pro | Ser | Pro | Val | Glu | Glu | Asp | Ala | Gly | Glu | Gly | Pro | Ser | Ala | Gly |
| | | | 355 | | | | 360 | | | | 365 | | | |

Pro Ser Pro Val Glu Glu Asp Ala Gly Glu Gly Pro Ser Ala Gly
                355                 360                 365

Pro Glu Glu Glu Met Glu Glu Leu Gly Asn Glu Ile Leu Arg
    370                 375                 380

Ile Phe Gln Asn Ile Leu Asn Glu Leu Arg Ala Glu Leu Thr Glu Pro
385                 390                 395                 400

Ala Arg Glu His Glu Ile Phe Ser Phe Gly Gln Leu Phe Tyr Asn Leu
                405                 410                 415

Leu Gln Arg Ala Asn Glu Gln Gly Arg Val Thr Arg Glu Phe Ile Arg
                420                 425                 430

Arg Phe Ile Phe Tyr Phe Phe Ile Ala Glu His Ile Ser Ser Thr Leu
                435                 440                 445

Phe Tyr Tyr His Ala Leu Leu Asn Leu Asn Val Ile Phe Arg Arg Tyr
        450                 455                 460

Val Asn Met Gln Tyr Val Gln Val Ile Met Thr Gly Arg Asp His Glu
465                 470                 475                 480

Gly Asn Val Asn Leu His Arg Val Trp Thr Asn Thr Asn Ile Ser Pro
                485                 490                 495

Phe Leu Arg Ile Phe Arg Thr Ile Ile Asn Asp Leu Leu Ile Ile Cys
                500                 505                 510

Asp Arg Arg Pro Asp Ser Ile Glu Thr Gln Ala Glu Gln Glu Asp Leu
                515                 520                 525

Leu Thr Ser Leu Ser His Arg Pro Glu Ser Gly Asp Pro Asn Asp Leu
        530                 535                 540

Leu Asn Gln Ala Arg Leu Asn Glu Asp Leu Ile Asn Thr Val Thr Leu
545                 550                 555                 560

Ser Phe Lys Ile Lys Pro Ile Gly Leu Val Thr Ile Ala Thr Asn Arg
                565                 570                 575

Gln Ile Ile Asn Asn Ala Ser Ala Val Arg Thr Gln Glu Met Arg Arg
                580                 585                 590

Leu Arg Gln Pro Arg
        595

<210> SEQ ID NO 30
<211> LENGTH: 1038
<212> TYPE: DNA
<213> ORGANISM: hemorrhagic enteritis virus

<400> SEQUENCE: 30

```
atgcaatacg ctacaggatt acaagcattg tttgcatgcc aagctgaagc gaatatttta     60
cctacttctg attactgggc caaactggtt gagacatatg ttaagaagaa taaaccagat    120
cttaatctta cgatttcctc cgctaaatct ttttatcact tgctggccg tatcgtaagc    180
agttttgtgt ataatgatag cggcttaatt tgcaattata attgccttgg agccaatatc    240
tgggttcata attgggatga agataacatt agatgttttc atggcactgt tatgctttca    300
aaacccataa cttacagcct gtctcctcaa tcagaggaag gaatgagagc tctgacagct    360
ggtgagggca gattagagaa agaaaaaaat caaaaagacg tgataaagct aacaaattat    420
agcaatatag tctgtccatt agatagtaat gttcagtggc aactattca ttcaccagac     480
tcttgtggaa tgaattttgg caacaaagaa aaagcaaaag ctgcctttct tcataatatt    540
gattggacaa gtgctatgtt tcctaaagca agaaatgtg aaatttctga aaaatgatt      600
atagttacaa agtgcttctg taactatggt catgaaaaca ttcagcttgg cagacaaatc    660
```

```
tgcaaaatga ctgcttttga atacctgga gcgaatgaca tagaccctga gagttgtcat      720
gatgatatgc ttcttgcaac tgccaagtat aaacacacct ttgtgtttca atgttgcaat      780
cccattagac ttaaaagaaa tgctaaggat aaagataatc agactcacaa acattgtgat      840
tttaaattgt caatgattga tgtgagacag gctatgaaaa ttagcaaaga tatatatact      900
aagctgaagg aaaccataga tgatggctcc cctactaaaa taatgttgcc tgcttttgta      960
ttcaatccta aaaagcattc ttttaagcaa gctattgtgg ctcaacacga ggtggaaagt     1020
gatgatgacg cttttttgt                                                   1038
```

<210> SEQ ID NO 31
<211> LENGTH: 346
<212> TYPE: PRT
<213> ORGANISM: hemorrhagic enteritis virus

<400> SEQUENCE: 31

```
Met Gln Tyr Ala Thr Gly Leu Gln Ala Leu Phe Ala Cys Gln Ala Glu
1               5                   10                  15

Ala Asn Ile Leu Pro Thr Ser Asp Tyr Trp Ala Lys Leu Val Glu Thr
            20                  25                  30

Tyr Val Lys Lys Asn Lys Pro Asp Leu Asn Leu Thr Ile Ser Ser Ala
        35                  40                  45

Lys Ser Phe Tyr His Phe Ala Gly Arg Ile Val Ser Ser Phe Val Tyr
    50                  55                  60

Asn Asp Ser Gly Leu Ile Cys Asn Tyr Asn Cys Leu Gly Ala Asn Ile
65                  70                  75                  80

Trp Val His Asn Trp Asp Glu Asp Asn Ile Arg Cys Phe His Gly Thr
                85                  90                  95

Val Met Leu Ser Lys Pro Ile Thr Tyr Ser Leu Ser Pro Gln Ser Glu
            100                 105                 110

Glu Gly Met Arg Ala Leu Thr Ala Gly Glu Gly Arg Leu Glu Lys Glu
        115                 120                 125

Lys Asn Gln Lys Asp Val Ile Lys Leu Thr Asn Tyr Ser Asn Ile Val
    130                 135                 140

Cys Pro Leu Asp Ser Asn Val Gln Trp Pro Thr Ile His Ser Pro Asp
145                 150                 155                 160

Ser Cys Gly Met Asn Phe Gly Asn Lys Glu Lys Ala Lys Ala Ala Phe
                165                 170                 175

Leu His Asn Ile Asp Trp Thr Ser Ala Met Phe Pro Lys Ala Lys Lys
            180                 185                 190

Cys Glu Ile Ser Glu Lys Met Ile Ile Val Thr Lys Cys Phe Cys Asn
        195                 200                 205

Tyr Gly His Glu Asn Ile Gln Leu Gly Arg Gln Ile Cys Lys Met Thr
    210                 215                 220

Ala Phe Glu Ile Pro Gly Ala Asn Asp Ile Asp Pro Glu Ser Cys His
225                 230                 235                 240

Asp Asp Met Leu Leu Ala Thr Ala Lys Tyr Lys His Thr Phe Val Phe
                245                 250                 255

Gln Cys Cys Asn Pro Ile Arg Leu Lys Arg Asn Ala Lys Asp Lys Asp
            260                 265                 270

Asn Gln Thr His Lys His Cys Asp Phe Lys Leu Ser Met Ile Asp Val
        275                 280                 285

Arg Gln Ala Met Lys Ile Ser Lys Asp Ile Tyr Thr Lys Leu Lys Glu
    290                 295                 300
```

```
Thr Ile Asp Asp Gly Ser Pro Thr Lys Ile Met Leu Pro Ala Phe Val
305                 310                 315                 320

Phe Asn Pro Lys Lys His Ser Phe Lys Gln Ala Ile Val Ala Gln His
                325                 330                 335

Glu Val Glu Ser Asp Asp Ala Phe Cys
                340                 345
```

<210> SEQ ID NO 32
<211> LENGTH: 7
<212> TYPE: PRT
<213> ORGANISM: hemorrhagic enteritis virus

<400> SEQUENCE: 32

```
Val Phe Gln Cys Cys Asn Pro
1               5
```

<210> SEQ ID NO 33
<211> LENGTH: 12
<212> TYPE: PRT
<213> ORGANISM: adeno-associated virus 2

<400> SEQUENCE: 33

```
Arg Leu Pro Val Arg Arg Arg Arg Arg Arg Val Pro
1               5                   10
```

<210> SEQ ID NO 34
<211> LENGTH: 12
<212> TYPE: PRT
<213> ORGANISM: EDS

<400> SEQUENCE: 34

```
Thr Leu Pro Ala Arg Thr Arg Arg Thr Arg Arg Pro
1               5                   10
```

<210> SEQ ID NO 35
<211> LENGTH: 12
<212> TYPE: PRT
<213> ORGANISM: hemorrhagic enteritis virus

<400> SEQUENCE: 35

```
Ser Leu Pro Leu Ile Arg Arg Ile Arg Arg Pro Pro
1               5                   10
```

<210> SEQ ID NO 36
<211> LENGTH: 5
<212> TYPE: PRT
<213> ORGANISM: hemorrhagic enteritis virus

<400> SEQUENCE: 36

```
Leu Arg Gly Gly Lys
1               5
```

<210> SEQ ID NO 37
<211> LENGTH: 11
<212> TYPE: PRT
<213> ORGANISM: Unknown
<220> FEATURE:
<223> OTHER INFORMATION: Description of Unknown Organism: Conserved
      sequence
<220> FEATURE:
<221> NAME/KEY: MISC_FEATURE
<222> LOCATION: (2)..(6)
<223> OTHER INFORMATION: X=Tyr or Arg or Phe
<220> FEATURE:
<221> NAME/KEY: MISC_FEATURE

```
<222> LOCATION: (9)..(9)
<223> OTHER INFORMATION: X=Tyr or Arg
<220> FEATURE:
<221> NAME/KEY: MISC_FEATURE
<222> LOCATION: (11)..(11)
<223> OTHER INFORMATION: X=Phe or Tyr

<400> SEQUENCE: 37

Gly Xaa Xaa Xaa Xaa Xaa Arg Arg Xaa Cys Xaa
1               5                   10

<210> SEQ ID NO 38
<211> LENGTH: 7
<212> TYPE: PRT
<213> ORGANISM: adeno-associated virus 2
<220> FEATURE:
<221> NAME/KEY: MISC_FEATURE
<222> LOCATION: (4)..(4)
<223> OTHER INFORMATION: X=Tyr or Arg or Phe
<220> FEATURE:
<221> NAME/KEY: MISC_FEATURE
<222> LOCATION: (6)..(6)
<223> OTHER INFORMATION: X=Tyr or Arg or Phe

<400> SEQUENCE: 38

Met Leu Ile Xaa Gly Xaa Gly
1               5

<210> SEQ ID NO 39
<211> LENGTH: 7
<212> TYPE: PRT
<213> ORGANISM: adeno-associated virus 2
<220> FEATURE:
<221> NAME/KEY: MISC_FEATURE
<222> LOCATION: (4)..(4)
<223> OTHER INFORMATION: X=Tyr or Arg or Phe
<220> FEATURE:
<221> NAME/KEY: MISC_FEATURE
<222> LOCATION: (7)..(7)
<223> OTHER INFORMATION: X=Tyr or Arg or Phe

<400> SEQUENCE: 39

Met Leu Ile Xaa Gly Gly Xaa
1               5

<210> SEQ ID NO 40
<211> LENGTH: 6
<212> TYPE: PRT
<213> ORGANISM: hemorrhagic enteritis virus

<400> SEQUENCE: 40

Gly Gly Gly Asn Gly Gly
1               5

<210> SEQ ID NO 41
<211> LENGTH: 4
<212> TYPE: PRT
<213> ORGANISM: hemorrhagic enteritis virus

<400> SEQUENCE: 41

Lys Lys Arg Lys
1

<210> SEQ ID NO 42
<211> LENGTH: 4
```

-continued

```
<212> TYPE: PRT
<213> ORGANISM: hemorrhagic enteritis virus

<400> SEQUENCE: 42

Lys Lys Asn Lys
1
```